US011717380B2

(12) United States Patent
Pokotilov et al.

(10) Patent No.: US 11,717,380 B2
(45) Date of Patent: Aug. 8, 2023

(54) AUTOMATED 2D/3D INTEGRATION AND LIP SPLINE AUTOPLACEMENT

(71) Applicant: ALIGN TECHNOLOGY, INC., San Jose, CA (US)

(72) Inventors: Pavel Pokotilov, Moscow (RU); Dmitry Yurievich Chekh, Moscow (RU); Dmitriy Konstantinovich Ten, Novosibirsk (RU); Samuel Blanco, Santa Clara, CA (US); David Patrick Lopes, El Dorado Hills, CA (US); Jason Ramos, Heredia (CR); Rene M. Sterental, Palo Alto, CA (US); Evgenii Vladimirovich Karnygin, Moscow (RU); Vladislav Andreevich Miryaha, Engels (RU); Boris Aleksandrovich Vysokanov, Moscow (RU); Yury A. Brailov, Moscow (RU); Artem Kuanbekov, Moscow (RU)

(73) Assignee: Align Technology, Inc., San Jose, CA (US)

( * ) Notice: Subject to any disclaimer, the term of this patent is extended or adjusted under 35 U.S.C. 154(b) by 0 days.

(21) Appl. No.: 17/088,909

(22) Filed: Nov. 4, 2020

(65) Prior Publication Data
US 2021/0045843 A1 Feb. 18, 2021

Related U.S. Application Data

(63) Continuation of application No. 15/926,952, filed on Mar. 20, 2018, now Pat. No. 10,828,130.
(Continued)

(51) Int. Cl.
*G06K 9/00* (2022.01)
*A61C 7/00* (2006.01)
(Continued)

(52) U.S. Cl.
CPC ............... *A61C 7/002* (2013.01); *A61C 7/08* (2013.01); *A61C 9/0053* (2013.01); *G06T 17/20* (2013.01);
(Continued)

(58) Field of Classification Search
CPC ...................................... A61C 7/002
See application file for complete search history.

(56) References Cited

U.S. PATENT DOCUMENTS 2,467,432 A 4/1949 Kesling
3,407,500 A 10/1968 Kesling
(Continued)

FOREIGN PATENT DOCUMENTS

AU 3031677 A 5/1979
AU 517102 B2 7/1981
(Continued)

OTHER PUBLICATIONS

Co-pending U.S. Appl. No. 17/005,951, inventors Pokotilov; Pavel et al., filed Aug. 28, 2020.
(Continued)

*Primary Examiner* — Oneal R Mistry
(74) *Attorney, Agent, or Firm* — Fortem IP LLP

(57) ABSTRACT

A method may include: receiving an image of a mouth region of a patient's face; extracting teeth contours within the image of the mouth region of the patient's face; locating a mouth opening within the image of the mouth region of the patient's face; extracting the tooth contours from a 3D model of the patient's teeth; and aligning the tooth contours from the 3D model with the tooth contours of the teeth within the image of the mouth region of the patient's face.

20 Claims, 57 Drawing Sheets

Related U.S. Application Data

(60) Provisional application No. 62/474,026, filed on Mar. 20, 2017.

(51) Int. Cl.

| | | |
|---|---|---|
| *A61C 9/00* | (2006.01) | |
| *A61C 7/08* | (2006.01) | |
| *G16H 20/40* | (2018.01) | |
| *G16H 50/20* | (2018.01) | |
| *G06T 17/20* | (2006.01) | |
| *B33Y 50/00* | (2015.01) | |
| *B33Y 80/00* | (2015.01) | |
| *G16H 50/50* | (2018.01) | |

(52) U.S. Cl.
CPC ............. *G16H 20/40* (2018.01); *G16H 50/20* (2018.01); *B33Y 50/00* (2014.12); *B33Y 80/00* (2014.12); *G06T 2207/30036* (2013.01); *G16H 50/50* (2018.01)

(56) References Cited

U.S. PATENT DOCUMENTS

| | | |
|---|---|---|
| 3,600,808 A | 8/1971 | Reeve et al. |
| 3,660,900 A | 5/1972 | Andrews et al. |
| 3,683,502 A | 8/1972 | Wallshein et al. |
| 3,738,005 A | 6/1973 | Cohen et al. |
| 3,860,803 A | 1/1975 | Levine |
| 3,916,526 A | 11/1975 | Schudy |
| 3,922,786 A | 12/1975 | Lavin |
| 3,950,851 A | 4/1976 | Bergersen |
| 3,983,628 A | 10/1976 | Acevedo |
| 4,014,096 A | 3/1977 | Dellinger |
| 4,195,046 A | 3/1980 | Kesling et al. |
| 4,253,828 A | 3/1981 | Coles et al. |
| 4,324,546 A | 4/1982 | Heitlinger et al. |
| 4,324,547 A | 4/1982 | Arcan et al. |
| 4,348,178 A | 9/1982 | Kurz |
| 4,478,580 A | 10/1984 | Barrut et al. |
| 4,500,294 A | 2/1985 | Lewis et al. |
| 4,504,225 A | 3/1985 | Yoshii |
| 4,505,673 A | 3/1985 | Yoshii et al. |
| 4,526,540 A | 7/1985 | Dellinger et al. |
| 4,575,330 A | 3/1986 | Hull et al. |
| 4,575,805 A | 3/1986 | Moermann et al. |
| 4,591,341 A | 5/1986 | Andrews et al. |
| 4,609,349 A | 9/1986 | Cain et al. |
| 4,611,288 A | 9/1986 | Duret et al. |
| 4,656,860 A | 4/1987 | Orthuber et al. |
| 4,663,720 A | 5/1987 | Duret et al. |
| 4,664,626 A | 5/1987 | Kesling et al. |
| 4,676,747 A | 6/1987 | Kesling et al. |
| 4,742,464 A | 5/1988 | Duret et al. |
| 4,755,139 A | 7/1988 | Abbatte et al. |
| 4,763,791 A | 8/1988 | Halverson et al. |
| 4,793,803 A | 12/1988 | Martz et al. |
| 4,798,534 A | 1/1989 | Breads et al. |
| 4,836,778 A | 6/1989 | Baumrind et al. |
| 4,837,732 A | 6/1989 | Brandestini et al. |
| 4,850,864 A | 7/1989 | Diamond et al. |
| 4,850,865 A | 7/1989 | Napolitano et al. |
| 4,856,991 A | 8/1989 | Breads et al. |
| 4,877,398 A | 10/1989 | Kesling et al. |
| 4,880,380 A | 11/1989 | Martz et al. |
| 4,889,238 A | 12/1989 | Batchelor et al. |
| 4,890,608 A | 1/1990 | Steer et al. |
| 4,935,635 A | 6/1990 | O'Harra et al. |
| 4,936,862 A | 6/1990 | Walker et al. |
| 4,937,928 A | 7/1990 | Van Der Zel |
| 4,941,826 A | 7/1990 | Loran et al. |
| 4,964,770 A | 10/1990 | Steinbichler et al. |
| 4,975,052 A | 12/1990 | Spencer et al. |
| 4,983,334 A | 1/1991 | Adell et al. |
| 5,011,405 A | 4/1991 | Lemchen |
| 5,017,133 A | 5/1991 | Miura et al. |
| 5,027,281 A | 6/1991 | Rekow et al. |
| 5,035,613 A | 7/1991 | Breads et al. |
| 5,055,039 A | 10/1991 | Abbatte et al. |
| 5,059,118 A | 10/1991 | Breads et al. |
| 5,100,316 A | 3/1992 | Wildman et al. |
| 5,121,333 A | 6/1992 | Riley et al. |
| 5,125,832 A | 6/1992 | Kesling |
| 5,128,870 A | 7/1992 | Erdman et al. |
| 5,130,064 A | 7/1992 | Smalley et al. |
| 5,131,843 A | 7/1992 | Hilgers et al. |
| 5,131,844 A | 7/1992 | Marinaccio et al. |
| 5,139,419 A | 8/1992 | Andreiko et al. |
| 5,145,364 A | 9/1992 | Martz et al. |
| 5,176,517 A | 1/1993 | Truax et al. |
| 5,184,306 A | 2/1993 | Erdman et al. |
| 5,186,623 A | 2/1993 | Breads et al. |
| 5,257,203 A | 10/1993 | Riley et al. |
| 5,273,429 A | 12/1993 | Rekow et al. |
| 5,278,756 A | 1/1994 | Lemchen et al. |
| 5,328,362 A | 7/1994 | Watson et al. |
| 5,338,198 A | 8/1994 | Wu et al. |
| 5,340,309 A | 8/1994 | Robertson et al. |
| 5,342,202 A | 8/1994 | Deshayes et al. |
| 5,368,478 A | 11/1994 | Andreiko et al. |
| 5,382,164 A | 1/1995 | Stern et al. |
| 5,395,238 A | 3/1995 | Andreiko et al. |
| 5,431,562 A | 7/1995 | Andreiko et al. |
| 5,440,326 A | 8/1995 | Quinn et al. |
| 5,440,496 A | 8/1995 | Andersson et al. |
| 5,447,432 A | 9/1995 | Andreiko et al. |
| 5,452,219 A | 9/1995 | Dehoff et al. |
| 5,454,717 A | 10/1995 | Andreiko et al. |
| 5,456,600 A | 10/1995 | Andreiko et al. |
| 5,474,448 A | 12/1995 | Andreiko et al. |
| RE35,169 E | 3/1996 | Lemchen et al. |
| 5,518,397 A | 5/1996 | Andreiko et al. |
| 5,528,735 A | 6/1996 | Strasnick et al. |
| 5,533,895 A | 7/1996 | Andreiko et al. |
| 5,542,842 A | 8/1996 | Andreiko et al. |
| 5,549,476 A | 8/1996 | Stern et al. |
| 5,562,448 A | 10/1996 | Mushabac |
| 5,587,912 A | 12/1996 | Andersson et al. |
| 5,605,459 A | 2/1997 | Kuroda et al. |
| 5,607,305 A | 3/1997 | Andersson et al. |
| 5,614,075 A | 3/1997 | Andre, Sr. et al. |
| 5,621,648 A | 4/1997 | Crump et al. |
| 5,645,420 A | 7/1997 | Bergersen et al. |
| 5,645,421 A | 7/1997 | Slootsky et al. |
| 5,655,653 A | 8/1997 | Chester et al. |
| 5,683,243 A | 11/1997 | Andreiko et al. |
| 5,692,894 A | 12/1997 | Schwartz et al. |
| 5,725,376 A | 3/1998 | Poirier et al. |
| 5,725,378 A | 3/1998 | Wang et al. |
| 5,733,126 A | 3/1998 | Andersson et al. |
| 5,740,267 A | 4/1998 | Echerer et al. |
| 5,742,700 A | 4/1998 | Yoon et al. |
| 5,799,100 A | 8/1998 | Clarke et al. |
| 5,800,174 A | 9/1998 | Andersson et al. |
| 5,823,778 A | 10/1998 | Schmitt et al. |
| 5,848,115 A | 12/1998 | Little et al. |
| 5,857,853 A | 1/1999 | Van Nifterick et al. |
| 5,866,058 A | 2/1999 | Batchelder et al. |
| 5,879,158 A | 3/1999 | Doyle et al. |
| 5,880,961 A | 3/1999 | Crump et al. |
| 5,880,962 A | 3/1999 | Andersson et al. |
| 5,934,288 A | 8/1999 | Avila et al. |
| 5,957,686 A | 9/1999 | Anthony et al. |
| 5,964,587 A | 10/1999 | Sato et al. |
| 5,971,754 A | 10/1999 | Sondhi et al. |
| 5,975,893 A | 11/1999 | Chishti et al. |
| 6,015,289 A | 1/2000 | Andreiko et al. |
| 6,044,309 A | 3/2000 | Honda et al. |
| 6,049,743 A | 4/2000 | Baba |
| 6,062,861 A | 5/2000 | Andersson |
| 6,068,482 A | 5/2000 | Snow et al. |
| 6,099,314 A | 8/2000 | Kopelman et al. |
| 6,123,544 A | 9/2000 | Cleary |
| 6,152,731 A | 11/2000 | Jordan et al. |

(56) References Cited

U.S. PATENT DOCUMENTS

| | | | |
|---|---|---|---|
| 6,183,248 B1 | 2/2001 | Chishti et al. |
| 6,190,165 B1 | 2/2001 | Andreiko et al. |
| 6,217,325 B1 | 4/2001 | Chishti et al. |
| 6,217,334 B1 | 4/2001 | Hultgren et al. |
| 6,244,861 B1 | 6/2001 | Andreiko et al. |
| 6,309,215 B1 | 10/2001 | Phan et al. |
| 6,315,553 B1 | 11/2001 | Sachdeva et al. |
| 6,322,359 B1 | 11/2001 | Jordan et al. |
| 6,350,120 B1 | 2/2002 | Sachdeva et al. |
| 6,382,975 B1 | 5/2002 | Poirier et al. |
| 6,398,548 B1 | 6/2002 | Muhammad et al. |
| 6,402,707 B1 | 6/2002 | Ernst et al. |
| 6,450,807 B1 | 9/2002 | Chishti et al. |
| 6,482,298 B1 | 11/2002 | Bhatnagar et al. |
| 6,524,101 B1 | 2/2003 | Phan et al. |
| 6,554,611 B2 | 4/2003 | Shishti et al. |
| 6,572,372 B1 | 6/2003 | Phan et al. |
| 6,629,840 B2 | 10/2003 | Chishti et al. |
| 6,705,863 B2 | 3/2004 | Phan et al. |
| 6,722,880 B2 | 4/2004 | Chishti et al. |
| 6,749,414 B1 | 6/2004 | Hanson et al. |
| 6,830,450 B2 | 12/2004 | Knopp et al. |
| 6,845,175 B2 | 1/2005 | Kopelman et al. |
| 7,156,655 B2 | 1/2007 | Sachdeva et al. |
| 7,292,716 B2 | 11/2007 | Kim |
| 7,530,811 B2 | 5/2009 | Kaufmann et al. |
| 7,695,278 B2 | 4/2010 | Sporbert et al. |
| 7,717,708 B2 | 5/2010 | Sachdeva et al. |
| 7,892,474 B2 | 2/2011 | Shkolnik et al. |
| 8,177,551 B2 | 5/2012 | Sachdeva et al. |
| 8,545,221 B2 | 10/2013 | Stone-Collonge et al. |
| 9,205,601 B2 | 12/2015 | DeSimone et al. |
| 9,211,678 B2 | 12/2015 | DeSimone et al. |
| 9,216,546 B2 | 12/2015 | DeSimone et al. |
| 9,321,215 B2 | 4/2016 | Dudley |
| 9,511,543 B2 | 12/2016 | Tyler |
| 9,549,785 B2 | 1/2017 | Kim |
| 9,848,965 B2 | 12/2017 | Kim et al. |
| 9,861,451 B1 | 1/2018 | Davis |
| 10,049,467 B2 | 8/2018 | Im et al. |
| 10,342,645 B2 | 7/2019 | Salah et al. |
| 10,758,322 B2 | 9/2020 | Pokotilov et al. |
| 10,828,130 B2 | 11/2020 | Pokotilov et al. |
| 2002/0006597 A1 | 1/2002 | Andreiko et al. |
| 2003/0009252 A1 | 1/2003 | Pavlovskaia et al. |
| 2003/0139834 A1 | 7/2003 | Nikolskiy et al. |
| 2003/0224311 A1 | 12/2003 | Cronauer et al. |
| 2004/0015327 A1 | 1/2004 | Sachdeva et al. |
| 2004/0029068 A1 | 2/2004 | Sachdeva et al. |
| 2004/0128010 A1 | 7/2004 | Pavlovskaia et al. |
| 2004/0197727 A1 | 10/2004 | Sachdeva et al. |
| 2005/0055118 A1 | 3/2005 | Nikolskiy et al. |
| 2005/0280644 A1 | 12/2005 | Ikezawa |
| 2007/0134613 A1 | 6/2007 | Kuo et al. |
| 2007/0183633 A1* | 8/2007 | Hoffmann ............... G06V 40/16 382/116 |
| 2008/0280247 A1 | 11/2008 | Sachdeva et al. |
| 2009/0220918 A1 | 9/2009 | Kaufmann et al. |
| 2009/0291408 A1 | 11/2009 | Stone-Collonge et al. |
| 2009/0298017 A1* | 12/2009 | Boerjes ................ A61B 5/4547 433/214 |
| 2010/0007665 A1* | 1/2010 | Smith ..................... G06T 13/40 345/473 |
| 2010/0151404 A1 | 6/2010 | Wu et al. |
| 2010/0179789 A1 | 7/2010 | Sachdeva et al. |
| 2011/0159451 A1 | 6/2011 | Kuo et al. |
| 2013/0218530 A1* | 8/2013 | Deichmann ............. A61C 5/77 703/1 |
| 2013/0297275 A1 | 11/2013 | Sanchez |
| 2014/0061974 A1 | 3/2014 | Tyler |
| 2014/0265034 A1 | 9/2014 | Dudley |
| 2014/0379356 A1 | 12/2014 | Sachdeva et al. |
| 2015/0058004 A1* | 2/2015 | Dimitriadis ............. G10L 25/78 704/233 |
| 2015/0079544 A1 | 3/2015 | Boltunov et al. |
| 2015/0097315 A1 | 4/2015 | DeSimone et al. |
| 2015/0097316 A1 | 4/2015 | DeSimone et al. |
| 2015/0102532 A1 | 4/2015 | DeSimone et al. |
| 2015/0265374 A1 | 9/2015 | Masoud |
| 2016/0175068 A1 | 6/2016 | Cai et al. |
| 2016/0220173 A1* | 8/2016 | Ribnick ................ A61B 5/7278 |
| 2016/0239631 A1 | 8/2016 | Wu et al. |
| 2016/0275679 A1 | 9/2016 | Im et al. |
| 2016/0310235 A1 | 10/2016 | Derakhshan et al. |
| 2017/0065379 A1 | 3/2017 | Cowburn et al. |
| 2017/0262994 A1* | 9/2017 | Kudriashov ........... G06T 11/001 |
| 2017/0281110 A1* | 10/2017 | Mandelkern .......... G06T 7/0014 |
| 2017/0281313 A1* | 10/2017 | Kim ...................... A61C 7/002 |
| 2017/0319293 A1 | 11/2017 | Fisker |
| 2018/0025529 A1* | 1/2018 | Wu .......................... G01J 3/501 345/426 |
| 2018/0028294 A1* | 2/2018 | Azernikov ........ G06F 18/24143 |
| 2018/0085198 A1 | 3/2018 | Chen et al. |
| 2018/0110590 A1* | 4/2018 | Maraj .................... A61C 7/002 |
| 2018/0263731 A1 | 9/2018 | Pokotilov et al. |
| 2018/0325484 A1* | 11/2018 | Patel ..................... G16H 30/20 |
| 2018/0360411 A1 | 12/2018 | Abkai |
| 2019/0125492 A1 | 5/2019 | Lin et al. |
| 2020/0085535 A1 | 3/2020 | Pokotilov et al. |
| 2020/0312043 A1 | 10/2020 | Peng et al. |

FOREIGN PATENT DOCUMENTS

| | | |
|---|---|---|
| AU | 5598894 A | 6/1994 |
| CA | 1121955 A | 4/1982 |
| DE | 2749802 A1 | 5/1978 |
| DE | 69327661 T2 | 7/2000 |
| EP | 0091876 A1 | 10/1983 |
| EP | 0299490 A2 | 1/1989 |
| EP | 0376873 A2 | 7/1990 |
| EP | 0490848 A2 | 6/1992 |
| EP | 0541500 A1 | 5/1993 |
| EP | 0667753 B1 | 1/2000 |
| EP | 0774933 B1 | 12/2000 |
| EP | 0731673 B1 | 5/2001 |
| ES | 463897 A1 | 1/1980 |
| FR | 2369828 A1 | 6/1978 |
| FR | 2652256 A1 | 3/1991 |
| GB | 1550777 A | 8/1979 |
| JP | S5358191 A | 5/1978 |
| JP | H0428359 A | 1/1992 |
| JP | H08508174 A | 9/1996 |
| JP | 3672966 B2 | 7/2005 |
| WO | WO-9008512 A1 | 8/1990 |
| WO | WO-9104713 A1 | 4/1991 |
| WO | WO-9410935 A1 | 5/1994 |
| WO | WO-9832394 A1 | 7/1998 |
| WO | WO-9844865 A1 | 10/1998 |
| WO | WO-9858596 A1 | 12/1998 |
| WO | 2006065955 A2 | 6/2006 |
| WO | WO-2018175486 A1 | 9/2018 |

OTHER PUBLICATIONS

AADR. American Association for Dental Research, Summary of Activities, Mar. 20-23, 1980, Los Angeles, CA, p. 195.

Alcaniz, et al., "An Advanced System for the Simulation and Planning of Orthodontic Treatments," Karl Heinz Hohne and Ron Kikinis (eds.), Visualization in Biomedical Computing, 4th Intl. Conf., VBC '96, Hamburg, Germany, Sep. 22-25, 1996, Springer-Verlag, pp. 511-520.

Alexander et al., "The DigiGraph Work Station Part 2 Clinical Management," JCO, pp. 402-407 (Jul. 1990).

Altschuler, "3D Mapping of Maxillo-Facial Prosthesis," AADR Abstract #607, 2 pages total, (1980).

Altschuler et al., "Analysis of 3-D Data for Comparative 3-D Serial Growth Pattern Studies of Oral-Facial Structures," IADR Abstracts, Program and Abstracts of Papers, 57th General Session, IADR Annual Session, Mar. 29, 1979-Apr. 1, 1979, New Orleans Marriot, Journal of Dental Research, vol. 58, Jan. 1979, Special Issue A, p. 221.

(56) References Cited

OTHER PUBLICATIONS

Altschuler et al., "Laser Electro-Optic System for Rapid Three-Dimensional (3D) Topographic Mapping of Surfaces," Optical Engineering, 20(6):953-961 (1981).
Altschuler et al., "Measuring Surfaces Space-Coded by a Laser-Projected Dot Matrix," SPIE Imaging Applications for Automated Industrial Inspection and Assembly, vol. 182, p. 187-191 (1979).
Andersson et al., "Clinical Results with Titanium Crowns Fabricated with Machine Duplication and Spark Erosion," Acta. Odontol. Scand., 47:279-286 (1989).
Andrews, The Six Keys to Optimal Occlusion Straight Wire, Chapter 3, pp. 13-24 (1989).
Bartels, et al., An Introduction to Splines for Use in Computer Graphics and Geometric Modeling, Morgan Kaufmann Publishers, pp. 422-425 (1987).
Baumrind, "A System for Craniofacial Mapping Through the Integration of Data from Stereo X-Ray Films and Stereo Photographs," an invited paper submitted to the 1975 American Society of Photogram Symposium on Close-Range Photogram Systems, University of Ill., Aug. 26-30, 1975, pp. 142-166.
Baumrind et al., "A Stereophotogrammetric System for the Detection of Prosthesis Loosening in Total Hip Arthroplasty," NATO Symposium on Applications of Human Biostereometrics, Jul. 9-13, 1978, SPIE, vol. 166, pp. 112-123.
Baumrind et al., "Mapping the Skull in 3-D," reprinted from J. Calif. Dent. Assoc., 48(2), 11 pages total, (1972 Fall Issue).
Baumrind, "Integrated Three-Dimensional Craniofacial Mapping: Background, Principles, and Perspectives," Semin. in Orthod., 7(4):223-232 (Dec. 2001).
Begole et al., "A Computer System for the Analysis of Dental Casts," The Angle Orthod., 51(3):253-259 (Jul. 1981).
Bernard et al.,"Computerized Diagnosis in Orthodontics for Epidemiological Studies: A Progress Report," Abstract, J. Dental Res. Special Issue, vol. 67, p. 169, paper presented at International Association for Dental Research 66th General Session, Mar. 9-13, 1988, Montreal, Canada.
Bhatia et al., "A Computer-Aided Design for Orthognathic Surgery," Br. J. Oral Maxillofac. Surg., 22:237-253 (1984).
Biggerstaff, "Computerized Diagnostic Setups and Simulations," Angle Orthod., 40(1):28-36 (Jan. 1970).
Biggerstaff et al., "Computerized Analysis of Occlusion in the Postcanine Dentition," Am. J. Orthod., 61(3): 245-254 (Mar. 1972).
Biostar Opeation & Training Manual. Great Lakes Orthodontics, Ltd. 199 Fire Tower Drive, Tonawanda, New York. 14150-5890, 20 pages total (1990).
Blu, et al., "Linear interpolation revitalized", IEEE Trans. Image Proc., 13(5):710-719 (May 2004).
Bourke, "Coordinate System Transformation," (Jun. 1996), p. 1, retrieved from the Internet Nov. 5, 2004, URL http://astronomy.swin.edu.au/—pbourke/prolection/coords.
Boyd et al., "Three Dimensional Diagnosis and Orthodontic Treatment of Complex Malocclusions With the Invisalign Appliance," Semin. Orthod., 7(4):274-293 (Dec. 2001).
Brandestini et al., "Computer Machined Ceramic Inlays: In Vitro Marginal Adaptation," J. Dent. Res. Special Issue, Abstract 305, vol. 64, p. 208 (1985).
Brook et al., "An Image Analysis System for the Determination of Tooth Dimensions from Study Casts: Comparison with Manual Measurements of Mesio-distal Diameter," J. Dent. Res., 65(3):428-431 (Mar. 1986).
Burstone et al., Precision Adjustment of the Transpalatal Lingual Arch: Computer Arch Form IN Predetermination, Am, Journal of Orthodontics, vol. 79, No. 2 (Feb. 1981), pp. 115-133.
Burstone (interview), "Dr. Charles J. Burstone on The Uses of the Computer in Orthodontic Practice (Part 1)," J. Clin. Orthod., 13(7):442-453 (Jul. 1979).
Burstone (interview), "Dr. Charles J. Burstone on The Uses of the Computer in Orthodontic Practice (Part 2)," J. Clin. Orthod., 13(8):539-551 (Aug. 1979).

Cardinal Industrial Finishes, Powder Coatings information posted at http://www.cardinalpaint.com on Aug. 25, 2000, 2 pages.
Carnaghan, "An Alternative to Holograms for the Portrayal of Human Teeth," 4th Int'l. Conf. on Holographic Systems, Components and Applications, Sep. 15, 1993, pp. 228-231.
Chaconas et al., "The DigiGraph Work Station, Part 1, Basic Concepts," JCO, pp. 360-367 (Jun. 1990).
Chafetz et al., "Subsidence of the Femoral Prosthesis, A Stereophotogrammetric Evaluation," Clin. Orthop. Relat. Res., No. 201, pp. 60-67 (Dec. 1985).
Chiappone, (1980). Constructing the Gnathologic Setup and Positioner, J. Clin. Orthod, vol. 14, pp. 121-133.
Cottingham, (1969). Gnathologic Clear Plastic Positioner, Am. J. Orthod, vol. 55, pp. 23-31.
Crawford, "CAD/CAM in the Dental Office: Does It Work?", Canadian Dental Journal, vol. 57, No. 2, pp. 121-123 (Feb. 1991).
Crawford, "Computers in Dentistry: Part 1 CAD/CAM: The Computer Moves Chairside," Part 2 F. Duret—A Man with a Vision, "Part 3 The Computer Gives New Vision—Literally," Part 4 Bytes 'N Bites—The Computer Moves from the Front Desk to the Operatory, Canadian Dental Journal, vol. 54 (9), pp. 661-666 (1988).
Crooks, "CAD/CAM Comes to USC," USC Dentistry, pp. 14-17 (Spring 1990).
Cureton, Correcting Malaligned Mandibular Incisors with Removable Retainers, J. Clin. Orthod., vol. 30, No. 7 (1996) pp. 390-395.
Curry et al., "Integrated Three-Dimensional Craniofacial Mapping at the Craniofacial Research Instrumentation Laboratory/University of the Pacific," Semin. Orthod., 7(4):258-265 (Dec. 2001).
Cutting et a/., "Three-Dimensional Computer-Assisted Design of Craniofacial Surgical Procedures: Optimization and Interaction with Cephalometric and CT-Based Models," Plast. 77(6):877-885 (Jun. 1986).
DCS Dental AG, "The CAD/CAM 'DCS Titan System' for Production of Crowns/Bridges," DSC Production AG, pp. 1-7 (Jan. 1992.
Definition for gingiva. Dictionary.com p. 1-3. Retrieved from the internet Nov. 5, 2004 http://reference.com/search/search?q=gingiva.
Defranco et al., "Three-Dimensional Large Displacement Analysis of Orthodontic Appliances," J. Biomechanics, 9:793-801 (1976).
Dental Institute University of Zurich Switzerland, Program for International Symposium JD on Computer Restorations: State of the Art of the CEREC-Method, May 1991, 2 pages total.
Dentrac Corporation, Dentrac document, pp. 4-13 (1992).
DENT-X posted on Sep. 24, 1998 at http://www.dent-x.com/DentSim.htm, 6 pages.
Doyle, "Digital Dentistry," Computer Graphics World, pp. 50-52, 54 (Oct. 2000).
DuraClearTM product information, Allesee Orthodontic Appliances-Pro Lab, 1 page (1997).
Duret et al., "CAD/CAM Imaging in Dentistry," Curr. Opin. Dent., 1:150-154 (1991).
Duret et al, "CAD-CAM in Dentistry," J. Am. Dent. Assoc. 117:715-720 (Nov. 1988).
Duret, "The Dental CAD/CAM, General Description of the Project," Hennson International Product Brochure, 18 pages total, Jan. 1986.
Duret,"Vers Une Prosthese Informatisee," (English translation attached), Tonus, vol. 75, pp. 55-57 (Nov. 15, 1985).
Economides, "The Microcomputer in the Orthodontic Office," JCO, pp. 767-772 (Nov. 1979).
Elsasser, Some Observations on the History and Uses of the Kesling Positioner, Am. J. Orthod. (1950) 36:368-374.
English translation of Japanese Laid-Open Publication No. 63-11148 to inventor T. Ozukuri (Laid-Open on Jan. 18, 1998) pp. 1-7.
Felton et al., "A Computerized Analysis of the Shape and Stability of Mandibular Arch Form," Am. J. Orthod. Dentofacial Orthop., 92(6):478-483 (Dec. 1987).
Friede et al., "Accuracy of Cephalometric Prediction in Orthognathic Surgery," Abstract of Papers, J. Dent. Res., 70:754-760 (1987).

(56) References Cited

OTHER PUBLICATIONS

Futterling et al., "Automated Finite Element Modeling of a Human Mandible with Dental Implants," JS WSCG '98—Conference Program, retrieved from the Internet: http://wscg.zcu.cz/wscg98/papers98/Strasser 98.pdf, 8 pages.

Gao et al., "3-D element Generation for Multi-Connected Complex Dental and Mandibular Structure," Proc. Intl Workshop on Medical Imaging and Augmented Reality, pp. 267-271 (Jun. 12, 2001).

GIM-ALLDENT Deutschland, "Das DUX System: Die Technik," 2 pages total (2002).

Gottleib et al., "JCO Interviews Dr. James A. McNamura, Jr., on the Frankel Appliance: Part 2: Clinical 1-1 Management," J. Clin. Orthod., 16(6):390-407 (Jun. 1982).

Grayson, "New Methods for Three Dimensional Analysis of Craniofacial Deformity, Symposium: JW Computerized Facial Imaging in Oral and Maxillofacial Surgery," AAOMS, 3 pages total, (Sep. 13, 1990).

Guess et al., "Computer Treatment Estimates In Orthodontics and Orthognathic Surgery," JCO, pp. 262-28 (Apr. 1989).

Heaven et al., "Computer-Based Image Analysis of Artificial Root Surface Caries," Abstracts of Papers, J. Dent. Res., 70:528 (Apr. 17-21, 1991).

Highbeam Research, "Simulating Stress Put on Jaw," Tooling & Production [online], Nov. 1996, n pp. 1-2, retrieved from the Internet on Nov. 5, 2004, URL http://static.highbeam.com/t/toolingampproduction/november011996/simulatingstressputonfa . . . .

Hikage, "Integrated Orthodontic Management System for Virtual Three-Dimensional Computer Graphic Simulation and Optical Video Image Database for Diagnosis and Treatment Planning", Journal of Japan KA Orthodontic Society, Feb. 1987, English translation, pp. 1-38, Japanese version, 46(2), pp. 248-269 (60 pages total).

Hoffmann, et al., "Role of Cephalometry for Planning of Jaw Orthopedics and Jaw Surgery Procedures," (Article Summary in English, article in German), Informationen, pp. 375-396 (Mar. 1991).

Hojjatie et al., "Three-Dimensional Finite Element Analysis of Glass-Ceramic Dental Crowns," J. Biomech., 23(11):1157-1166 (1990).

Huckins, "CAD-CAM Generated Mandibular Model Prototype from MRI Data," AAOMS, p. 96 (1999).

Important Tip About Wearing the Red White & Blue Active Clear Retainer System. Allesee Orthodontic Appliances-Pro Lab. 1 page (1998).

International search report with written opinion dated Aug. 29, 2018 for PCT/US2018/023423.

JCO Interviews, "Craig Andreiko, DDS, MS on the Elan and Orthos Systems," JCO, pp. 459-468 (Aug. 1994).

JCO Interviews, "Dr. Homer W. Phillips on Computers in Orthodontic Practice, Part 2," JCO. 1997; 1983:819-831.

Jerrold, "The Problem, Electronic Data Transmission and the Law," AJO-DO, pp. 478-479 (Apr. 1988).

Jones et al., "An Assessment of the Fit of a Parabolic Curve to Pre- and Post-Treatment Dental Arches," Br. J. Orthod., 16:85-93 (1989).

JP Faber et al., "Computerized Interactive Orthodontic Treatment Planning," Am. J. Orthod., 73(1):36-46 (Jan. 1978).

Kamada et.al., Case Reports On Tooth Positioners Using LTV Vinyl Silicone Rubber, J. Nihon University School of Dentistry (1984) 26(1): 11-29.

Kamada et.al., Construction of Tooth Positioners with LTV Vinyl Silicone Rubber and Some Case KJ Reports, J. Nihon University School of Dentistry (1982) 24(1):1-27.

Kanazawa et al., "Three-Dimensional Measurements of the Occlusal Surfaces of Upper Molars in a Dutch Population," J. Dent Res., 63(11):1298-1301 (Nov. 1984).

Kesling, Coordinating the Predetermined Pattern and Tooth Positioner with Conventional Treatment, KN Am. J. Orthod. Oral Surg. (1946) 32:285-293.

Kesling et al., The Philosophy of the Tooth Positioning Appliance, American Journal of Orthodontics and Oral surgery. 1945; 31:297-304.

Kleeman et al., The Speed Positioner, J. Clin. Orthod. (1996) 30:673-680.

Kochanek, "Interpolating Splines with Local Tension, Continuity and Bias Control," Computer Graphics, ri 18(3):33-41 (Jul. 1984).

KM Oral Surgery (1945) 31 :297-30.

Kunii et al., "Articulation Simulation for an Intelligent Dental Care System," Displays 15:181-188 (1994).

Kuroda et al., Three-Dimensional Dental Cast Analyzing System Using Laser Scanning, Am. J. Orthod. Dentofac. Orthop. (1996) 110:365-369.

Laurendeau, et al., "A Computer-Vision Technique for the Acquisition and Processing of 3-D Profiles of 7 KR Dental Imprints: An Application in Orthodontics," IEEE Transactions on Medical Imaging, 10(3):453-461 (Sep. 1991.

Leinfelder, et al., "A New Method for Generating Ceramic Restorations: a CAD-CAM System," J. Am. 1-1 Dent. Assoc., 118(6):703-707 (Jun. 1989).

Manetti, et al., "Computer-Aided Cefalometry and New Mechanics in Orthodontics," (Article Summary in English, article in German), Fortschr Kieferorthop. 44, 370-376 (Nr. 5), 1983.

McCann, "Inside the ADA," J. Amer. Dent. Assoc., 118:286-294 (Mar. 1989).

McNamara et al., "Invisible Retainers," J. Clin. Orthod., pp. 570-578 (Aug. 1985).

McNamara et al., Orthodontic and Orthopedic Treatment in the Mixed Dentition, Needham Press, pp. 347-353 (Jan. 1993).

Moermann et al., "Computer Machined Adhesive Porcelain Inlays: Margin Adaptation after Fatigue Stress," IADR Abstract 339, J. Dent. Res., 66(a):763 (1987).

Moles, "Correcting Mild Malalignments—As Easy As One, Two, Three," AOA/Pro Corner, vol. 11, No. 1, 2 pages (2002).

Mormann et al., "Marginale Adaptation von adhasuven Porzellaninlays in vitro," Separatdruck aus: Schweiz. Mschr. Zahnmed. 95: 1118-1129, 1985.

Nahoum, "The Vacuum Formed Dental Contour Appliance," N. Y. State Dent. J., 30(9):385-390 (Nov. 1964).

Nash, "CEREC CAD/CAM Inlays: Aesthetics and Durability in a Single Appointment," Dent. Today, 9(8):20, 22-23 (Oct. 1990).

Nishiyama et al., "A New Construction of Tooth Repositioner by LTV Vinyl Silicone Rubber," J. Nihon Univ. Sch. Dent., 19(2):93-102 (1977).

Paul et al., "Digital Documentation of Individual Human Jaw and Tooth Forms for Applications in Orthodontics, Oral Surgery and Forensic Medicine" Proc. of the 24th Annual Conf. of the IEEE Industrial Electronics Society (IECON '98), Sep. 4, 1998, pp. 2415-2418.

Pinkham, "Foolish Concept Propels Technology," Dentist, 3 pages total, Jan./Feb. 1989.

Pinkham, "Inventor's CAD/CAM May Transform Dentistry," Dentist, 3 pages total, Sep. 1990.

Ponitz, "Invisible Retainers," Am. J. Orthod., 59(3):266-272 (Mar. 1971).

PROCERA Research Projects, "PROCERA Research Projects 1993—Abstract Collection," pp. 3-7; 28 (1993).

Proffit et al., Contemporary Orthodontics, (Second Ed.), Chapter 15, Mosby Inc., pp. 470-533 (Oct. 1993).

Raintree Essix & ARS Materials, Inc., Raintree Essix, Technical Magazine Table of contents and Essix Appliances, http://www.essix.com/magazine/defaulthtml Aug. 13, 1997.

Redmond et al., "Clinical Implications of Digital Orthodontics," Am. J. Orthod. Dentofacial Orthop., 117(2):240-242 (2000).

Rekow, "A Review of the Developments in Dental CAD/CAM Systems," (contains references to Japanese efforts and content of the papers of particular interest to the clinician are indicated with a one line summary of their content in the bibliography), Curr. Opin. Dent., 2:25-33 (Jun. 1992).

Rekow, "CAD/CAM in Dentistry: A Historical Perspective and View of the Future," J. Can. Dent. Assoc., 58(4):283, 287-288 (Apr. 1992).

Rekow, "Computer-Aided Design and Manufacturing in Dentistry: A Review of the State of the Art," J. Prosthet. Dent., 58(4):512-516 (Oct. 1987).

(56) References Cited

OTHER PUBLICATIONS

Rekow, "Dental CAD-CAM Systems: What is the State of the Art?", J. Amer. Dent. Assoc., 122:43-48 1991.
Rekow et al., "CAD/CAM for Dental Restorations—Some of the Curious Challenges," IEEE Trans. Biomed. Eng., 38(4):314-318 (Apr. 1991).
Rekow et al., "Comparison of Three Data Acquisition Techniques for 3-D Tooth Surface Mapping," Annual International Conference of the IEEE Engineering in Medicine and Biology Society, 13(1):344-345 1991.
Rekow, "Feasibility of an Automated System for Production of Dental Restorations, Ph.D. Thesis," Univ. of Minnesota, 244 pages total, Nov. 1988.
Richmond et al., "The Development of a 3D Cast Analysis System," Br. J. Orthod., 13(1):53-54 (Jan. 1986).
Richmond et al., "The Development of the PAR Index (Peer Assessment Rating): Reliability and Validity," Eur. J. Orthod., 14:125-139 (1992).
Richmond, "Recording The Dental Cast In Three Dimensions," Am. J. Orthod. Dentofacial Orthop., 92(3):199-206 (Sep. 1987).
Rudge, "Dental Arch Analysis: Arch Form, A Review of the Literature," Eur. J. Orthod., 3(4):279-284 1981.
Sakuda et al., "Integrated Information-Processing System In Clinical Orthodontics: An Approach with Use of a Computer Network System," Am. J. Orthod. Dentofacial Orthop., 101(3): 210-220 (Mar. 1992).
Schellhas et al., "Three-Dimensional Computed Tomography in Maxillofacial Surgical Planning," Arch. Otolaryngol Head Neck Surg., 114:438-442 (Apr. 1988).
Schroeder et al., Eds. The Visual Toolkit, Prentice Hall PTR, New Jersey (1998) Chapters 6, 8 & 9, (pp. 153-210,309-354, and 355-428, respectively.
Shilliday, (1971). Minimizing finishing problems with the mini-positioner, Am. J. Orthod. 59:596-599.
Siemens, "CEREC—Computer-Reconstruction," High Tech in der Zahnmedizin, 14 pages total (2004).
Sinclair, "The Readers' Corner," J. Clin. Orthod., 26(6):369-372 (Jun. 1992).
Sirona Dental Systems GmbH, CEREC 3D, Manuel utilisateur, Version 2.0X (in French), 2003,114 pages total.
Stoll et al., "Computer-aided Technologies in Dentistry," (article summary in English, article in German), Dtsch Zahna'rztl Z 45, pp. 314-322 (1990).
Sturman, "Interactive Keyframe Animation of 3-D Articulated Models," Proceedings Graphics Interface '84, May-Jun. 1984, pp. 35-40.
The Choice Is Clear: Red, White & Blue . . . The Simple, Affordable, No-Braces Treatment, Allesee Orthodontic Appliances-Pro Lab product information, 6 pages (2003).
The Choice Is Clear: Red, White & Blue . . . The Simple, Affordable, No-Braces Treatment, Allesee HI Orthodontic Appliances-Pro Lab product information for doctors. http://ormco.com/aoa/appliancesservices/RWB/doctorhtml, 5 pages (May 19, 2003).
The Choice Is Clear: Red, White & Blue . . . The Simple, Affordable, No-Braces Treatment, Allesee HJ Orthodontic Appliances-Pro Lab product information for patients, (http://ormco.com/aoa/appliancesservices/RWB/patients.html), 2 pages (May 19, 2003).
The Red, White & Blue Way to Improve Your Smile!, Allesee Orthodontic Appliances-Pro Lab product information for patients, 2 pages (1992).
Truax L., "Truax Clasp-Less(TM) Appliance System," Funct. Orthod., 9(5):22-4, 26-8 (Sep.-Oct. 1992).
Tru-Tain Orthodontic & Dental Supplies, Product Brochure, Rochester, Minnesota 55902, 16 pages total (1996).
U.S. Department of Commerce, National Technical Information Service, "Automated Crown Replication Using Solid Photography SM," Solid Photography Inc., Melville NY, Oct. 1977, 20 pages total.
U.S. Department of Commerce, National Technical Information Service, "Holodontography: An Introduction to Dental Laser Holography," School of Aerospace Medicine Brooks AFB Tex, Mar. 1973, 37 pages total.
U.S. Appl. No. 60/050,342, filed Jun. 20, 1997, 41 pages total.
Van Der Linden, "A New Method to Determine Tooth Positions and Dental Arch Dimensions," J. Dent. Res., 51(4):1104 (Jul.-Aug. 1972).
Van Der Linden et al., "Three-Dimensional Analysis of Dental Casts by Means of the Optocom," J. Dent. Res., p. 1100 (Jul.-Aug. 1972).
Van Der Zel, "Ceramic-Fused-to-Metal Restorations with a New CAD/CAM System," Quintessence Int., 24(11)769-778 (1993.
Varady et al., "Reverse Engineering Of Geometric Models—An Introduction," Computer-Aided Design, 29(4):255-268,1997.
Verstreken et al., "An Image-Guided Planning System for Endosseous Oral Implants," IEEE Trans. Med. Imaging, 17(5):842-852 (Oct. 1998).
Ward D.: Proportional Smile Design Using Recurring Esthetic Dental (RED) Proportion. Dental Clinics of North America 45(1): 143-154 (2001).
Warunek et al., Physical and Mechanical Properties of Elastomers in Orthodonic Positioners, Am J. Orthod. Dentofac. Orthop, vol. 95, No. 5, (May 1989) pp. 388-400.
Warunek et.al., Clinical Use of Silicone Elastomer Applicances, JCO (1989) XXIII(10):694-700.
Wells, Application of the Positioner Appliance in Orthodontic Treatment, Am. J. Orthodont. (1970) 58:351-366.
Williams, "Dentistry and CAD/CAM: Another French Revolution," J. Dent. Practice Admin., pp. 2-5 (Jan./Mar. 1987).
Williams, "The Switzerland and Minnesota Developments in CAD/CAM," J. Dent. Practice Admin., pp. 50-55 (Apr./Jun. 1987).
Wishan, "New Advances in Personal Computer Applications for Cephalometric Analysis, Growth Prediction, Surgical Treatment Planning and Imaging Processing," Symposium: Computerized Facial Imaging in Oral and Maxilofacial Surgery Presented on Sep. 13, 1990.
WSCG'98—Conference Program, "The Sixth International Conference in Central Europe on Computer Graphics and Visualization '98," Feb. 9-13, 1998, pp. 1-7, retrieved from the Internet on Nov. 5, 2004, URL(http://wscg.zcu.cz/wscg98/wscg98.h).
Wu et al.: Model-Based Teeth Reconstruction. SA '16 Technical Papers. Dec. 5-8, 2016. ISBN: 978-1-4503-4514-9/16/12. DOI: http://dx.doi.org/10.1145/2980179.2980233. 13 pages.
Xia et al., "Three-Dimensional Virtual-Reality Surgical Planning and Soft-Tissue Prediction for Orthognathic Surgery," IEEE Trans. Inf. Technol. Biomed., 5(2):97-107 (Jun. 2001).
Yamamoto et al., "Optical Measurement of Dental Cast Profile and Application to Analysis of Three-Dimensional Tooth Movement in Orthodontics," Front. Med. Biol. Eng., 1(2):119-130 (1988).
Yamamoto et al., "Three-Dimensional Measurement of Dental Cast Profiles and Its Applications to Orthodontics," Conf. Proc. IEEE Eng. Med. Biol. Soc., 12(5):2051-2053 (1990).
Yamany et al., "A System for Human Jaw Modeling Using Intra-Oral Images," Proc. of the 20th Annual Conf. of the IEEE Engineering in Medicine and Biology Society, Nov. 1, 1998, vol. 2, pp. 563-566.
Yoshii, "Research on a New Orthodontic Appliance: The Dynamic Positioner (D.P.); I. The D.P. Concept and Implementation of Transparent Silicone Resin (Orthocon)," Nippon Dental Review, 452:61-74 (Jun. 1980).
Yoshii, "Research on a New Orthodontic Appliance: The Dynamic Positioner (D.P.); II. The D.P. Manufacturing Procedure and Clinical Applications," Nippon Dental Review, 454:107-130 (Aug. 1980).
Yoshii, "Research on a New Orthodontic Appliance: The Dynamic Positioner (D.P.); III. The General Concept of the D.P. Method and Its Therapeutic Effect, Part 1, Dental and Functional Reversed Occlusion Case Reports," Nippon Dental Review, 457:146-164 (Nov. 1980).
Yoshii, "Research on a New Orthodontic Appliance: The Dynamic Positioner (D.P.); III.—The General Concept of the D.P. Method and Its Therapeutic Effect, Part 2. Skeletal Reversed Occlusion Case Reports," Nippon Dental Review, 458:112-129 (Dec. 1980).

(56) References Cited

OTHER PUBLICATIONS

You May Be A Candidate For This Invisible No-Braces Treatment, Allesee Orthodontic Appliances-Pro Lab product information for patients, 2 pages (2002).

Brugarolas. Advances in obstructive sleep apnea treatment: Development of an autoadjusting mandibular repositioning device for in-home use. Published Oct. 11, 2015. 9 pages.

* cited by examiner

500B

```
Gathering a three-dimensional model of the patient's dentition, the three-dimensional model
comprising a virtual representation of the patient's dentition at a specific treatment stage of
an orthodontic treatment plan
582
```

```
Gathering an image of the patient, the image including at least a portion of the patient's face
and including at least a portion of the patient's dentition
584
```

```
Receiving first identifiers of a first set of reference points modeled on the three-dimensional
model of the patient's dentition, the first set of reference points corresponding to a set of
anatomical points on the patient's dentition
586
```

```
Receiving second identifiers of a second set of reference points represented on the dentition
of the image of the patient, the second set of reference points corresponding to the set of
anatomical points on the patient's dentition
588
```

```
Projecting the image of the patient's dentition into a three-dimensional space to create a
projected 3D model of the image of the patient's dentition
590
```

```
Aligning the first set of reference points on the three-dimensional model of the patient's
dentition with the second set of reference points on projected model of the image of the
patient
592
```

```
Providing instructions to display a modified image of the patient, the modified image
representing thereon the aligned first and second sets of reference points
594
```

FIG. 5B

AUTOMATED 2D/3D INTEGRATION AND LIP SPLINE AUTOPLACEMENT

CROSS-REFERENCE

This application is a continuation of U.S. application Ser. No. 15/926,952, filed on Mar. 20, 2018, which claims the benefit of U.S. Provisional Application No. 62/474,026, filed Mar. 20, 2017, which application is incorporated herein by reference.

BACKGROUND

In the design of virtual representations of living beings, an "uncanny valley" can relate to the extent a virtual object's resemblance to a living being corresponds to emotional responses to the virtual object. The concept of an uncanny valley may suggest humanoid virtual objects which appear almost, but not exactly, like real human beings (robots, 3D computer animations, lifelike dolls, etc.) elicit uncanny, or strangely familiar, feelings of eeriness and revulsion in observers. A virtual object that appears "almost" human risks may elicit cold, eerie, and/or other non-emotional feelings in viewers.

In the context of treatment planning, the uncanny valley problem may cause people to negatively react to humanoid representations of themselves. As an example, people viewing a 3D virtual representation of themselves after an orthodontic treatment plan may be confronted with an unfamiliar, robotic, or non-humanoid view of themselves.

These issues may undermine perceptions of treatment planning proposals and/or lead to negative perceptions of treatment planning proposals. These issues may influence decision making with respect to the proper alignment of teeth in a human patient when three-dimensional (3D) renderings of digital models of patient's teeth are combined with two-dimensional (2D) images or photos of a patient.

Furthermore, orthodontic treatment planning processes may not take into account facial relationships between the positions and orientations of teeth and the shape and position of facial features of a patient.

Systems and methods that reduce the uncanny valley reaction and take into account the relationships between the positions and orientations of teeth and the shape and position of facial features of a patient could help in increasing the effectiveness and acceptance of orthodontic treatment, particularly orthodontic treatments involving virtual representations and/or virtual 3D models of living beings before, during and/or after the application of orthodontic treatment plans.

SUMMARY

This disclosure generally relates to system and methods of correcting malocclusions of teeth. More particularly, the disclosure relates to system and methods of accurately and realistically depicting 3D bite models of teeth in a 2D image of patient and systems and methods of determining the final orthodontic and restorative object positions for teeth.

Systems and methods are described herein to more closely integrate 3D bite models into 2D images of a patient to aid in reducing or eliminating the uncanny valley reaction and aid in providing better decision making with respect to the proper alignment of teeth.

In addition, orthodontic systems and methods are introduced that evaluate the shape of a patient's face and the relationships between the positions and orientations of teeth and the shape and position of facial features of a patient in the treatment planning processes such that the final orthodontic and resorted position and shape of the patient teeth more closely match an ideal position with respect to each particular patient.

A method of orthodontically treating a patient is disclosed. The method may include building a 3D model of the patient's dentition and forming an image a patient including at least a portion of the patient's face and including at least a portion of the patient's dentition. The method may also include selecting a first set of reference points on the 3D model of the patient's dentition. The method may include selecting a second set of reference points on the dentition of the image of the patient and combining the 3D model of the patient's dentition with the image of the patient. The method may also include aligning the first set of reference points on the 3D model of the patient's dentition with the second set of reference points on the image of the patient.

Computer-readable media, computer systems having processors and memory, and computer-implemented methods of orthodontically treating a patient may comprise: building a three-dimensional model of the patient's dentition; forming an image of the patient including at least a portion of the patient's face and including at least a portion of the patient's dentition; selecting a first set of reference points on the three-dimensional model of the patient's dentition; selecting a second set of reference points on the dentition of the image of the patient; combining the three-dimensional model of the patient's dentition with the image of the patient; and aligning the first set of reference points on the three-dimensional model of the patient's dentition with the second set of reference points on the image of the patient.

In some implementations, at least one reference point in the first set of reference points corresponds to a respective reference point in the second set of reference points. In some implementations, the corresponding reference points are at similar locations on the three-dimensional model and the image of the patient. In some implementations, the similar locations are the gingival apex of at least two teeth. In some implementations, the similar locations are the midpoint of incisal edges. In some implementations, the similar locations are cusp tips.

In some implementations, the image of the patient is a two-dimensional image of the patient. In some implementations, contours of the teeth in the three-dimensional model of the patient's dentition are aligned with contours of teeth in the image of the patient. In some implementations, the aligning includes minimizing the square of the distance between the first set of reference points on the three-dimensional model and the second set of reference points on the image of the patient.

Computer-readable media, computer systems having processors and memory, and computer-implemented methods of orthodontically treating a patient may comprise: combining a three-dimensional bite model with an image of a patient; rendering the three-dimensional bite model according to a first set of parameters; determining a quality metric for the rendered three-dimensional bite model as compared to the image of the patient; selecting a second set of parameters to improve the quality metric for the rendered three-dimensional bite model as compared to the image of the patient; and rendering the three-dimensional bite model according to a second set of parameters.

In some implementations, the method may further comprise: determining a quality metric for the rendered three-dimensional bite model as compared to the image of the patient; and comparing the quality metric to a threshold value; determining if the quality metric at least meets the threshold value; and generating a final composite image of the patient based on the three-dimensional bite model rendered according to a second set of parameters and the image of the patient, if the quality metric at least meets the threshold value.

In some implementations, the image of the patient is a two-dimensional image. In some implementations, rendering the three-dimensional bite model according to the second set of parameters includes rendering the three-dimensional bite model according to an interim position of the teeth according to a treatment plan for moving the patient's teeth from an initial position towards a final position.

In some implementations, rendering the three-dimensional bite model according to the second set of parameters includes rendering the three-dimensional bite model according to a final position of the teeth according to a treatment plan for moving the patient's teeth from an initial position towards a final position.

In some implementations, the first and second parameters include a color intensity. In some implementations, the first and second parameters include a luminance intensity. In some implementations, the first and second parameters include a tooth whiteness. In some implementations, the first and second parameters include a blur. In some implementations, the first and second parameters include a shadow filter.

Computer-readable media, computer systems having processors and memory, and computer-implemented methods for correcting malocclusions of a patient's teeth comprising: receiving an initial position of a patient teeth; determining an interim final orthodontic position of a patient's teeth; applying at least one interim restorative object to at least one of the patient's teeth; determining an interim tooth mass loss for the at least one of the patient's teeth; determining a final orthodontic position of a patient's teeth; applying at least one final restorative object to at least one of the patient's teeth; and determining a final tooth mass loss for the at least one of the patient's teeth, wherein the final tooth mass loss is less than the interim tooth mass loss.

In some implementations determining an interim tooth mass loss for the at least one of the patient's teeth includes: determining an initial mass of the patient's tooth before preparing the tooth for the interim restorative object; determining a prepared mass of the patient's tooth based on the shape of the tooth when prepared for receiving the interim restorative object; and subtracting the prepared mass from the initial mass.

In some implementations, determining tooth mass loss includes determining the volume loss of the tooth. In some implementations, determining the volume loss of the tooth for the at least one of the patient's teeth includes: determining an initial volume of the patient's tooth before preparing the tooth for the interim restorative object; determining a prepared volume of the patient's tooth after preparing the tooth for the interim restorative object; and subtracting the prepared volume from the initial mass.

In some implementations, determining tooth mass loss includes determining the tooth mass loss of the crown of the tooth. In some implementations, the interim restorative object is a crown. In some implementations, the final restorative object is a veneer.

Computer-readable media, computer systems having processors and memory, and computer-implemented methods of determining a final position of a patient's teeth comprising: receiving an initial position of a patient teeth; determining an interim final orthodontic position of the patient's teeth; receiving an image of the patient's face; selecting a first set of reference objects on the image of the patient's face; selecting a second set of reference objects on the patient's teeth; and revising the interim final orthodontic position of the patient's teeth based on distances between points in the first set of reference objects and the second set of reference objects.

In some implementations, the first set of reference objects include a facial midline and the second set of reference objects include a dental midline. In some implementations, revising the interim final orthodontic position of the patient's teeth includes changing the position of the patient's teeth in the interim final orthodontic position such that a distance between the facial midline and the dental midlines is less than a threshold value.

In some implementations, the first set of reference objects include a location of the inferior boarder of the upper lip at the facial midline and the second set of reference objects include an incisal edge position. In some implementations, revising the interim final orthodontic position of the patient's teeth includes changing the position of the patient's teeth in the interim final orthodontic position such that a distance between the location of the inferior boarder of the upper lip at the facial midline and the incisal edge position is less than a threshold value.

In some implementations, the first set of reference objects include a location of the superior boarder of the lower lip at the facial midline and the second set of reference objects include an incisal edge position. In some implementations, revising the interim final orthodontic position of the patient's teeth includes changing the position of the patient's teeth in the interim final orthodontic position such that a distance between the location of the superior boarder of the lower lip at the facial midline and the incisal edge position is less than a threshold value.

In some implementations, the first set of reference objects include a location of the inferior boarder of the upper lip at the facial midline and the second set of reference objects include a gingival zenith of a central incisor. In some implementations, revising the interim final orthodontic position of the patient's teeth includes changing the position of the patient's teeth in the interim final orthodontic position such that a distance between the location of the inferior boarder of the upper lip at the facial midline and the gingival zenith of the central incisor is less than a threshold value.

In some implementations, widths of the central incisors, lateral incisors, and canines in the interim final position are modified based on facial type. In some implementations, the modification includes application of restorative objects.

In some implementations, widths of the central incisors, lateral incisors, and canines in the interim final position are modified based on an inter-canine width and facial type.

In some implementations, facial type is determined based on a distance between the patient's glabella and chin and the distance between the patient's right and left cheekbone prominences.

Computer-readable media, computer systems having processors and memory, and computer-implemented methods of orthodontically treating a patient's teeth comprising: receiving facial image of the patient that depicts the patient's teeth; receiving a 3D model of the patient's teeth; determining color palette of the depiction of the patient's teeth; color coding 3D model of the patient's teeth based on attributes of the 3D model; providing the 3D model, the color palette, and the color-coded 3D model to a neural network; processing the 3D model, the color palette, and the color-coded 3D model by the neural network to generate a processed image of the patient's teeth; and inserting the processed image of the patient's teeth into a mouth opening of the facial image.

In some implementations, a spline may be formed at the edge of the inner lips to define the mouth opening of the facial image. In some implementations, the neural network is trained using facial images of people that depict their teeth. In some implementations, the processed image of the patient's teeth is blurred. In some implementations, the blurring occurs after inserting the processed image of the patient's teeth into the mouth opening of the facial image. In some implementations, the blurring is alpha channel blurring.

In some implementations, generating the color palette comprises: blurring the depiction of the patient's teeth from the facial image.

In some implementations, the blurring is a Gaussian blur.

In some implementations, the facial image is a 2D facial image. In some implementations, color coding the 3D model comprises coding a color channel of a plurality of pixels of a 2D rendering of the 3D model with attributes of the 3D model or the facial image. In some implementations, the attributes are one or more of the brightness of the patient's teeth at each pixel location, the angle of the surface of the 3D model with respect to the facial plane at each pixel location, and the dental structure type of the 3D model at each pixel location. In some implementations, the brightness of the patient's teeth location at each pixel location is determined based on the brightness of a blurred depiction of the patient's teeth from the facial image. In some implementations, the dental structure is one or more of an identity of each tooth or the gingiva in the 3D model at each pixel location Computer-readable media, computer systems having processors and memory, and computer-implemented methods of orthodontically treating a patient's teeth comprising: receiving an image of a mouth region of a patient's face; extracting teeth contours within the image of the mouth region of the patient's face; locating a mouth opening within the image of the mouth region of the patient's face; extracting the tooth contours from a 3D model of the patient's teeth; and aligning the tooth contours from the 3D model with the tooth contours of the teeth within the image of the mouth region of the patient's face.

In some implementations, a rendering of the 3D model may be inserted into the mouth opening based on the alignment of the tooth contours from the 3D model with the tooth contours of the teeth within the image of the mouth region of the patient's face.

In some implementations, receiving the image of the mouth region of the patient's face comprises: receiving a facial image of the patient; identifying facial landmarks on the facial image, the facial landmarks including lip landmarks and other landmarks; and cropping the facial image around the lip landmarks to exclude the other landmarks.

In some implementations, the other landmarks include one or more of eye, nose and facial outline landmarks.

In some implementations, extracting the teeth contours within the image of the mouth region of the patient's face comprises: detecting the tooth contours using a convolutional neural network.

In some implementations, the convolutional neural network comprises a holistic edge detection deep learning model.

In some implementations, each pixel of the tooth contours has a value. In some implementations, the tooth contours are binarized. In some implementations, binarizing the tooth contours comprises: comparing the value of each pixel to a threshold; and assigning a new value to each pixel, the new value being a first value if the pixel is greater than the threshold and a second value of the value is less than the threshold.

In some implementations, the tooth contours are thinned. In some implementations, thinning the tooth contours comprises reducing the width of the tooth contours to a single pixel at each location along the tooth contours.

In some implementations, aligning the tooth contours from the 3D model with the tooth contours of the teeth within the image of the mouth region of the patient's face comprises: using an expectation-maximization algorithm to align the tooth contour from the 3D model with the tooth contours of the teeth within the image, where during an expectation-step, each pixel on the tooth contours from the 3D model is matched to a similar pixel on the contours of the 3D tooth model and during a maximization step, the teeth are adjusted in one or more of translation and rotation in one or more of three orthogonal direction to minimize the total discrepancies between pixels of the tooth contours from the 3D model and the tooth contours of the teeth within the image.

In some implementations, locating the mouth opening within the image of the mouth region of the patient's face comprises: detecting the tooth contours using a convolutional neural network; binarizing the tooth contours; and thinning the tooth contours.

In some implementations, the convolutional neural network comprises a holistic edge detection deep learning model.

In some implementations, each pixel of the tooth contours has a value.

In some implementations, binarizing the tooth contours comprises: comparing the value of each pixel to a threshold; and assigning a new value to each pixel, the new value being a first value if the pixel is greater than the threshold and a second value of the value is less than the threshold.

In some implementations, thinning the tooth contours comprises reducing the width of the tooth contours to a single pixel at each location along the tooth contours.

In some implementations, methods further include: forming a first plurality of connected splines along a lower lip portion of the lip contour, the plurality of connected splines starting at a first end of the lip contour and ending at a second end of the lip contour; and forming a second plurality of connected splines along an upper lip portion of the lip contour, the plurality of connected splines starting at the first end of the lip contour and ending at the second end of the lip contour, wherein the first and second lip splines define the mouth opening.

Computer-readable media, computer systems having processors and memory, and computer-implemented methods of orthodontically treating a patient's teeth, comprise: receiving a facial image a patient; identifying facial landmarks on the facial image; generating a facial midline based on the landmarks; forming a facial midline plane based on the facial midline; receiving a 3D tooth model having a dental midline; and aligning the 3D tooth model with the facial image of the patient by aligning the dental midline with the facial midline plane.

In some implementations, the landmarks are symmetric landmarks. In some implementations, each of the symmetric landmarks is a midpoint between a corresponding pair of facial landmarks, a first of the pair identifying a feature on a left side of the patient's face and a second of the pair identifying the same feature on the right side of the face.

In some implementations, the landmarks are central landmarks.

In some implementations, each of the central landmarks is one of a nasal ridge landmark; a nose tip landmark, a center lip landmark, a center chin landmark. In some implementations, the landmarks are symmetric landmarks and central landmarks.

In some implementations, generating a facial midline based on the landmarks comprises: generating a plurality of interim facial midlines and determining the R-squared fit between each of the facial midlines and the facial landmarks; and wherein the facial midline is the interim facial midline with the highest R-squared fit.

In some implementations, generating a facial midline based on the landmarks comprises: generating a plurality of interim facial midlines and determining a sum of the square of the distances of the facial midlines and the facial landmarks; and wherein the facial midline is the interim facial midline with the lowest sum of the square of the distances.

In some implementations, one or more of the facial landmarks is assigned a weigh used in determining a sum of the square of the distances of the facial midlines and the facial landmarks.

In some implementations, aligning the 3D tooth model with the facial image of the patient by aligning the dental midline with the facial midline plane comprise one or more of rotation the facial image, rotating the 3D model, and translating the 3D model.

Computer-readable media, computer systems having processors and memory, and computer-implemented methods may include: gathering a three-dimensional model of the patient's dentition, the three-dimensional model comprising a virtual representation of the patient's dentition at a specific treatment stage of an orthodontic treatment plan; gathering an image of the patient, the image including at least a portion of the patient's face and including at least a portion of the patient's dentition; receiving first identifiers of a first set of reference points modeled on the three-dimensional model of the patient's dentition, the first set of reference points corresponding to a set of anatomical points on the patient's dentition; receiving second identifiers of a second set of reference points represented on the dentition of the image of the patient, the second set of reference points corresponding to the set of anatomical points on the patient's dentition; projecting the image of the patient's dentition into a three-dimensional space to create a projected 3D model of the image of the patient's dentition; aligning the first set of reference points on the three-dimensional model of the patient's dentition with the second set of reference points on projected model of the image of the patient; providing instructions to display a modified image of the patient, the modified image representing thereon the aligned first and second sets of reference points.

In some implementations, at least one reference point in the first set of reference points corresponds to a respective reference point in the second set of reference points. In some implementations, the anatomical points are at similar locations on the three-dimensional model and the image of the patient. In some implementations, the similar locations are the gingival apex of at least two teeth. In some implementations, the similar locations are the midpoint of incisal edges. In some implementations, wherein the similar locations are cusp tips.

In some implementations, the image of the patient is a two-dimensional image of the patient. In some implementations, contours of the teeth in the three-dimensional model of the patient's dentition are aligned with contours of teeth in the image of the patient. In some implementations, the aligning includes minimizing the square of the distance between the first set of reference points on the three-dimensional model and the second set of reference points on the projected model of the image of the patient.

In some implementations, the specific treatment stage is an estimated intermediate stage or an estimated final stage of the orthodontic treatment plan. In some implementations, image represents the patients' dentition before the orthodontic treatment plan. In some implementations, the image is captured from a scanner or uploaded from a computer or a mobile phone. In some implementations, the image is uploaded over a network connection.

Computer-readable media, computer systems having processors and memory, and computer-implemented methods may include: identifying, using a first three-dimensional (3D) representation of a patient's teeth, an initial position of the patient teeth; determining, using a virtual representation of one or more force systems applied to the patient's teeth, an estimated interim final orthodontic position of the patient's teeth; gathering one or more images of the patient's face; identifying one or more facial reference objects on the image of the patient's face, the facial reference objects corresponding to a physical or anatomical feature providing a first reference position to the patient's face; identifying one or more dental reference objects on the first 3D representation of the patient's teeth, the one or more dental reference objects corresponding to physical or anatomical feature providing a second reference position to the patient's dentition; identifying a relationship between the one or more facial reference objects and the one or more dental reference objects; modifying the estimated interim final orthodontic position of the patient's teeth in the first 3D representation based on the relationship between the one or more facial reference objects and the one or more dental reference objects; and providing instructions to integrate a modified estimated interim final orthodontic position based on the relationship between the one or more facial reference objects and the one or more dental reference objects.

In some implementations, the one or more facial reference objects include a facial midline and the one or more dental reference objects include a dental midline. In some implementations, modifying the estimated interim final orthodontic position of the patient's teeth includes changing the position of the patient's teeth in the estimated interim final orthodontic position such that a distance between the facial midline and the dental midlines meets or does not exceed a threshold value. In some implementations, the one or more facial reference objects include a location of the inferior boarder of the upper lip at the facial midline and the one or more dental reference objects include an incisal edge position. In some implementations, modifying the estimated interim final orthodontic position of the patient's teeth includes changing the position of the patient's teeth in the estimated interim final orthodontic position such that a distance between the location of the inferior boarder of the upper lip at the facial midline and the incisal edge position meets or does not exceed a threshold value.

In some implementations, the one or more facial reference objects include a location of the superior boarder of the lower lip at the facial midline and the one or more dental reference objects include an incisal edge position.

In some implementations, modifying the estimated interim final orthodontic position of the patient's teeth includes changing the position of the patient's teeth in the estimated interim final orthodontic position such that a distance between the location of the superior boarder of the lower lip at the facial midline and the incisal edge position meets or does not exceed a threshold value. In some implementations, the one or more facial reference objects include a location of the inferior boarder of the upper lip at the facial midline and the one or more dental reference objects include a gingival zenith of a central incisor. In some implementations, modifying the estimated interim final orthodontic position of the patient's teeth includes changing the position of the patient's teeth in the interim final orthodontic position such that a distance between the location of the inferior boarder of the upper lip at the facial midline and the gingival zenith of the central incisor meets or does not exceed a threshold value. In some implementations, widths of the central incisors, lateral incisors, and canines in the interim final position are modified based on facial type. In some implementations, the modification includes application of restorative objects.

In some implementations, widths of the central incisors, lateral incisors, and canines in the interim final position are modified based on an inter-canine width and facial type. In some implementations, facial type is determined based on a distance between the patient's glabella and chin and the distance between the patient's right and left cheekbone prominences.

In some implementations, instructions to design or manufacture an orthodontic appliance using the modified estimated interim final position are provided.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

FIG. 5B depicts a method of building a composite image, in accordance with one or more embodiments herein;

DETAILED DESCRIPTION

Figure 1A:
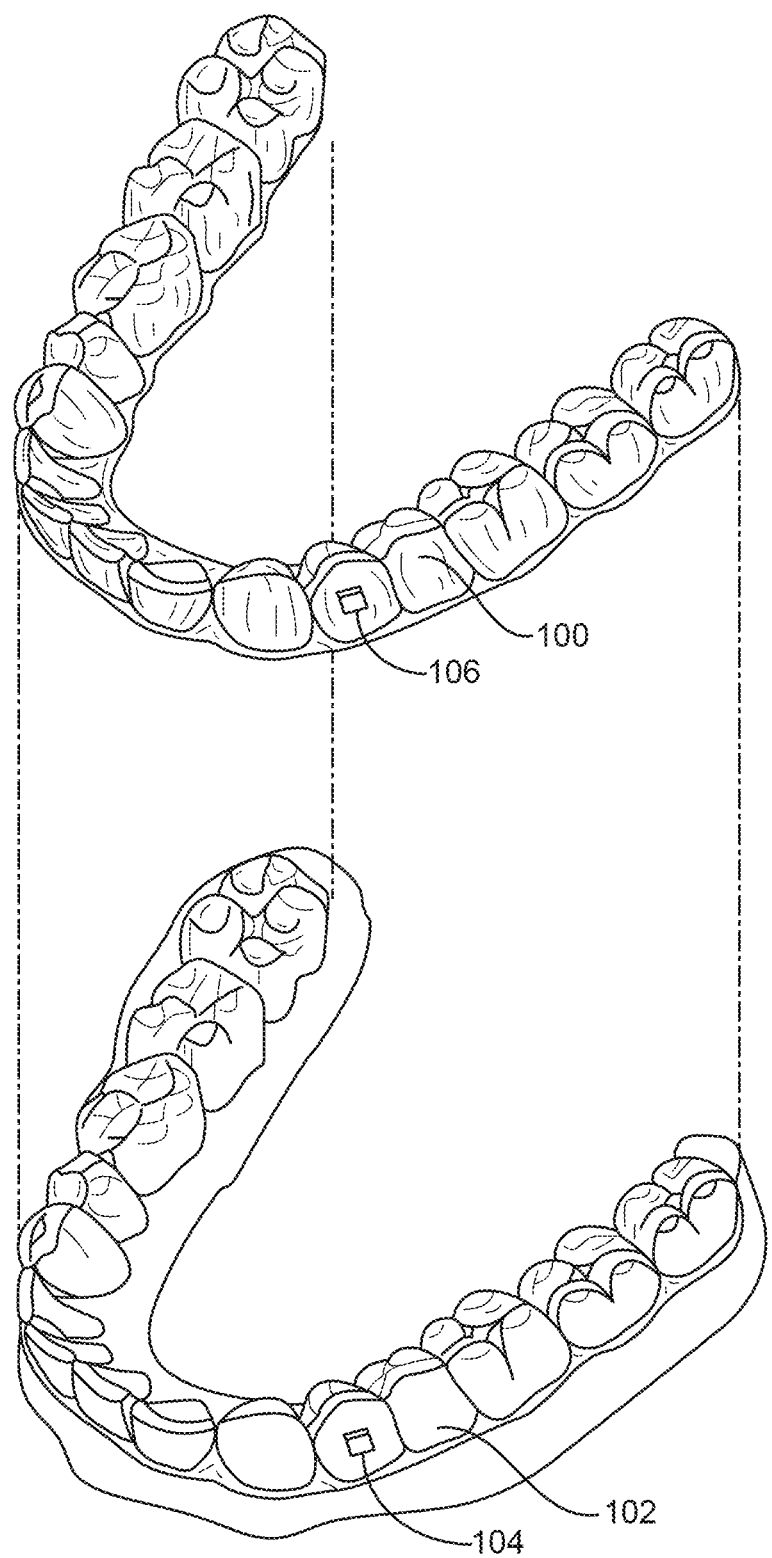
FIG. 1A illustrates a tooth repositioning appliance, in accordance with one or more embodiments herein.

A better understanding of the features and advantages of the present disclosure will be obtained by reference to the following detailed description that sets forth illustrative embodiments, in which the principles of embodiments of the present disclosure are utilized, and the accompanying drawings.

Although the detailed description contains many specifics, these should not be construed as limiting the scope of the disclosure but merely as illustrating different examples and aspects of the present disclosure. It should be appreciated that the scope of the disclosure includes other embodiments not discussed in detail above. Various other modifications, changes and variations which will be apparent to those skilled in the art may be made in the arrangement, operation and details of the methods, systems, and apparatus of the present disclosure provided herein without departing from the spirit and scope of the invention as described herein.

As used herein the terms "dental appliance," and "tooth receiving appliance" are treated synonymously. As used herein, a "dental positioning appliance" or an "orthodontic appliance" may be treated synonymously, and may include any dental appliance configured to change the position of a patient's teeth in accordance with a plan, such as an orthodontic treatment plan. A "dental positioning appliance" or "orthodontic appliance," as used herein, may include a set of dental appliances configured to incrementally change the position of a patient's teeth over time. As noted herein, dental positioning appliances and/or orthodontic appliances may comprise polymeric appliances configured to move a patient's teeth in accordance with an orthodontic treatment plan.

As used herein the term "and/or" may be used as a functional word to indicate that two words or expressions are to be taken together or individually. For example, the phrase "A and/or B" encompasses A alone, B alone, and A and B together. Depending on context, the term "or" need not exclude one of a plurality of words/expressions. As an example, the phrase "A or B" need not exclude A and B together.

As used herein the terms "torque" and "moment" are treated synonymously.

As used herein a "moment" may encompass a force acting on an object such as a tooth at a distance from a center of resistance. The moment may be calculated with a vector cross product of a vector force applied to a location corresponding to a displacement vector from the center of resistance, for example. The moment may comprise a vector pointing in a direction. A moment opposing another moment may encompass one of the moment vectors oriented toward a first side of the object such as the tooth and the other moment vector oriented toward an opposite side of the object such as tooth, for example. Any discussion herein referring to application of forces on a patient's teeth is equally applicable to application of moments on the teeth, and vice-versa.

As used herein a "plurality of teeth" may encompass two or more teeth. A plurality of teeth may, but need not, comprise adjacent teeth. In some embodiments, one or more posterior teeth comprises one or more of a molar, a premolar or a canine, and one or more anterior teeth comprising one or more of a central incisor, a lateral incisor, a cuspid, a first bicuspid or a second bicuspid.

The embodiments disclosed herein may be well suited for moving one or more teeth of the first group of one or more teeth or moving one or more of the second group of one or more teeth, and combinations thereof.

The embodiments disclosed herein may be well suited for combination with one or more commercially available tooth moving components such as attachments and polymeric shell appliances. In some embodiments, the appliance and one or more attachments are configured to move one or more teeth along a tooth movement vector comprising six degrees of freedom, in which three degrees of freedom are rotational and three degrees of freedom are translation.

The present disclosure provides orthodontic appliances and related systems, methods, and devices. Repositioning of teeth may be accomplished with the use of a series of removable elastic positioning appliances such as the Invisalign® system available from Align Technology, Inc., the assignee of the present disclosure. Such appliances may have a thin shell of elastic material that generally conforms to a patient's teeth but is slightly out of alignment with an initial or immediately prior tooth configuration. Placement of the appliance over the teeth applies controlled forces in specific locations to gradually move the teeth into the new configuration. Repetition of this process with successive appliances comprising new configurations eventually moves the teeth through a series of intermediate configurations or alignment patterns to a final desired configuration. Repositioning of teeth may be accomplished through other series of removable orthodontic and/or dental appliances, including polymeric shell appliances.

Although reference is made to an appliance comprising a polymeric shell appliance, the embodiments disclosed herein are well suited for use with many appliances that receive teeth, for example appliances without one or more of polymers or shells. The appliance can be fabricated with one or more of many materials such as metal, glass, reinforced fibers, carbon fiber, composites, reinforced composites, aluminum, biological materials, and combinations thereof for example. The appliance can be shaped in many ways, such as with thermoforming or direct fabrication as described herein, for example. Alternatively or in combination, the appliance can be fabricated with machining such as an appliance fabricated from a block of material with computer numeric control machining. Additionally, though reference is made herein to orthodontic appliances, at least some of the techniques described herein may apply to restorative and/or other dental appliances, including without limitation crowns, veneers, teeth-whitening appliances, teeth-protective appliances, etc.

Turning now to the drawings, in which like numbers designate like elements in the various figures, FIG. 1A illustrates an exemplary tooth repositioning appliance or aligner 100 that can be worn by a patient in order to achieve an incremental repositioning of individual teeth 102 in the jaw. The appliance can include a shell (e.g., a continuous polymeric shell or a segmented shell) having teeth-receiving cavities that receive and resiliently reposition the teeth. An appliance or portion(s) thereof may be indirectly fabricated using a physical model of teeth. For example, an appliance (e.g., polymeric appliance) can be formed using a physical model of teeth and a sheet of suitable layers of polymeric material. The physical model (e.g., physical mold) of teeth can be formed through a variety of techniques, including 3D printing. The appliance can be formed by thermoforming the appliance over the physical model. In some embodiments, a physical appliance is directly fabricated, e.g., using additive manufacturing techniques, from a digital model of an appliance. In some embodiments, the physical appliance may be created through a variety of direct formation techniques, such as 3D printing. An appliance can fit over all teeth present in an upper or lower jaw, or less than all of the teeth. The appliance can be designed specifically to accommodate the teeth of the patient (e.g., the topography of the tooth-receiving cavities matches the topography of the patient's teeth), and may be fabricated based on positive or negative models of the patient's teeth generated by impression, scanning, and the like. Alternatively, the appliance can be a generic appliance configured to receive the teeth, but not necessarily shaped to match the topography of the patient's teeth. In some cases, only certain teeth received by an appliance will be repositioned by the appliance while other teeth can provide a base or anchor region for holding the appliance in place as it applies force against the tooth or teeth targeted for repositioning. In some cases, some or most, and even all, of the teeth will be repositioned at some point during treatment. Teeth that are moved can also serve as a base or anchor for holding the appliance as it is worn by the patient. In some embodiments, no wires or other means will be provided for holding an appliance in place over the teeth. In some cases, however, it may be desirable or necessary to provide individual attachments or other anchoring elements 104 on teeth 102 with corresponding receptacles or apertures 106 in the appliance 100 so that the appliance can apply a selected force on the tooth. Exemplary appliances, including those utilized in the Invisalign® System, are described in numerous patents and patent applications assigned to Align Technology, Inc. including, for example, in U.S. Pat. Nos. 6,450,807, and 5,975,893, as well as on the company's website, which is accessible on the World Wide Web (see, e.g., the url "invisalign.com"). Examples of tooth-mounted attachments suitable for use with orthodontic appliances are also described in patents and patent applications assigned to Align Technology, Inc., including, for example, U.S. Pat. Nos. 6,309,215 and 6,830,450.

Optionally, in cases involving more complex movements or treatment plans, it may be beneficial to utilize auxiliary components (e.g., features, accessories, structures, devices, components, and the like) in conjunction with an orthodontic appliance. Examples of such accessories include but are not limited to elastics, wires, springs, bars, arch expanders, palatal expanders, twin blocks, occlusal blocks, bite ramps, mandibular advancement splints, bite plates, pontics, hooks, brackets, headgear tubes, springs, bumper tubes, palatal bars, frameworks, pin-and-tube apparatuses, buccal shields, buccinator bows, wire shields, lingual flanges and pads, lip pads or bumpers, protrusions, divots, and the like. In some embodiments, the appliances, systems and methods described herein include improved orthodontic appliances with integrally formed features that are shaped to couple to such auxiliary components, or that replace such auxiliary components.

Figure 1B:
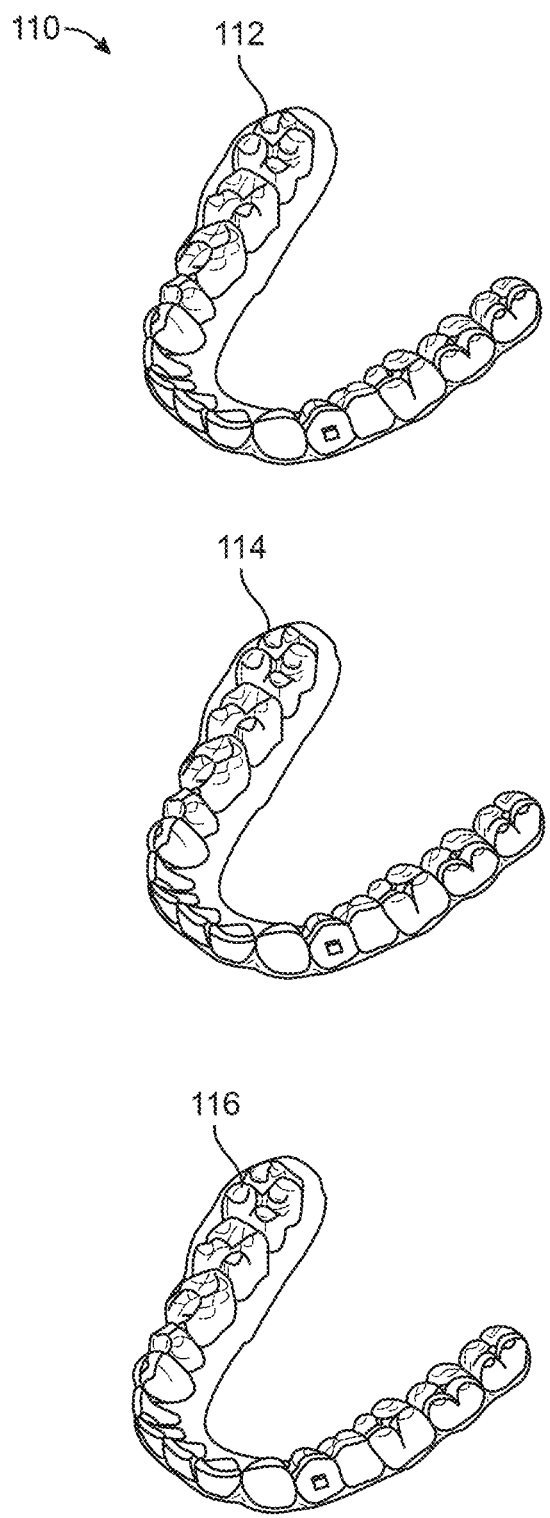
FIG. 1B illustrates a tooth repositioning system, in accordance with one or more embodiments herein.

FIG. 1B illustrates a tooth repositioning system 110 including a plurality of appliances 112, 114, 116. Any of the appliances described herein can be designed and/or provided as part of a set of a plurality of appliances used in a tooth repositioning system. Each appliance may be configured so a tooth-receiving cavity has a geometry corresponding to an intermediate or final tooth arrangement intended for the appliance. The patient's teeth can be progressively repositioned from an initial tooth arrangement towards a target tooth arrangement by placing a series of incremental position adjustment appliances over the patient's teeth. For example, the tooth repositioning system 110 can include a first appliance 112 corresponding to an initial tooth arrangement, one or more intermediate appliances 114 corresponding to one or more intermediate arrangements, and a final appliance 116 corresponding to a target arrangement. A target tooth arrangement can be a planned final tooth arrangement selected for the patient's teeth at the end of all planned orthodontic treatment. Alternatively, a target arrangement can be one of some intermediate arrangements for the patient's teeth during the course of orthodontic treatment, which may include various different treatment scenarios, including, but not limited to, instances where surgery is recommended, where interproximal reduction (IPR) is appropriate, where a progress check is scheduled, where anchor placement is best, where palatal expansion is desirable, where restorative dentistry is involved (e.g., inlays, onlays, crowns, bridges, implants, veneers, and the like), etc. As such, it is understood that a target tooth arrangement can be any planned resulting arrangement for the patient's teeth that follows one or more incremental repositioning stages. Likewise, an initial tooth arrangement can be any initial arrangement for the patient's teeth that is followed by one or more incremental repositioning stages.

Figure 1C:
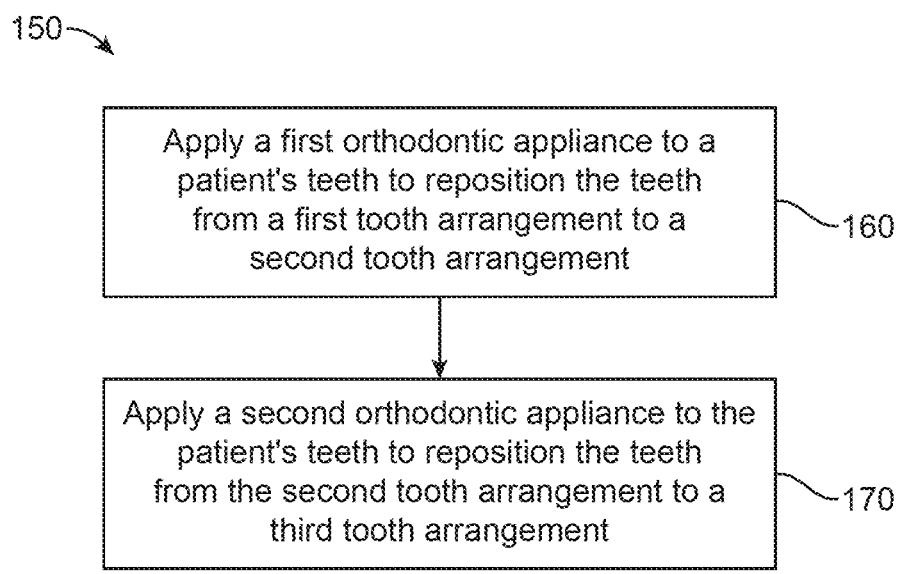
FIG. 1C illustrates a method of orthodontic treatment using a plurality of appliances, in accordance with one or more embodiments herein.

FIG. 1C illustrates a method 150 of orthodontic treatment using a plurality of appliances, in accordance with embodiments. The method 150 can be practiced using any of the appliances or appliance sets described herein. In block 160, a first orthodontic appliance is applied to a patient's teeth in order to reposition the teeth from a first tooth arrangement to a second tooth arrangement. In block 170, a second orthodontic appliance is applied to the patient's teeth in order to reposition the teeth from the second tooth arrangement to a third tooth arrangement. The method 150 can be repeated as necessary using any suitable number and combination of sequential appliances in order to incrementally reposition the patient's teeth from an initial arrangement to a target arrangement. The appliances can be generated all at the same stage or in sets or batches (at the beginning of a stage of the treatment, at an intermediate stage of treatment, etc.), or the appliances can be fabricated one at a time, and the patient can wear each appliance until the pressure of each appliance on the teeth can no longer be felt or until the maximum amount of expressed tooth movement for that given stage has been achieved. A plurality of different appliances (e.g., a set) can be designed and even fabricated prior to the patient wearing any appliance of the plurality. After wearing an appliance for an appropriate period of time, the patient can replace the current appliance with the next appliance in the series until no more appliances remain. The appliances are generally not affixed to the teeth and the patient may place and replace the appliances at any time during the procedure (e.g., patient-removable appliances). The final appliance or several appliances in the series may have a geometry or geometries selected to overcorrect the tooth arrangement. For instance, one or more appliances may have a geometry that would (if fully achieved) move individual teeth beyond the tooth arrangement that has been selected as the "final." Such over-correction may be desirable in order to offset potential relapse after the repositioning method has been terminated (e.g., permit movement of individual teeth back toward their pre-corrected positions). Over-correction may also be beneficial to speed the rate of correction (e.g., an appliance with a geometry that is positioned beyond a desired intermediate or final position may shift the individual teeth toward the position at a greater rate). In such cases, the use of an appliance can be terminated before the teeth reach the positions defined by the appliance. Furthermore, over-correction may be deliberately applied in order to compensate for any inaccuracies or limitations of the appliance.

The various embodiments of the orthodontic appliances presented herein can be fabricated in a wide variety of ways. In some embodiments, the orthodontic appliances herein (or portions thereof) can be produced using direct fabrication, such as additive manufacturing techniques (also referred to herein as "3D printing) or subtractive manufacturing techniques (e.g., milling). In some embodiments, direct fabrication involves forming an object (e.g., an orthodontic appliance or a portion thereof) without using a physical template (e.g., mold, mask etc.) to define the object geometry. Additive manufacturing techniques can be categorized as follows: (1) vat photopolymerization (e.g., stereolithography), in which an object is constructed layer by layer from a vat of liquid photopolymer resin; (2) material jetting, in which material is jetted onto a build platform using either a continuous or drop on demand (DOD) approach; (3) binder jetting, in which alternating layers of a build material (e.g., a powder-based material) and a binding material (e.g., a liquid binder) are deposited by a print head; (4) fused deposition modeling (FDM), in which material is drawn though a nozzle, heated, and deposited layer by layer; (5) powder bed fusion, including but not limited to direct metal laser sintering (DMLS), electron beam melting (EBM), selective heat sintering (SHS), selective laser melting (SLM), and selective laser sintering (SLS); (6) sheet lamination, including but not limited to laminated object manufacturing (LOM) and ultrasonic additive manufacturing (UAM); and (7) directed energy deposition, including but not limited to laser engineering net shaping, directed light fabrication, direct metal deposition, and 3D laser cladding. For example, stereolithography can be used to directly fabricate one or more of the appliances herein. In some embodiments, stereolithography involves selective polymerization of a photosensitive resin (e.g., a photopolymer) according to a desired cross-sectional shape using light (e.g., ultraviolet light). The object geometry can be built up in a layer-by-layer fashion by sequentially polymerizing a plurality of object cross-sections. As another example, the appliances herein can be directly fabricated using selective laser sintering. In some embodiments, selective laser sintering involves using a laser beam to selectively melt and fuse a layer of powdered material according to a desired cross-sectional shape in order to build up the object geometry. As yet another example, the appliances herein can be directly fabricated by fused deposition modeling. In some embodiments, fused deposition modeling involves melting and selectively depositing a thin filament of thermoplastic polymer in a layer-by-layer manner in order to form an object. In yet another example, material jetting can be used to directly fabricate the appliances herein. In some embodiments, material jetting involves jetting or extruding one or more materials onto a build surface in order to form successive layers of the object geometry.

In some embodiments, the direct fabrication methods provided herein build up the object geometry in a layer-by-layer fashion, with successive layers being formed in discrete build steps. Alternatively or in combination, direct fabrication methods that allow for continuous build-up of an object's geometry can be used, referred to herein as "continuous direct fabrication." Various types of continuous direct fabrication methods can be used. As an example, in some embodiments, the appliances herein are fabricated using "continuous liquid interphase printing," in which an object is continuously built up from a reservoir of photopolymerizable resin by forming a gradient of partially cured resin between the building surface of the object and a polymerization-inhibited "dead zone." In some embodiments, a semi-permeable membrane is used to control transport of a photopolymerization inhibitor (e.g., oxygen) into the dead zone in order to form the polymerization gradient. Continuous liquid interphase printing can achieve fabrication speeds about 25 times to about 100 times faster than other direct fabrication methods, and speeds about 1000 times faster can be achieved with the incorporation of cooling systems. Continuous liquid interphase printing is described in U.S. Patent Publication Nos. 2015/0097315, 2015/0097316, and 2015/0102532, (corresponding to U.S. Patent Nos. corresponding to U.S. Pat. Nos. 9,205,601, 9,216,546, and 9,211,678) the disclosures of each of which are incorporated herein by reference in their entirety.

As another example, a continuous direct fabrication method can achieve continuous build-up of an object geometry by continuous movement of the build platform (e.g., along the vertical or Z-direction) during the irradiation phase, such that the hardening depth of the irradiated photopolymer is controlled by the movement speed. Accordingly, continuous polymerization of material on the build surface can be achieved. Such methods are described in U.S. Pat. No. 7,892,474, the disclosure of which is incorporated herein by reference in its entirety.

In another example, a continuous direct fabrication method can involve extruding a composite material composed of a curable liquid material surrounding a solid strand. The composite material can be extruded along a continuous 3D path in order to form the object. Such methods are described in U.S. Patent Publication No. 2014/0061974, corresponding to U.S. Pat. No. 9,511,543, the disclosures of which are incorporated herein by reference in its entirety.

In yet another example, a continuous direct fabrication method utilizes a "heliolithography" approach in which the liquid photopolymer is cured with focused radiation while the build platform is continuously rotated and raised. Accordingly, the object geometry can be continuously built up along a spiral build path. Such methods are described in U.S. Patent Publication No. 2014/0265034, corresponding to U.S. Pat. No. 9,321,215, the disclosures of which are incorporated herein by reference in its entirety.

The direct fabrication approaches provided herein are compatible with a wide variety of materials, including but not limited to one or more of the following: polymer matrix reinforced with ceramic or metallic polymers, a polyester, a co-polyester, a polycarbonate, a thermoplastic polyurethane, a polypropylene, a polyethylene, a polypropylene and polyethylene copolymer, an acrylic, a cyclic block copolymer, a polyetheretherketone, a polyamide, a polyethylene terephthalate, a polybutylene terephthalate, a polyetherimide, a polyethersulfone, a polytrimethylene terephthalate, a styrenic block copolymer (SBC), a silicone rubber, an elastomeric alloy, a thermoplastic elastomer (TPE), a thermoplastic vulcanizate (TPV) elastomer, a polyurethane elastomer, a block copolymer elastomer, a polyolefin blend elastomer, a thermoplastic co-polyester elastomer, a thermoplastic polyamide elastomer, or combinations thereof. The materials used for direct fabrication can be provided in an uncured form (e.g., as a liquid, resin, powder, etc.) and can be cured (e.g., by photopolymerization, light curing, gas curing, laser curing, crosslinking, etc.) in order to form an orthodontic appliance or a portion thereof. The properties of the material before curing may differ from the properties of the material after curing. Once cured, the materials herein can exhibit sufficient strength, stiffness, durability, biocompatibility, etc. for use in an orthodontic appliance. The post-curing properties of the materials used can be selected according to the desired properties for the corresponding portions of the appliance.

In some embodiments, relatively rigid portions of the orthodontic appliance can be formed via direct fabrication using one or more of the following materials: a polyester, a co-polyester, a polycarbonate, a thermoplastic polyurethane, a polypropylene, a polyethylene, a polypropylene and polyethylene copolymer, an acrylic, a cyclic block copolymer, a polyetheretherketone, a polyamide, a polyethylene terephthalate, a polybutylene terephthalate, a polyetherimide, a polyethersulfone, and/or a polytrimethylene terephthalate.

In some embodiments, relatively elastic portions of the orthodontic appliance can be formed via direct fabrication using one or more of the following materials: a styrenic block copolymer (SBC), a silicone rubber, an elastomeric alloy, a thermoplastic elastomer (TPE), a thermoplastic vulcanizate (TPV) elastomer, a polyurethane elastomer, a block copolymer elastomer, a polyolefin blend elastomer, a thermoplastic co-polyester elastomer, and/or a thermoplastic polyamide elastomer.

Optionally, the direct fabrication methods described herein allow for fabrication of an appliance including multiple materials, referred to herein as "multi-material direct fabrication." In some embodiments, a multi-material direct fabrication method involves concurrently forming an object from multiple materials in a single manufacturing step using the same fabrication machine and method. For instance, a multi-tip extrusion apparatus can be used to selectively dispense multiple types of materials (e.g., resins, liquids, solids, or combinations thereof) from distinct material supply sources in order to fabricate an object from a plurality of different materials. Such methods are described in U.S. Pat. No. 6,749,414, the disclosure of which is incorporated herein by reference in its entirety. Alternatively or in combination, a multi-material direct fabrication method can involve forming an object from multiple materials in a plurality of sequential manufacturing steps. For instance, a first portion of the object can be formed from a first material in accordance with any of the direct fabrication methods herein, then a second portion of the object can be formed from a second material in accordance with methods herein, and so on, until the entirety of the object has been formed. The relative arrangement of the first and second portions can be varied as desired, e.g., the first portion can be partially or wholly encapsulated by the second portion of the object. The sequential manufacturing steps can be performed using the same fabrication machine or different fabrication machines, and can be performed using the same fabrication method or different fabrication methods. For example, a sequential multi-manufacturing procedure can involve forming a first portion of the object using stereolithography and a second portion of the object using fused deposition modeling.

Direct fabrication can provide various advantages compared to other manufacturing approaches. For instance, in contrast to indirect fabrication, direct fabrication permits production of an orthodontic appliance without utilizing any molds or templates for shaping the appliance, thus reducing the number of manufacturing steps involved and improving the resolution and accuracy of the final appliance geometry. Additionally, direct fabrication permits precise control over the 3D geometry of the appliance, such as the appliance thickness. Complex structures and/or auxiliary components can be formed integrally as a single piece with the appliance shell in a single manufacturing step, rather than being added to the shell in a separate manufacturing step. In some embodiments, direct fabrication is used to produce appliance geometries that would be difficult to create using alternative manufacturing techniques, such as appliances with very small or fine features, complex geometric shapes, undercuts, interproximal structures, shells with variable thicknesses, and/or internal structures (e.g., for improving strength with reduced weight and material usage). For example, in some embodiments, the direct fabrication approaches herein permit fabrication of an orthodontic appliance with feature sizes of less than or equal to about 5 µm, or within a range from about 5 µm to about 50 µm, or within a range from about 20 µm to about 50 µm.

In some embodiments, the direct fabrication methods described herein implement process controls for various machine parameters of a direct fabrication system or device in order to ensure that the resultant appliances are fabricated with a high degree of precision. Such precision can be beneficial for ensuring accurate delivery of a desired force system to the teeth in order to effectively elicit tooth movements. Process controls can be implemented to account for process variability arising from multiple sources, such as the material properties, machine parameters, environmental variables, and/or post-processing parameters.

Material properties may vary depending on the properties of raw materials, purity of raw materials, and/or process variables during mixing of the raw materials. In many embodiments, resins or other materials for direct fabrication should be manufactured with tight process control to ensure little variability in photo-characteristics, material properties (e.g., viscosity, surface tension), physical properties (e.g., modulus, strength, elongation) and/or thermal properties (e.g., glass transition temperature, heat deflection temperature). Process control for a material manufacturing process can be achieved with screening of raw materials for physical properties and/or control of temperature, humidity, and/or other process parameters during the mixing process. By implementing process controls for the material manufacturing procedure, reduced variability of process parameters and more uniform material properties for each batch of material can be achieved. Residual variability in material properties can be compensated with process control on the machine, as discussed further herein.

Machine parameters can include curing parameters. For digital light processing (DLP)-based curing systems, curing parameters can include power, curing time, and/or grayscale of the full image. For laser-based curing systems, curing parameters can include power, speed, beam size, beam shape and/or power distribution of the beam. For printing systems, curing parameters can include material drop size, viscosity, and/or curing power. These machine parameters can be monitored and adjusted on a regular basis (e.g., some parameters at every 1-x layers and some parameters after each build) as part of the process control on the fabrication machine. Process control can be achieved by including a sensor on the machine that measures power and other beam parameters every layer or every few seconds and automatically adjusts them with a feedback loop. For DLP machines, gray scale can be measured and calibrated before, during, and/or at the end of each build, and/or at predetermined time intervals (e.g., every $n^{th}$ build, once per hour, once per day, once per week, etc.), depending on the stability of the system. In addition, material properties and/or photo-characteristics can be provided to the fabrication machine, and a machine process control module can use these parameters to adjust machine parameters (e.g., power, time, gray scale, etc.) to compensate for variability in material properties. By implementing process controls for the fabrication machine, reduced variability in appliance accuracy and residual stress can be achieved.

In many embodiments, environmental variables (e.g., temperature, humidity, Sunlight or exposure to other energy/curing source) are maintained in a tight range to reduce variable in appliance thickness and/or other properties. Optionally, machine parameters can be adjusted to compensate for environmental variables.

In many embodiments, post-processing of appliances includes cleaning, post-curing, and/or support removal processes. Relevant post-processing parameters can include purity of cleaning agent, cleaning pressure and/or temperature, cleaning time, post-curing energy and/or time, and/or consistency of support removal process. These parameters can be measured and adjusted as part of a process control scheme. In addition, appliance physical properties can be varied by modifying the post-processing parameters. Adjusting post-processing machine parameters can provide another way to compensate for variability in material properties and/or machine properties.

Although various embodiments herein are described with respect to direct fabrication techniques, it shall be appreciated that other techniques can also be used, such as indirect fabrication techniques. In some embodiments, the appliances herein (or portions thereof) can be produced using indirect fabrication techniques, such as by thermoforming over a positive or negative mold. Indirect fabrication of an orthodontic appliance can involve one or more of the following steps: producing a positive or negative mold of the patient's dentition in a target arrangement (e.g., by additive manufacturing, milling, etc.), thermoforming one or more sheets of material over the mold in order to generate an appliance shell, forming one or more structures in the shell (e.g., by cutting, etching, etc.), and/or coupling one or more components to the shell (e.g., by extrusion, additive manufacturing, spraying, thermoforming, adhesives, bonding, fasteners, etc.). Optionally, one or more auxiliary appliance components as described herein (e.g., elastics, wires, springs, bars, arch expanders, palatal expanders, twin blocks, occlusal blocks, bite ramps, mandibular advancement splints, bite plates, pontics, hooks, brackets, headgear tubes, bumper tubes, palatal bars, frameworks, pin-and-tube apparatuses, buccal shields, buccinator bows, wire shields, lingual flanges and pads, lip pads or bumpers, protrusions, divots, etc.) are formed separately from and coupled to the appliance shell (e.g., via adhesives, bonding, fasteners, mounting features, etc.) after the shell has been fabricated.

In some embodiments, the orthodontic appliances herein can be fabricated using a combination of direct and indirect fabrication techniques, such that different portions of an appliance can be fabricated using different fabrication techniques and assembled in order to form the final appliance. For example, an appliance shell can be formed by indirect fabrication (e.g., thermoforming), and one or more structures or components as described herein (e.g., auxiliary components, power arms, etc.) can be added to the shell by direct fabrication (e.g., printing onto the shell).

The configuration of the orthodontic appliances herein can be determined according to a treatment plan for a patient, e.g., a treatment plan involving successive administration of a plurality of appliances for incrementally repositioning teeth. Computer-based treatment planning and/or appliance manufacturing methods can be used in order to facilitate the design and fabrication of appliances. For instance, one or more of the appliance components described herein can be digitally designed and fabricated with the aid of computer-controlled manufacturing devices (e.g., computer numerical control (CNC) milling, computer-controlled additive manufacturing such as 3D printing, etc.). The computer-based methods presented herein can improve the accuracy, flexibility, and convenience of appliance fabrication.

In some embodiments, computer-based 3D planning/design tools, such as Treat™ software from Align Technology, Inc., may be used to design and fabricate the orthodontic appliances described herein.

Figure 2:
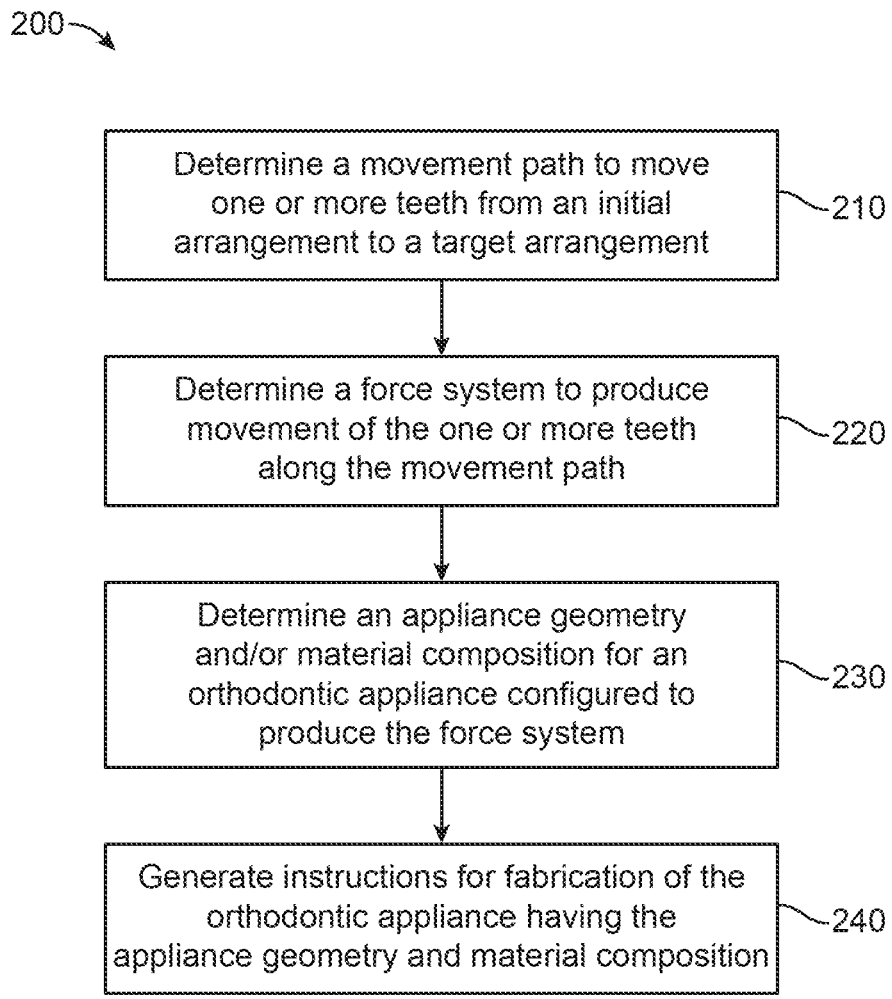
FIG. 2 illustrates a method for designing an orthodontic appliance, in accordance with one or more embodiments herein.

FIG. 2 illustrates a method 200 for designing an orthodontic appliance to be fabricated, in accordance with embodiments. The method 200 can be applied to any embodiment of the orthodontic appliances described herein. Some or all of the operations of the method 200 can be performed by any suitable data processing system or device, e.g., one or more processors configured with suitable instructions.

In block 210, a movement path to move one or more teeth from an initial arrangement to a target arrangement is determined. The initial arrangement can be determined from a mold or a scan of the patient's teeth or mouth tissue, e.g., using wax bites, direct contact scanning, x-ray imaging, tomographic imaging, sonographic imaging, and other techniques for obtaining information about the position and structure of the teeth, jaws, gums and other orthodontically relevant tissue. From the obtained data, a digital data set can be derived that represents the initial (e.g., pretreatment) arrangement of the patient's teeth and other tissues. Optionally, the initial digital data set is processed to segment the tissue constituents from each other. For example, data structures that digitally represent individual tooth crowns can be produced. Advantageously, digital models of entire teeth can be produced, including measured or extrapolated hidden surfaces and root structures, as well as surrounding bone and soft tissue.

The target arrangement of the teeth (e.g., a desired and intended end result of orthodontic treatment) can be received from a clinician in the form of a prescription, can be calculated from basic orthodontic principles, and/or can be extrapolated computationally from a clinical prescription. With a specification of the desired final positions of the teeth and a digital representation of the teeth themselves, the final position and surface geometry of each tooth can be specified to form a complete model of the tooth arrangement at the desired end of treatment.

Having both an initial position and a target position for each tooth, a movement path can be defined for the motion of each tooth. In some embodiments, the movement paths are configured to move the teeth in the quickest fashion with the least amount of round-tripping to bring the teeth from their initial positions to their desired target positions. The tooth paths can optionally be segmented, and the segments can be calculated so that each tooth's motion within a segment stays within threshold limits of linear and rotational translation. In this way, the end points of each path segment can constitute a clinically viable repositioning, and the aggregate of segment end points can constitute a clinically viable sequence of tooth positions, so that moving from one point to the next in the sequence does not result in a collision of teeth.

In block 220, a force system to produce movement of the one or more teeth along the movement path is determined. A force system can include one or more forces and/or one or more torques. Different force systems can result in different types of tooth movement, such as tipping, translation, rotation, extrusion, intrusion, root movement, etc. Biomechanical principles, modeling techniques, force calculation/measurement techniques, and the like, including knowledge and approaches commonly used in orthodontia, may be used to determine the appropriate force system to be applied to the tooth to accomplish the tooth movement. In determining the force system to be applied, sources may be considered including literature, force systems determined by experimentation or virtual modeling, computer-based modeling, clinical experience, minimization of unwanted forces, etc.

Determination of the force system can be performed in a variety of ways. For example, in some embodiments, the force system is determined on a patient-by-patient basis, e.g., using patient-specific data. Alternatively or in combination, the force system can be determined based on a generalized model of tooth movement (e.g., based on experimentation, modeling, clinical data, etc.), such that patient-specific data is not necessarily used. In some embodiments, determination of a force system involves calculating specific force values to be applied to one or more teeth to produce a particular movement. Alternatively, determination of a force system can be performed at a high level without calculating specific force values for the teeth. For instance, block 220 can involve determining a particular type of force to be applied (e.g., extrusive force, intrusive force, translational force, rotational force, tipping force, torqueing force, etc.) without calculating the specific magnitude and/or direction of the force.

In block 230, an appliance geometry and/or material composition for an orthodontic appliance configured to produce the force system is determined. The appliance can be any embodiment of the appliances discussed herein, such as an appliance having variable localized properties, integrally formed components, and/or power arms.

For example, in some embodiments, the appliance comprises a heterogeneous thickness, a heterogeneous stiffness, or a heterogeneous material composition. In some embodiments, the appliance comprises two or more of a heterogeneous thickness, a heterogeneous stiffness, or a heterogeneous material composition. In some embodiments, the appliance comprises a heterogeneous thickness, a heterogeneous stiffness, and a heterogeneous material composition. The heterogeneous thickness, stiffness, and/or material composition can be configured to produce the force system for moving the teeth, e.g., by preferentially applying forces at certain locations on the teeth. For example, an appliance with heterogeneous thickness can include thicker portions that apply more force on the teeth than thinner portions. As another example, an appliance with heterogeneous stiffness can include stiffer portions that apply more force on the teeth than more elastic portions. Variations in stiffness can be achieved by varying the appliance thickness, material composition, and/or degree of photopolymerization, as described herein.

In some embodiments, determining the appliance geometry and/or material composition comprises determining the geometry and/or material composition of one or more integrally formed components to be directly fabricated with an appliance shell. The integrally formed component can be any of the embodiments described herein. The geometry and/or material composition of the integrally formed component(s) can be selected to facilitate application of the force system onto the patient's teeth. The material composition of the integrally formed component can be the same as or different from the material composition of the shell.

In some embodiments, determining the appliance geometry comprises determining the geometry for a variable gable bend.

The block 230 can involve analyzing the desired force system in order to determine an appliance geometry and material composition that would produce the force system. In some embodiments, the analysis involves determining appliance properties (e.g., stiffness) at one or more locations that would produce a desired force at the one or more locations. The analysis can then involve determining an appliance geometry and material composition at the one or more locations to achieve the specified properties. Determination of the appliance geometry and material composition can be performed using a treatment or force application simulation environment. A simulation environment can include, e.g., computer modeling systems, biomechanical systems or apparatus, and the like. Optionally, digital models of the appliance and/or teeth can be produced, such as finite element models. The finite element models can be created using computer program application software available from a variety of vendors. For creating solid geometry models, computer aided engineering (CAE) or computer aided design (CAD) programs can be used, such as the Auto-CAD® software products available from Autodesk, Inc., of San Rafael, Calif. For creating finite element models and analyzing them, program products from a number of vendors can be used, including finite element analysis packages from ANSYS, Inc., of Canonsburg, Pa., and SIMULIA (Abaqus) software products from Dassault Systèmes of Waltham, Mass.

Optionally, one or more appliance geometries and material compositions can be selected for testing or force modeling. As noted above, a desired tooth movement, as well as a force system required or desired for eliciting the desired tooth movement, can be identified. Using the simulation environment, a candidate appliance geometry and composition can be analyzed or modeled for determination of an actual force system resulting from use of the candidate appliance. One or more modifications can optionally be made to a candidate appliance, and force modeling can be further analyzed as described, e.g., in order to iteratively determine an appliance design that produces the desired force system.

Optionally, block 230 can further involve determining the geometry of one or more auxiliary components to be used in combination with the orthodontic appliance in order to exert the force system on the one or more teeth. Such auxiliaries can include one or more of tooth-mounted attachments, elastics, wires, springs, bite blocks, arch expanders, wire-and-bracket appliances, shell appliances, headgear, or any other orthodontic device or system that can be used in conjunction with the orthodontic appliances herein. The use of such auxiliary components may be advantageous in situations where it is difficult for the appliance alone to produce the force system. Additionally, auxiliary components can be added to the orthodontic appliance in order to provide other desired functionalities besides producing the force system, such as mandibular advancement splints to treat sleep apnea, pontics to improve aesthetic appearance, and so on. In some embodiments, the auxiliary components are fabricated and provided separately from the orthodontic appliance. Alternatively, the geometry of the orthodontic appliance can be modified to include one or more auxiliary components as integrally formed components.

In block 240, instructions for fabrication of the orthodontic appliance having the appliance geometry and material composition are generated. The instructions can be configured to control a fabrication system or device in order to produce the orthodontic appliance with the specified appliance geometry and material composition. In some embodiments, the instructions are configured for manufacturing the orthodontic appliance using direct fabrication (e.g., stereolithography, selective laser sintering, fused deposition modeling, 3D printing, continuous direct fabrication, multi-material direct fabrication, etc.). Optionally, the instructions can be configured to cause a fabrication machine to directly fabricate the orthodontic appliance with teeth receiving cavities having variable gable bends, as discussed above and herein. In alternative embodiments, the instructions can be configured for indirect fabrication of the appliance, e.g., by thermoforming.

Although the above blocks show a method 200 of designing an orthodontic appliance in accordance with some embodiments, a person of ordinary skill in the art will recognize some variations based on the teaching described herein. Some of the blocks may comprise sub-blocks. Some of the blocks may be repeated as often as desired. One or more blocks of the method 200 may be performed with any suitable fabrication system or device, such as the embodiments described herein. Some of the blocks may be optional, and the order of the blocks can be varied as desired. For instance, in some embodiments, block 220 is optional, such that block 230 involves determining the appliance geometry and/or material composition based directly on the tooth movement path rather than based on the force system.

Figure 3:
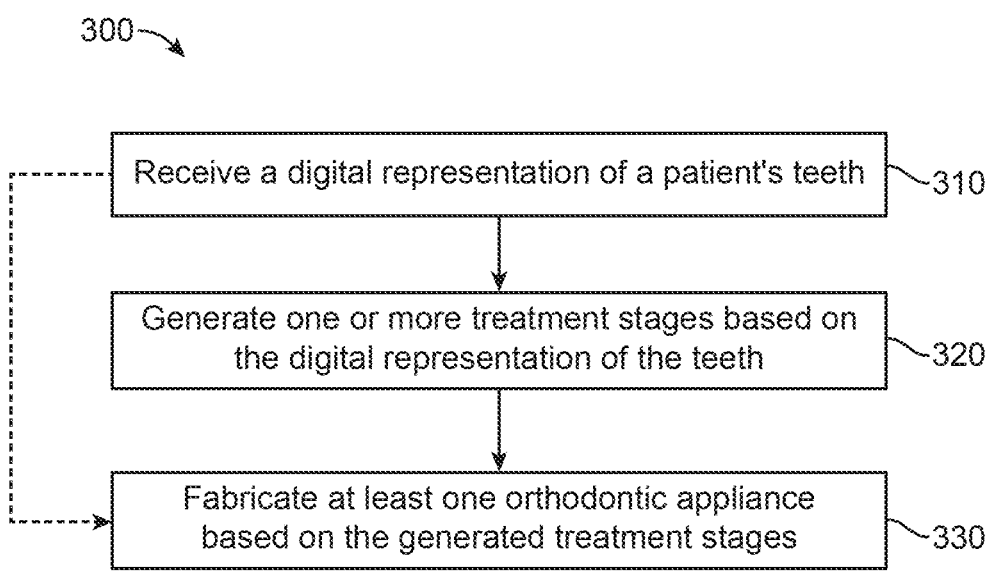
FIG. 3 illustrates a method for planning an orthodontic treatment, in accordance with one or more embodiments herein.

FIG. 3 illustrates a method 300 for digitally planning an orthodontic treatment and/or design or fabrication of an appliance, in accordance with embodiments. The method 300 can be applied to any of the treatment procedures described herein and can be performed by any suitable data processing system.

In block 310, a digital representation of a patient's teeth is received. The digital representation can include surface topography data for the patient's intraoral cavity (including teeth, gingival tissues, etc.). The surface topography data can be generated by directly scanning the intraoral cavity, a physical model (positive or negative) of the intraoral cavity, or an impression of the intraoral cavity, using a suitable scanning device (e.g., a handheld scanner, desktop scanner, etc.).

In block 320, one or more treatment stages are generated based on the digital representation of the teeth. The treatment stages can be incremental repositioning stages of an orthodontic treatment procedure designed to move one or more of the patient's teeth from an initial tooth arrangement to a target arrangement. For example, the treatment stages can be generated by determining the initial tooth arrangement indicated by the digital representation, determining a target tooth arrangement, and determining movement paths of one or more teeth in the initial arrangement necessary to achieve the target tooth arrangement. The movement path can be optimized based on minimizing the total distance moved, preventing collisions between teeth, avoiding tooth movements that are more difficult to achieve, or any other suitable criteria.

In block 330, at least one orthodontic appliance is fabricated based on the generated treatment stages. For example, a set of appliances can be fabricated, each shaped according to a tooth arrangement specified by one of the treatment stages, such that the appliances can be sequentially worn by the patient to incrementally reposition the teeth from the initial arrangement to the target arrangement. The appliance set may include one or more of the orthodontic appliances described herein. The fabrication of the appliance may involve creating a digital model of the appliance to be used as input to a computer-controlled fabrication system. The appliance can be formed using direct fabrication methods, indirect fabrication methods, or combinations thereof, as desired.

In some instances, staging of various arrangements or treatment stages may not be necessary for design and/or fabrication of an appliance. As illustrated by the dashed line in FIG. 3, design and/or fabrication of an orthodontic appliance, and perhaps a particular orthodontic treatment, may include use of a representation of the patient's teeth (e.g., receive a digital representation of the patient's teeth 310), followed by design and/or fabrication of an orthodontic appliance based on a representation of the patient's teeth in the arrangement represented by the received representation.

Optionally, some or all of the blocks of the method 300 are performed locally at the site where the patient is being treated and during a single patient visit, referred to herein as "chair side manufacturing." Chair side manufacturing can involve, for example, scanning the patient's teeth, automatically generating a treatment plan with treatment stages, and immediately fabricating one or more orthodontic appliance(s) to treat the patient using a chair side direct fabrication machine, all at the treating professional's office during a single appointment. In embodiments where a series of appliances are used to treat the patient, the first appliance may be produced chair side for immediate delivery to the patient, with the remaining appliances produced separately (e.g., off site at a lab or central manufacturing facility) and delivered at a later time (e.g., at a follow up appointment, mailed to the patient). Alternatively, the methods herein can accommodate production and immediate delivery of the entire series of appliances on site during a single visit. Chair side manufacturing can thus improve the convenience and speed of the treatment procedure by allowing the patient to immediately begin treatment at the practitioner's office, rather than having to wait for fabrication and delivery of the appliances at a later date. Additionally, chair side manufacturing can provide improved flexibility and efficiency of orthodontic treatment. For instance, in some embodiments, the patient is re-scanned at each appointment to determine the actual positions of the teeth, and the treatment plan is updated accordingly. Subsequently, new appliances can be immediately produced and delivered chair side to accommodate any changes to or deviations from the treatment plan.

Figure 4:
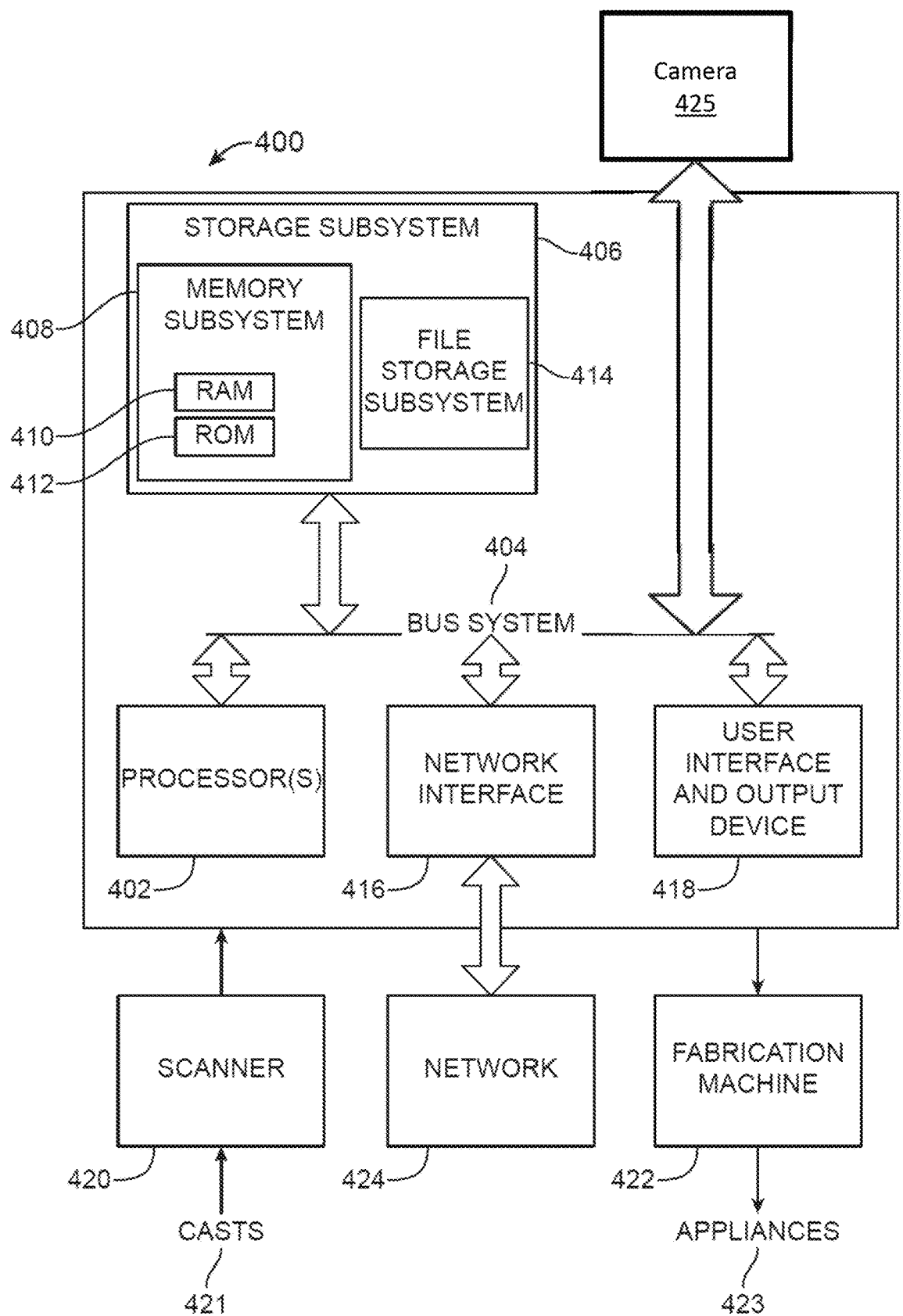
FIG. 4 is a simplified block diagram of a system for designing an orthodontic appliance and planning an orthodontic treatment, in accordance with one or more embodiments herein.

FIG. 4 is a simplified block diagram of a data processing system 400 that may be used in executing methods and processes described herein. The data processing system 400 typically includes at least one processor 402 that communicates with one or more peripheral devices via bus subsystem 404. These peripheral devices typically include a storage subsystem 406 (memory subsystem 408 and file storage subsystem 414), a set of user interface input and output devices 418, and an interface to outside networks 416. This interface is shown schematically as "Network Interface" block 416, and is coupled to corresponding interface devices in other data processing systems via communication network interface 424. Data processing system 400 can include, for example, one or more computers, such as a personal computer, workstation, mainframe, laptop, and the like.

The user interface input devices 418 are not limited to any particular device, and can typically include, for example, a keyboard, pointing device, mouse, scanner, interactive displays, touchpad, joysticks, etc. Similarly, various user interface output devices can be employed in a system of the invention, and can include, for example, one or more of a printer, display (e.g., visual, non-visual) system/subsystem, controller, projection device, audio output, and the like.

Storage subsystem 406 maintains the basic required programming, including computer readable media having instructions (e.g., operating instructions, etc.), and data constructs. The program modules discussed herein are typically stored in storage subsystem 406. Storage subsystem 406 typically includes memory subsystem 408 and file storage subsystem 414. Memory subsystem 408 typically includes a number of memories (e.g., RAM 410, ROM 412, etc.) including computer readable memory for storage of fixed instructions, instructions and data during program execution, basic input/output system, etc. File storage subsystem 414 provides persistent (non-volatile) storage for program and data files, and can include one or more removable or fixed drives or media, hard disk, floppy disk, CD-ROM, DVD, optical drives, and the like. One or more of the storage systems, drives, etc., may be located at a remote location, such coupled via a server on a network or via the internet/World Wide Web. In this context, the term "bus subsystem" is used generically so as to include any mechanism for letting the various components and subsystems communicate with each other as intended and can include a variety of suitable components/systems that would be known or recognized as suitable for use therein. It will be recognized that various components of the system can be, but need not necessarily be at the same physical location, but could be connected via various local-area or wide-area network media, transmission systems, etc.

Scanner 420 includes any means for obtaining a digital representation (e.g., images, surface topography data, etc.) of a patient's teeth (e.g., by scanning physical models of the teeth such as casts 421, by scanning impressions taken of the teeth, or by directly scanning the intraoral cavity), which can be obtained either from the patient or from treating professional, such as an orthodontist, and includes means of providing the digital representation to data processing system 400 for further processing. Scanner 420 may be located at a location remote with respect to other components of the system and can communicate image data and/or information to data processing system 400, for example, via a network interface 424. Fabrication system 422 fabricates appliances 423 based on a treatment plan, including data set information received from data processing system 400. Fabrication machine 422 can, for example, be located at a remote location and receive data set information from data processing system 400 via network interface 424. The camera 425 may include any image capture device configured to capture still images or movies. The camera 425 may facilitate capturing various perspectives of a patient's dentition. In some implementations, the camera 425 may facilitate capture of images at various focal lengths and distances from the patient.

The data processing aspects of the methods described herein can be implemented in digital electronic circuitry, or in computer hardware, firmware, software, or suitable combinations thereof. Data processing apparatus can be implemented in a computer program product tangibly embodied in a machine-readable storage device for execution by a programmable processor. Data processing blocks can be performed by a programmable processor executing program instructions to perform functions by operating on input data and generating output. The data processing aspects can be implemented in one or more computer programs that are executable on a programmable system, the system including one or more programmable processors operably coupled to a data storage system. Generally, a processor will receive instructions and data from a read-only memory and/or a random access memory. Storage devices suitable for tangibly embodying computer program instructions and data include all forms of nonvolatile memory, such as: semiconductor memory devices, such as EPROM, EEPROM, and flash memory devices; magnetic disks such as internal hard disks and removable disks; magneto-optical disks; and CD-ROM disks.

Forming a Photo-Realistic Composite Image of a Patient's Dentition

In some embodiments, one or more modules of the data processing system 400 may be configured to form a highly accurate composite image of a patient's dentition. As noted further herein, the processor(s) 402 may execute computer-implemented instructions stored on the storage subsystem 406 to gather a 3D model of a patient's dentition. The 3D model may include 3D virtual representations of a patient's dentition for display on a display device. In some implementations, the 3D model may facilitate modifications of parameters of teeth (locations, sizes, shapes, etc.) based on application of an orthodontic treatment plan. For instance, the 3D model may facilitate visualization of how a patient's teeth move and/or are represented after one or more orthodontic treatment plans have been applied to the patient's teeth. The processor(s) 402 may execute computer-implemented instructions stored on the storage subsystem 406 to gather an image of the patient that, in some embodiments, includes an image (e.g., a 2D image) of the patient's face and dentition. The image may have been captured with a camera, uploaded with a phone or computer, and/or uploaded over a network (e.g., the Internet).

In various implementations, the user interface and output device 418 may receive from a technician (e.g., a treatment professional) a first set of reference points corresponding to specific locations of the patient's dentition as represented on the 3D model of the patient's dentition. The first set of reference points may correspond to annotations, markups, drawn points, etc. placed on relevant anatomical points of the 3D model. The user interface and output device 148 may further receive from the technician a second set of reference points on a portion of the 2D image of the patient. In some implementations, the second set of reference points may correspond to annotations, markups, drawn points, etc. placed on parts of the 2D image that correspond to the relevant anatomical points identified by the first set of reference points on the 3D model.

In some implementations, the processor(s) 402 may execute program instructions stored on the storage subsystem(s) 408 that combine the 3D model of the patient's dentition with the image of the patient, particularly the dentition portion of the image of the patient. Such a combination may include identification of sizes, shapes, and/or perspectives of the various teeth modeled in the 3D model and/or represented in the image(s) of the patient's dentition. Combination may further include adjusting and/or scaling the models and/or representations of teeth so that specific parts of the 3D model have the same size/shape/perspective, etc. as similar parts of 2D images.

In some implementations, the processor(s) 402 may execute program instructions stored on the storage subsystem(s) 408 that align the first set of reference points on the 3D model with the second set of reference points on the image of the patient, particularly portions of the image of the patient corresponding to the patient's dentition. Alignment may involve adjusting the 3D model to the image so that the 3D model more accurately models the patient's dentition. In some implementations, the alignment involves mathematically correlating points on the 3D model with points on the image. As an example, the alignment may involve a statistical technique to ensure distances between the representations of the first set of reference points on the 3D model and the representations of the second set of reference points on the image are minimized and/or otherwise optimized. In various implementations, the alignment involves creating a projection plane in a 3D space using the image. The alignment, in such implementations, may further include minimizing the sum of squares of distances between corresponding points in the projection plane and the 3D model of the patient's dentition. Within the 3D model, the processor(s) 402 may execute program instructions stored on the storage subsystem(s) 408 to rotate and/or shift the 3D model of either jaw (mandible or maxilla) of a patient when the alignment is performed. Additionally, the processor(s) 402 may execute program instructions stored on the storage subsystem(s) 408 to change focal lengths, zooms, and/or other aspects of perspectives in the 3D model to facilitate visualization of a patient's dentition.

In some implementations, the processor(s) 402 may execute program instructions stored on the storage subsystem(s) 408 to display a modified 2D representation of a patient's dentition. In some implementations, the modified 2D representation may include estimated results of an orthodontic treatment plan. Rather than providing a computerized or otherwise non-human depiction of the application of the orthodontic treatment plan, the modified 2D representation may show a highly photo-realistic, emotion-evocative, humanistic visualization of how application of an orthodontic treatment plan will appear on the patient. Such a modified rendering may solve technical problems related to computerized visualization of treatment planning by use of automated image matching processes.

Figure 5A:
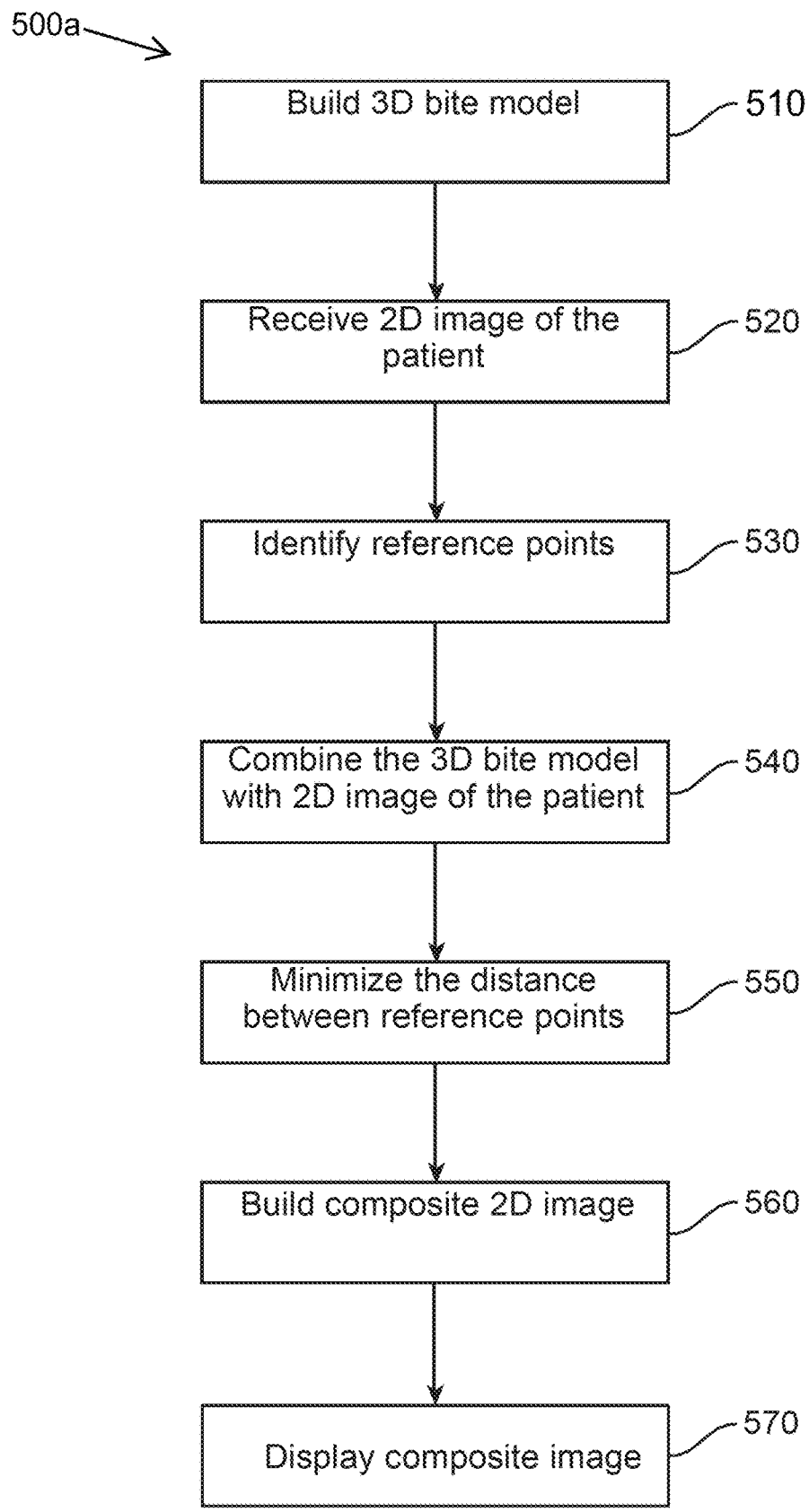
FIG. 5A depicts a method of building a composite image, in accordance with one or more embodiments herein.

FIG. 5A depicts a method 500*a* of building a composite image, in accordance with one or more embodiments herein. The method 500*a* may be used with or in the processes and/or systems described above with reference to FIGS. 1-4. A composite image, such as the composite image 600 (shown in FIG. 6), can be helpful in the treatment planning process and treatment of a patient. By integrating a 3D bite model into a 2D image of a patient, the dental professional can evaluate the final position of the teeth while taking into account facial features. A 3D bite model may be a 3D model of teeth, such as a patient's teeth. In addition, the treatment plan and proposed final or target position of the patient's teeth may be determined with the aid of the facial image of the patient, thereby creating a treatment plan that positions the teeth based on a final orthodontic position that corrects malocclusions and takes into account facial features, such as head shape, eye position, facial midline, and other facial features described herein.

To take into account the facial features of a patient, a composite image of the patient is formed using a 2D image of the face of the patient and a 3D bite model generated from a scan of the patient's mouth or of a positive of negative model of a patient's teeth and gums. The 3D bite model of the patient with the teeth in an initial position is integrated into the 2D image of the patient such that the teeth in the 3D bite model are placed in the same position at the teeth in the 2D image of the patient. At block 510 of method 500*a*, a 3D bite model of the patient's teeth is built. Such a model may be formed as described above with reference to FIGS. 1-4. The 3D bite model includes a model of the patient's teeth and gingiva in an initial position, such as before treatment, in a final or target position according to a treatment plan, or in an interim position that depicts the teeth and gums during the treatment process. The system 400 may build the 3D bite model.

At block 520 a 2D image of the patient is received. In some embodiments, the 2D image includes the mouth of the patient and one or more of the face, head, neck, shoulders, torso, or the entire patient. The 2D image of the patient may include an image of the patient with their mouth in one or more positions; for example, the patient's mouth may be a smiling position, such as a social smiling position, a repose position with relaxed muscles and lips slightly parted, or an anterior retracted open bite or closed bite positions.

In some embodiments, at block 520 an image of the patient is taken with a digital imaging device such as the camera 425. The image may be captured with a lens at a predetermined focal length and at a distance from the patient. The image may be captured remotely and then received for processing, for example, by the system 400 of FIG. 4.

At block 530 reference points are selected or otherwise identified on the 3D bite model and the 2D image of the patient. In some embodiments, the reference points may include the gingival apex of one or more teeth, such as the anterior teeth. In some embodiments, the reference points may include the midpoint of the incisal edge of the teeth or the ends of the incisal edges of teeth. In some embodiments, the reference points may be a cusp tip of one or more teeth, such as the cusp tips of the canine teeth. In some embodiments, facial landmarks and contours, selected using neural networks, or otherwise, as descried herein, may be used as reference points. Examples of reference points are further shown in FIGS. 7, 8, 9, 14 and 15 and discussed further herein.

The references points of the 3D bite model correspond to reference points at the same location in the 2D image. For example, the reference points include the gingival apex of each of the six anterior teeth on the 3D bite model and the reference points on the 2D image of the patient can also include the gingival apex of each of the six anterior teeth. Each of the reference points on a tooth or gingiva of the 3D bite model may correspond with a reference point on a tooth or gingiva of the 2D image. For example, a reference point at the left incisal gingival apex of the 3D bite model can correspond with the left incisal gingival apex of the 2D image of the patient. Such two corresponding reference points may be considered a pair of corresponding reference points.

At block 540 the 3D bite model is combined with the 2D image of the patient. The 3D bite model is manipulated and positioned such that the teeth of the 3D bite model are in the same position and the same size as the teeth of the patient in the 2D image.

In some embodiments, the 3D bite model is positioned in the 2D image by aligning each of the reference points on the 3D bite model to each of the corresponding reference points on the 2D image of the patient. In some embodiments, the reference points of the 3D bite model are aligned with the corresponding reference points on the 2D image of the patient by minimizing the sum of the distance between each corresponding pair of reference points. In some embodiments, the reference points of the 3D bite model are aligned with the corresponding reference points on the 2D image of the patient by minimizing the sum of the squares of the distance between each corresponding pair of reference points.

In some embodiments, combining the 3D bite model with the 2D image of the patient includes determining a mouth opening in the 2D image. In some embodiments, the mouth opening is the shape of the inside edge of the patient's lips in the 2D image. In some embodiments, the portion of the 2D image within the mouth opening is removed or otherwise deleted from the 2D image of the patient. In some embodiments, the 3D bite model, or a 2D projection of the 3D bite model is placed or rendered behind the 2D image such that the 3D bite model, or at least a portion of the 3D bite model, is visible through the mouth opening of the 2D image of the patient.

At block 550 the distance between one or more pairs of reference points or features is minimized. In some embodiments, the 3D bite model is rotated or translated about one or more of the three perpendicular axes of 3D space. In some embodiments, the size of the teeth relative to the 2D image may be selected by matching the distance and focal length of the rendering of the 3D bite model with focal length and the distance between the imaging device and the patient used when capturing the 2D image of the patient.

At block 560 the composite image is formed. In some embodiments, the composite image is a composite 2D image that integrates the 2D image of the patient and a 2D rendering of the 3D bite model, or at least a portion of the 3D bite model, viewable through the mouth opening of the 2D image. In some embodiments, the composite image is formed by displaying a 3D rendering of the 3D bite model, or at least a portion of the 3D bite model, behind and viewable through the mouth opening of the 2D image of the patient on a surface or on a monitor. In various implementations, the composite image comprises a modified 2D representation of a patient's dentition. In some implementations, the modified 2D representation may include estimated results of an orthodontic treatment plan. As noted herein, rather than providing a computerized or otherwise non-human depiction of the application of the orthodontic treatment plan, the modified 2D representation may show a highly photo-realistic, emotion-evocative, humanistic visualization of how application of an orthodontic treatment plan will appear on the patient. Such a modified rendering may solve technical problems related to computerized visualization of treatment planning by use of automated image matching processes.

At block 570, the composite image is displayed. The composite image may be displayed on a display device accessible to a patient locally, remotely, etc. In some implementations, the composite image is displayed remotely to the patient over a network connection (e.g., an Internet connection) on a digital device of the patient. The composite image may displayed in substantial real-time (e.g., while the patient is in the office and getting images of their dentition taken) or after a visit. In some implementations, the composite image is rendered into a format that can be displayed on a standalone application, a web page, a mobile application, and/or other portal for the patient.

FIG. 5B depicts a method 500b of building a composite image, in accordance with one or more embodiments herein. The method 500b may be used with or in the processes and/or systems described above with reference to FIGS. 1-4. A composite image, such as the composite image 600 (shown in FIG. 6), can be helpful in the treatment planning process and treatment of a patient. At an operation 582, a three-dimensional of the patient's dentition is gathered. The 3D model may comprise a virtual representation of the patient's dentition at a specific treatment stage of an orthodontic treatment plan.

At an operation 584, an image of the patient is gathered. In some implementations, the image includes at least a portion of the patient's face and including at least a portion of the patient's dentition. At an operation 586, first identifiers of a first set of reference points modeled on the three-dimensional model of the patient's dentition are received. The first set of reference points may correspond to a set of anatomical points on the patient's dentition. In some implementations, the first set of reference points are provided by a technician or other clinical professional who has identified specific anatomical portions of the 3D representation of interest to make photo-realistic and/or humanistic. The first set of reference points may be chosen to minimize "uncanny valley" problems with machine representations of the patient's dentition. In some embodiments, the reference points may include the gingival apex of one or more teeth, such as the anterior teeth. In some embodiments, the reference points may include the midpoint of the incisal edge of the teeth or the ends of the incisal edges of teeth. In some embodiments, the reference points may be a cusp tip of one or more teeth, such as the cusp tips of the canine teeth. In some embodiments, facial landmarks and contours, selected using neural networks, or otherwise, as descried herein, may be used as reference points. Examples of reference points are further shown in FIGS. 7, 8, 9, 14 and 15 and discussed further herein.

At an operation 588, second identifiers of a second set of reference points modeled on the dentition of the image of the patient are received. The second set of reference points may correspond to the set of anatomical points on the patient's dentition. The second set of reference may be provided by the technician or other clinical professional.

At an operation 590, the image of the patient's dentition may be projected into a three-dimensional space to create a projected 3D model of the image of the patient's dentition. In various implementations, points at 2D coordinates of the image may be mapped into a 3D space so that representations of 2D features in the 3D space are identified.

At an operation 592, the first set of reference points on the 3D model of the patient's dentition may be aligned with the second set of reference points on the projected model of the image of the patient's dentition. In various implementations, the distance between one or more pairs of reference points or features is minimized. In some embodiments, the 3D bite model is rotated or translated about one or more of the three perpendicular axes of 3D space. In some embodiments, the size of the teeth relative to the 2D image may be selected by matching the distance and focal length of the rendering of the 3D bite model with focal length and the distance between the imaging device and the patient used when capturing the 2D image of the patient.

At an operation 594, instructions to display a modified image of the patient are provided. The modified image may represent the aligned first and second sets of reference points. In some implementations, the modified image is a highly photo-realistic, humanistic image of the patient's dentition. The modified image may include the estimated results of an intermediate or final stage of the orthodontic treatment plan. The modified image may accommodate various perspectives, zooms, angles, etc. of the patient's dentition as informed through data modeled in the 3D model.

Figure 6:
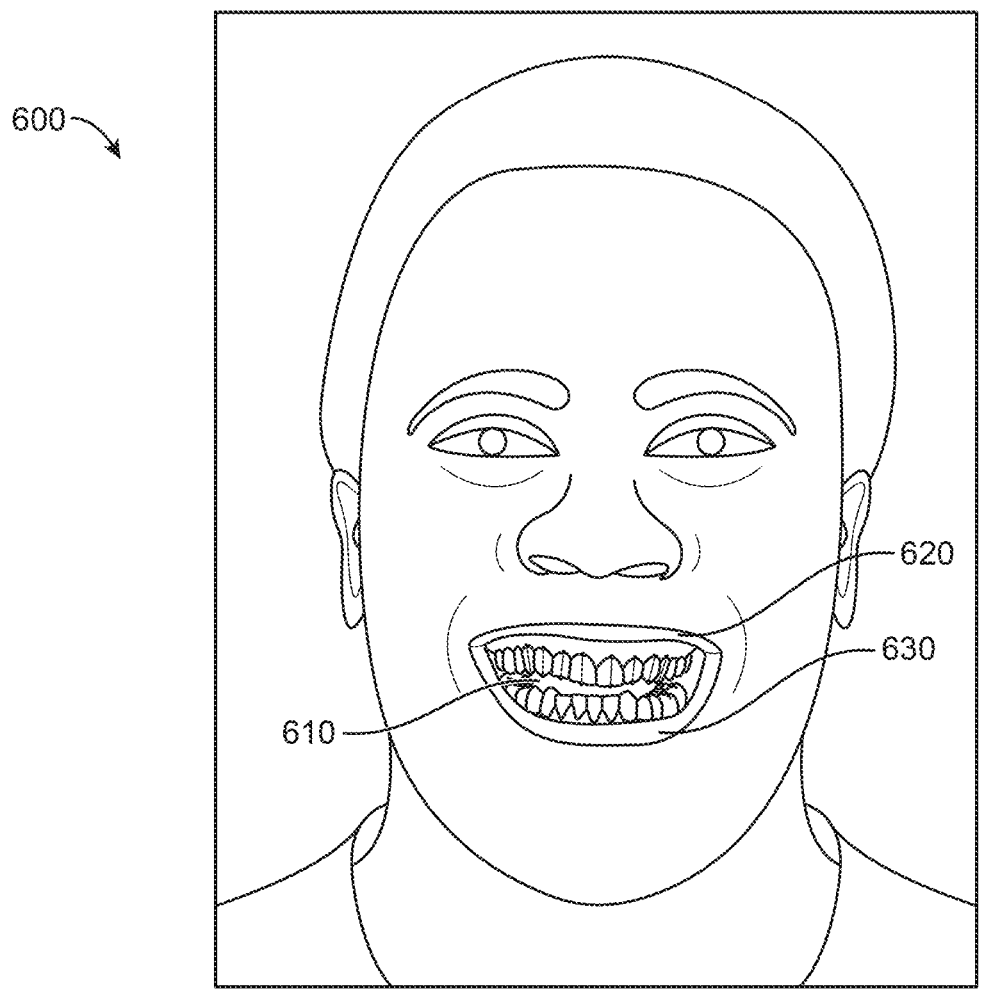
FIG. 6 depicts a two-dimensional (2D or 2-D) image of a patient, in accordance with one or more embodiments herein.

FIG. 6 depicts a two-dimensional image 600 of a patient, in accordance with one or more embodiments herein. The 2D image 600 may be received or captured as described above with respect to the method 500. The image 600 of the patient includes a 2D image of the representation of the patient's face that may be created by and received from an imaging device, such as a camera. In some implementations, the 2D image may have been captured with a camera, uploaded with a phone or computer, and/or uploaded over a network (e.g., the Internet). The 2D image 600 of the patient's face includes a mouth opening 610 and the patient's teeth and gingiva. The patient's mouth may be defined by the inner edges of the upper lip 620 and the lower lip 630. In particular, the outer perimeter of the mouth opening 610 may be defined by the lower edge of the upper lips 620, or a portion of the lower edge of the upper lips 620, and the upper edge of the lower lips 630, or a portion of the upper edge of the lower lips 630. FIG. 13D shows a process of finding lip edges and contours.

Figure 7:
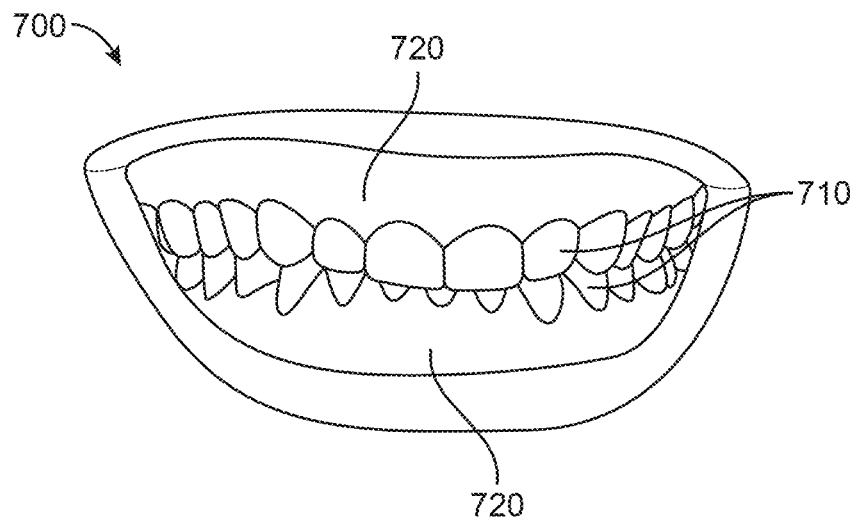
FIG. 7 depicts a three-dimensional (3D or 3-D) bite model of a patient's teeth, in accordance with one or more embodiments herein.

FIG. 7 depicts a 3D bite model 700 of a patient's teeth within the mouth. The 3D bite model may be formed as described above with reference to FIGS. 1-4. As shown in FIG. 7, the 3D bite model includes 3D models of the patient's upper and lower jaws, including the teeth 710 and gums 720 of the upper and lower jaws of the patient. In some embodiments, the 3D bite model is a model of the patient's teeth in a pre-treatment or initial position. In some embodiments, the 3D bite model depicts the teeth in the same relative positions as the relative positions of the teeth in the 2D image of the patient. For example, the 2D image of the patient and scan of the patient's teeth may have been created before treatment starts, such as, for example, on the same day or within a time period such that the position of the teeth in the 3D scan from which the 3D bite model is built substantially matches the position of the teeth at the time the 2D image of the patient is captured.

Figure 8:
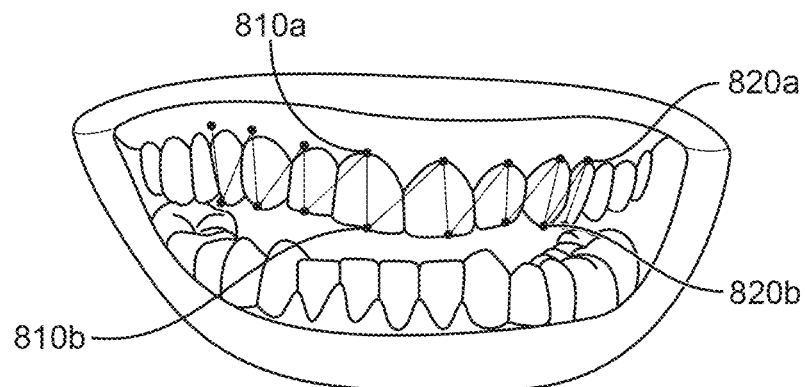
FIG. 8 depicts the selection of reference points on the 2D image of a patent, in accordance with one or more embodiments herein.

FIG. 8 depicts the selection of reference points 810a, 810b, 820a, 820b on the 2D image of a patent. The selection of the reference points 810a, 810b, 820a, 820b may be selected according to the process described above with respect to FIGS. 5A and 5B and block 530. In some embodiments, the reference points 810a, 820a may be the gingival apex of one or more teeth, such as the anterior teeth. In some embodiments, the reference point 810b may be the midpoint of the incisal edge of the teeth. In some embodiments, the reference point 820b may be a cusp tip of one or more teeth, such as the cusp tips of the canine teeth.

Figure 9:
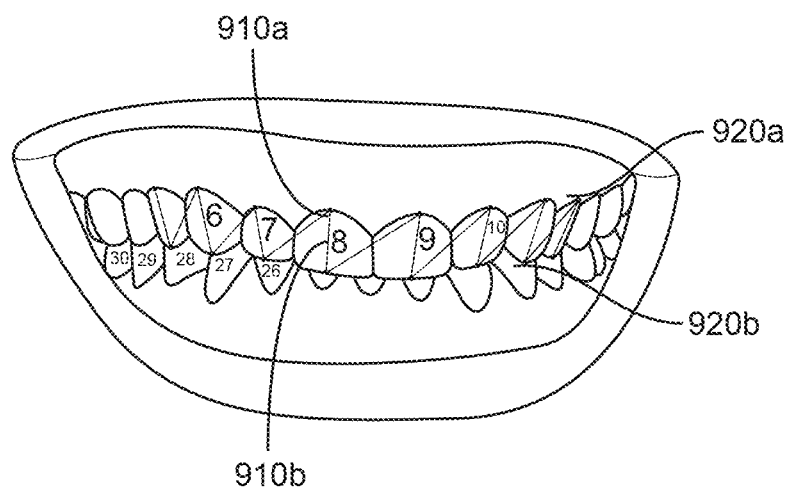
FIG. 9 depicts the selection of reference points on the 3D bite model of the patient's teeth, in accordance with one or more embodiments herein.

The references points of the 2D image may correspond to corresponding reference points at the same location on the 3D bite model. FIG. 9 depicts the selection of reference points 910a, 910b, 920a, 920b on the 3D bite model of the patient's teeth. The selection of the reference points 910a, 910b, 920a, 920b may be selected according to the process described above with respect to FIGS. 5A and 5B and block 530. In some embodiments, the reference points 910a, 920a may be the gingival apex of one or more teeth, such as the anterior teeth. In some embodiments, the reference point 910*b* may be the midpoint of the incisal edge of the teeth. In some embodiments, the reference point 920*b* may be a cusp tip of one or more teeth, such as the cusp tips of the canine teeth.

Figure 10:
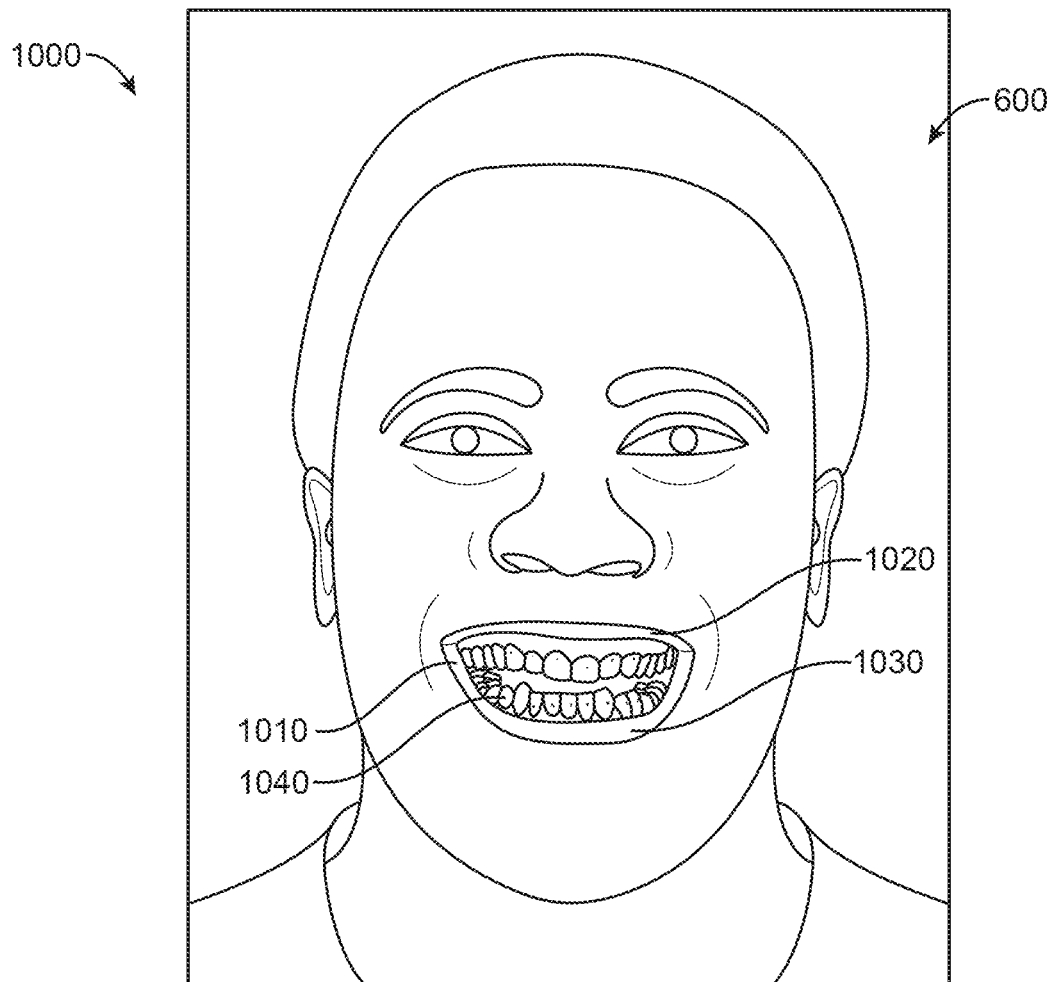
FIG. 10 depicts the integration of the 3D bite model into the 2D image of the patient to create a composite image, in accordance with one or more embodiments herein.
Figure 11:
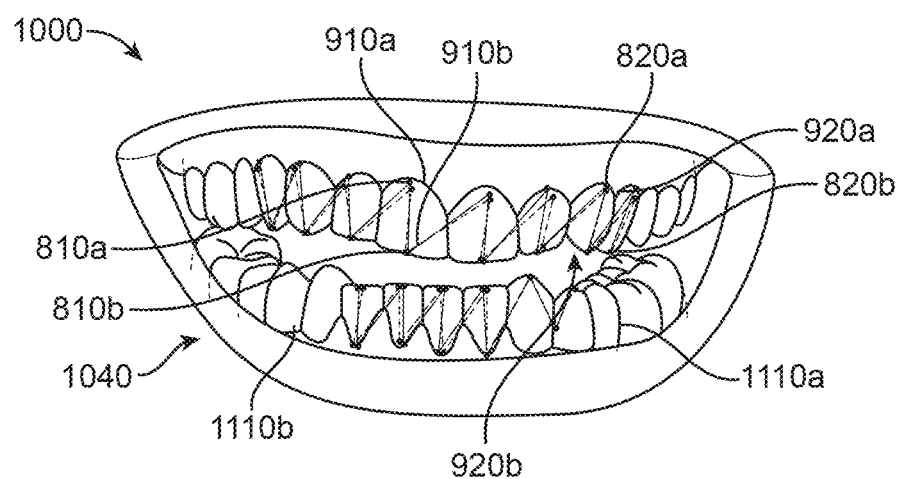
FIG. 11 depicts a close up of a composite image of the 3D bite model and the 2D image of the patient with overlaid contours, in accordance with one or more embodiments herein.

FIGS. 10 and 11 depict the integration of the 3D bite model 1040 into the 2D image 600 of the patient as part of the process to create a composite image 1000. The integration of the 3D bite model 1040 into the 2D image 600 depicted in FIGS. 10 and 11 may proceed as described above with reference to FIGS. 5A and 5B and block 540. In some embodiments, combining the 3D bite model 1040 with the 2D image 600 of the patient includes determining a mouth opening 1010 in the 2D image. In some embodiments, the mouth opening 1010 is the shape of the inside edge of the patient's lips 1020, 1030 in the 2D image. In some embodiments, the portion of the 2D image within the mouth opening 1010 is deleted or otherwise removed from the 2D image 600 of the patient. In some embodiments, the 3D bite model 1040, or a 2D projection of the 3D bite model 1040 is placed or rendered behind the 2D image 600 such that the 3D bite model 1040, or at least a portion of the 3D bite model 1040, is visible through the mouth opening of the 2D image of the patient.

As shown in FIG. 11, the 3D bite model 1040 is manipulated and positioned such that the teeth of the 3D bite model 1040 are in the same position and the same size as the teeth of the patient in the 2D image 1000.

FIG. 11 depicts a close up of a composite image 1000 of the 3D bite model and the 2D image 600 of the patient with overlaid contours 1110*a*, 1110*b* and reference points 810*a*, 810*b*, 820*a*, 820*b*, 910*a*, 910*b*, 920*a*, 920*b*. As depicted in FIG. 11, two corresponding reference points may be considered a pair of corresponding reference points. For example, a reference point 910*a* at the left incisal gingival apex of the 3D bite model can correspond with the reference points 810*a* at the left incisal gingival apex of the 2D image of the patient. As additional examples, reference points 810*b*, 910*b* are a corresponding pair of reference points at respective incisal edge midlines, reference points 820*a*, 920*a* are a corresponding pair of reference points at a respective gingival apex of the canine, and reference points 820*b*, 920*b* are corresponded a pair of reference points at respective canine cusps.

The alignment of the 3D bite model with the 2D image may be performed as described above with reference to FIGS. 5A and 5B and block 540 and elsewhere herein, for example as describe with reference to FIGS. 13A-F. The 3D bite model 1040 is manipulated and positioned such that the teeth of the 3D bite model 1040 are in the same position and the same size as the teeth of the patient in the 2D image 600. In some embodiments, the 3D bite model 1040 is positioned in the 2D image 600 by aligning each of the reference points on the 3D bite model 1040 to each of the corresponding reference points on the 2D image 600 of the patient. In some embodiments, the reference points of the 3D bite model 1040 are aligned with the corresponding reference points on the 2D image 600 of the patient by minimizing the sum of the distance between each corresponding pair of reference points. In some embodiments, the reference points of the 3D bite model 1040 are aligned with the corresponding reference points on the 2D image 600 of the patient by minimizing the sum of the squares of the distance between each corresponding pair of reference points.

In some embodiments, the 3D bite model 1040 and the 2D image 600 of the patient may be aligned based on the alignment of tooth contours 1110*a*, 1110*b* for the 3D bite model 1040 and the 2D image 600 of the patient. For example, the alignment may minimize the distance or square of the distance between respective points that define the contours 1110*a*, 1110*b* of the 3D bite model 1040 and the 2D image 600 of the patient.

In some embodiments, the 3D bite model may be aligned when the distance between all the reference points is less than a threshold, such as less than 0.05 mm, 0.1 mm, 0.2 mm, or 0.5 mm or wherein the sum of the squares of the distances between the reference points is less than a threshold or minimized.

Figure 12:
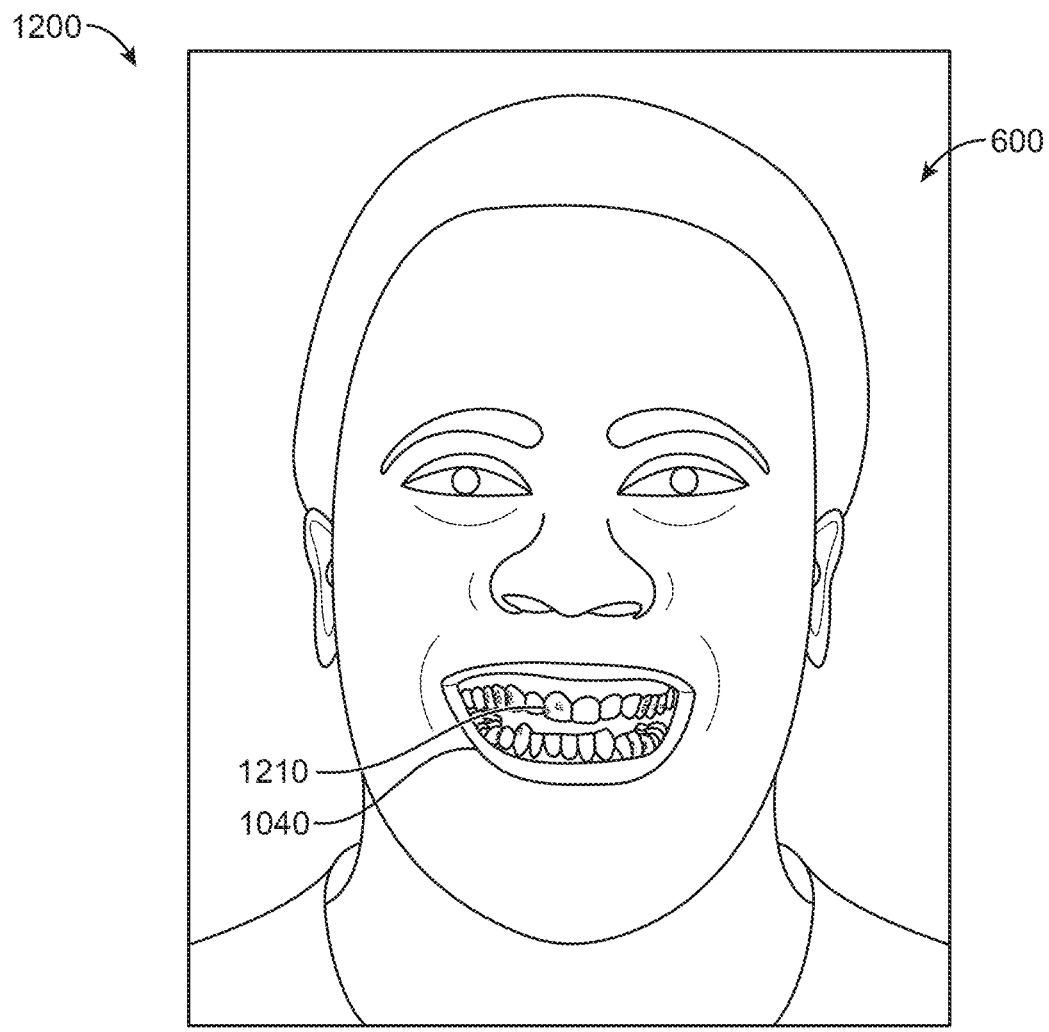
FIG. 12 depicts a composite image of the 3D bite model in a final position and the 2D image of the patient, in accordance with one or more embodiments herein.

FIG. 12 depicts a composite image 1200 of the 3D bite model 1040 and the 2D image of the patient with attachments 1210 placed on the patient's teeth. Attachments may be added to the 3D bite model during the treatment planning process to aid in applying forces to the teeth.

Figure 13:
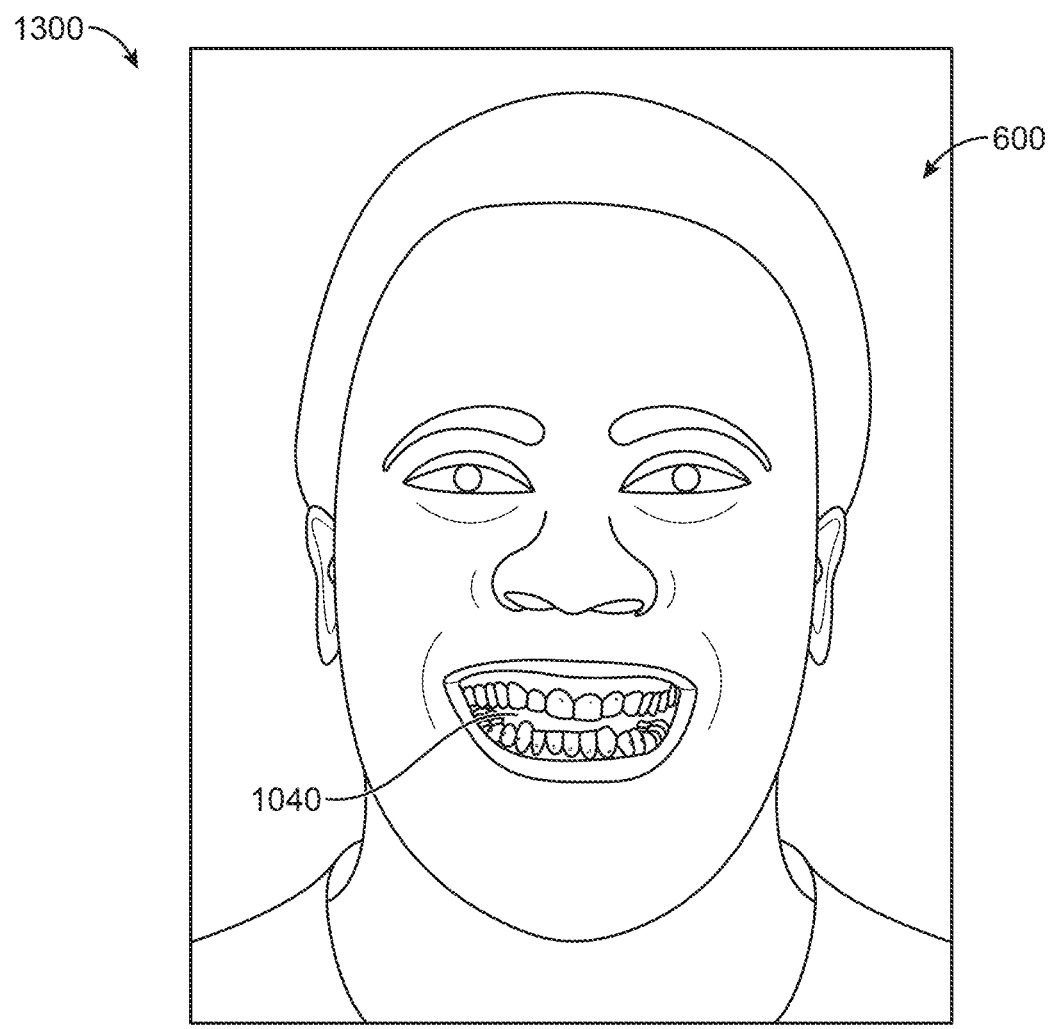
FIG. 13 depicts a composite image of the 3D bite model and the 2D image of the patient, in accordance with one or more embodiments herein.

FIG. 13 depicts a composite image 1300 of the 3D bite model 1040 with teeth in a final position and the 2D image of the patient. The 3D bite model 1040 and the 2D image of the patient may be aligned according to one or more embodiments described herein. Color and other feature matching may also be performed accordingly to one or more embodiments described herein.

Figure 13A:
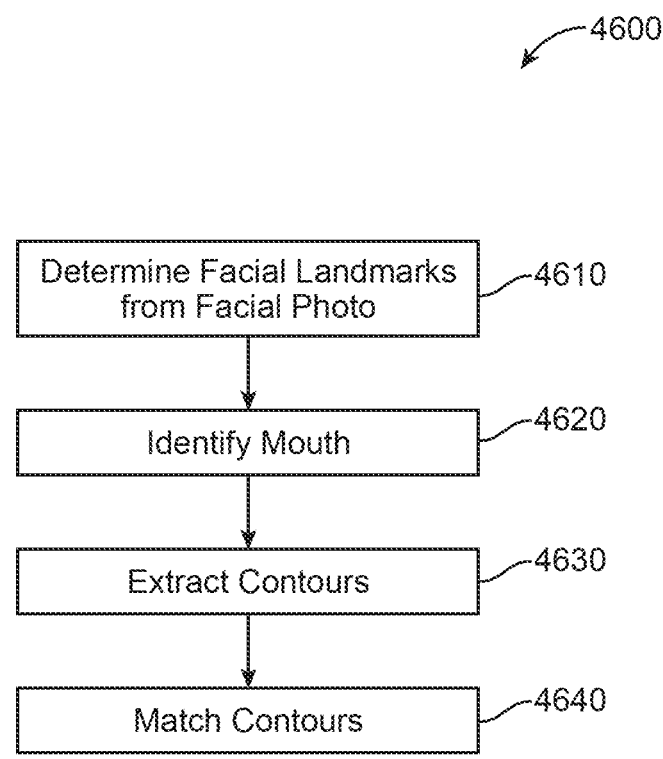
FIG. 13A depicts a method for extracting mouth and teeth contours from a patient's two-dimensional image and aligning with contours of a 3D model of the patients teeth, in accordance with one or more embodiments herein.

FIG. 13A depicts a method 4600 for extracting mouth and teeth contours from a patient's 2D image and aligning the image contours with contours of a 3D model of the patients teeth.

At block 4610 the method 4600 determines the facial landmarks from a facial image. The facial image may be a two-dimensional facial image of the patient. The patient's facial landmarks within the image are computed using a machine learning algorithm, such as a convoluted neural network, to determine facial features such as the jawline, the centerline of the face, the location of the eyes and eyebrows, the location of features of the nose, and also landmarks along the mouth opening and lips.

At block 4620 the shape and contours of the mouth opening are identified based on the facial landmarks determined at block 4610. For example, each of the landmarks identified as being located on an inner lip contour may be identified and contour lines may be drawn between each of the identified landmarks to determine the mouth opening. These facial landmarks may be used to detect a mouth region and to conduct a course placing of the 3D model inside the mouth.

At block 4630 the contours within the mouth opening are extracted. A convolutional neural network may be used to extract the contours of the lips, gingiva, and teeth from within the mouth opening. In some embodiments holistic edge detection architecture of a convolutional neural network is used to detect these and other contours described herein.

At block 4640 the contours extracted from the facial image are matched with the contours of a three-dimensional model of the patient's teeth. In some embodiments the 3D model of the patient's teeth are in an initial or pre-treatment position. For example the 3D model of the patient's teeth may have been derived from a scan of the patient's teeth taken at or around the same time as the image of the patient's face.

Figure 13B:
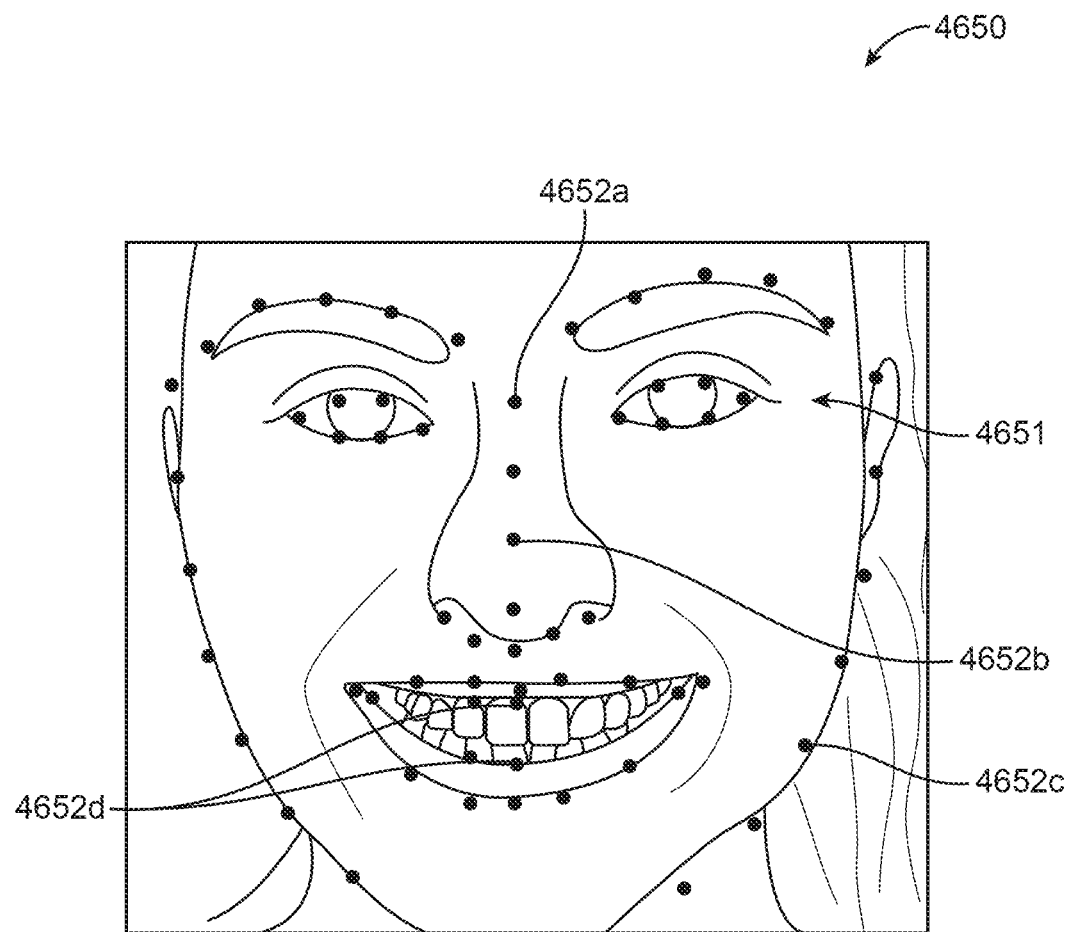
FIG. 13B depicts a method for determine facial landmarks, in accordance with one or more embodiments herein.
Figure 13C:
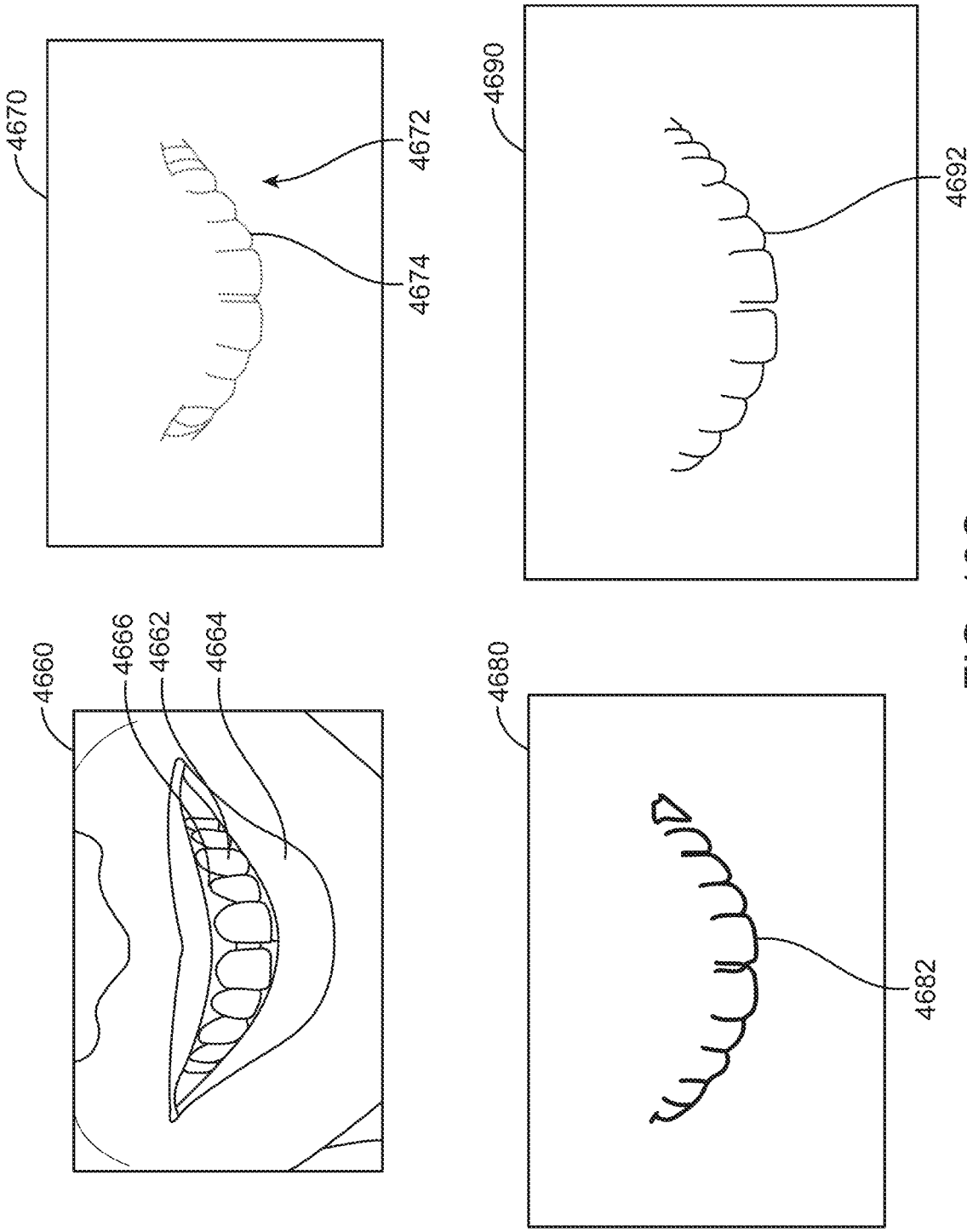
FIG. 13C depicts a method of determining dental contours, in accordance with one or more embodiments herein.
Figure 13D:
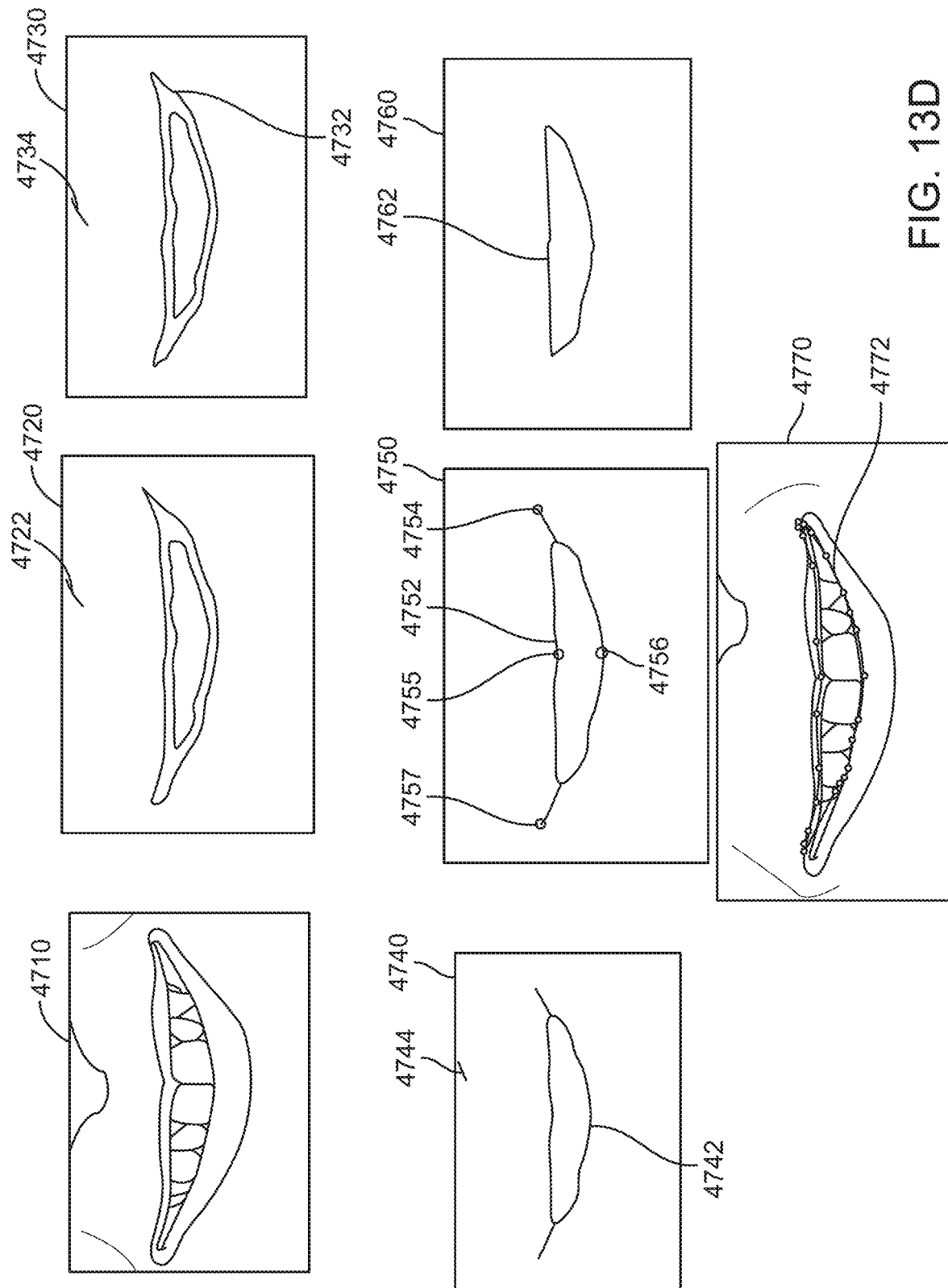
FIG. 13D depicts a method of determining lip contours and mouth openings, in accordance with one or more embodiments herein.

FIGS. 13B and 13C depict some of the operations of the method 4600 for extracting mouth and teeth contours from a patient's two-dimensional image in more detail.

FIG. 13B depicts a facial image 4650 of a patient with facial landmarks 4652 of a patient's face 4651 identified according to a machine learning algorithm. The facial landmarks 4652 may include nasal centerline landmarks 4652A, facial outline landmarks 4652C, and inner lip landmarks 4652D, among other landmarks such as landmarks that identify the patients ears, eyebrows, eyes, features of the nose, chin, and other facial features. These facial landmarks can then used to identify aspects of the patient's face. For example, the inner lip landmarks may be used to identify the mouth opening, within which the teeth and gingiva are located.

FIG. 13C shows the identification of the patient's lips, teeth, and gingiva. At panel 4660, the initial determination of the patient's lips 4664, teeth 4662, and gingiva 4666 contours are identified by a machine learning algorithm, such as a convoluted neural network.

At panel 4670, the initial tooth contours 4674 are extracted from the mouth area. In some embodiments, the lips, gingiva, and other facial contours identified in the facial image are removed from the image, resulting in an extraction of the tooth contours 4674 shown in panel 4670. The tooth contours 4674 shown in panel 4670 have a brightness or other scale applied to them. For example, in a grey scale image of the contours, each pixel may be assigned a value between 0 and 255, which may indicate a confidence that the pixel is a contour or may indicate the magnitude of the contour at that location.

At panel 4680, the tooth contours, and in particular, the pixels that denote the contours undergo binarization to change the pixels from a scale of, for example, 0 to 255, to a binary scale, for example, of 0 or 1, creating binarized tooth contours 4682. In the binarization process, the value of each pixel is compared to a threshold value. If the value of the pixel is greater than the threshold, then it may be assigned a new first value, such as a value of 1 and if the pixel is less than the threshold, then it may be assigned a new second value, such as a value of 0, for example.

At panel 4690, the binarized tooth contours 4682 from panel 4680 are thinned, whereby the contour's thickness is reduced to, for example, a single pixel in width, forming a thinned tooth contour 4692. The width of a contour for thinning may be measured as the shortest distance from a contour pixel adjacent to a non-contour pixel on a first side of a contour, to a contour pixel adjacent a non-contour pixel on a second side of the contour. The single pixel representing the thinned contour at a particular location may be located at the midpoint of the width between the pixel at the first side and the pixel at the second side.

After thinning the binarized tooth contours 4682, the thinned contour 4692 may be a single width contour at a location that corresponds to a midpoint of the binarized contour 4682.

After forming the thinned contour 4682 of the teeth, the thinned contours 4682 may be combined with lip contours, described below, and the facial image, as shown, for example, in FIG. 13E, discussed below.

FIG. 13D shows a process of identifying a patient's lip contours and mouth opening. At panel 4710 an image of a patient's face, and imparticular the mouth and the region near the mouth, is shown. The lip contours and mouth opening are determined based on such an image.

The initial determination of the patient's lips may be based on facial landmarks, such as the lip landmarks determined according to a machine learning algorithm. For example, the facial landmarks may include inner lip landmarks 4652D shown in FIG. 13D.

In some embodiments, the 3D model of the patient's teeth is initially coarsely placed within the mouth region. The initial placement is based on an alignment of the midline of the 3D model with a midline of the facial image determined based on the midline facial landmarks, such as the nasal midline landmarks 4652a of FIG. 13B. The initial scale of the 3D model may be determined by matching the scale of a distance between tips of opposite teeth, such as, by matching the distance between the upper canines in the 3D model with the distance between the tips of the upper canines in the facial image or matching the size of one or more teeth in the 3D model with the site of one or more corresponding teeth in the facial image.

Panel 4720 shows the initial determination of the patient's lip contours 4722, as identified by a machine learning algorithm, such as a convoluted neural network. These initial lip contours 4722 are extracted from the mouth area. In some embodiments, the tooth, gingiva, and other facial contours identified in the facial image are removed from the image, resulting in an extraction of the lip contours 4724 shown in panel 4720. In some embodiments, other facial contours 4722 may be present at this stage in the process.

As with the tooth contours 4674 shown in panel 4670, the lip contours 4722 have a brightness or other scale applied to them. For example, in a grey scale image of the contours, each pixel may be assigned a value between 0 and 255, which may indicate a confidence that the pixel is a contour or may indicate the magnitude of the contour at that location.

At panel 4730, the lip contours, and in particular, the pixels that denote the contours undergo binarization to change the pixels from a scale of, for example, 0 to 255, to a binary scale of, for example, 0 or 1, creating binarized lip contours 4732. The binarization process is similar to that described above with respect to FIG. 13C.

At panel 4740, the binarized lip contours 4732 from panel 4730 are thinned, whereby the contour's thickness is reduced to, for example, a single pixel in width, and forming a thinned lip contour 4742. As described above with respect to FIG. 13B, the width of a contour for thinning may be measured as the shortest distance from a contour pixel adjacent to a non-contour pixel on a first side of a contour, to a contour pixel adjacent a non-contour pixel on a second side of the contour. The single pixel representing the thinned contour at a particular location may be located at the midpoint of the width between the pixel at the first side and the pixel at the second side.

After thinning the binarized lip contours 4732, the thinned contour 4742 may be a single pixel width contour at a location that corresponds to the midpoint of the binarized contour 4732. The thinned contour image may still include other facial contours 4744 that are not part of the lip contours 4742. Accordingly, the largest connected component of the image may be determined to be the lip contours. This is possible, in part because, at the onset of the process, the 2D facial image included the mouth region and excluded or cropped out many, most, or all of the other facial features, such as one or more of the chin, jaw, eyes, ears, and most, or all of the nose.

Panel 4750 shows the extracted single pixel width lip contour 7452 along with four basic points of the lip contours. The four basic points may correspond to the left-most point 4757 of the lip contour 4752, the middle point of upper lip contour 4755 of the lip contour 4752, the right-most point 4754 of the lip contour 4752, and the middle point of lower lip contour 4756 of the lip contour 4752.

In some embodiments, shortest paths between the left-most point 4754 and the middle points 4755, 4756 and shortest paths between the right-most point 4754 and the middle points 4755, 4756 are determined, such paths 4762 are depicted in panel 4760.

In some embodiments, the shortest paths are refined based on the lip contours. For example, an iteratively built spline may be formed based on one or more of the shortest paths and the lip contour 4752. For example, an initial point of the spline may be located on the left corner of the mouth contour, which may correspond to the left-most point 4757. From this initial point a spline is built rightward along the lower lip towards the middle point of the lower lip contour 4756. When, advancement of the spline diverges from lower lip, as determined for example by maximizing R-square or another method, advancement stops and a new point is placed. The divergence may also be determined based on a sum of the square of the distance between the spline and the lip contours at points along the spline, or another method. The process then repeats until one or more splines are built between each of the four basic points. In some embodiments, the splines form a closed perimeter that corresponds to the mouth opening of the facial image.

After the spline or splines 4772 are formed, the splines 4772 may be combined with the facial image, as shown, for example, in panel 4770.

Figure 13E:
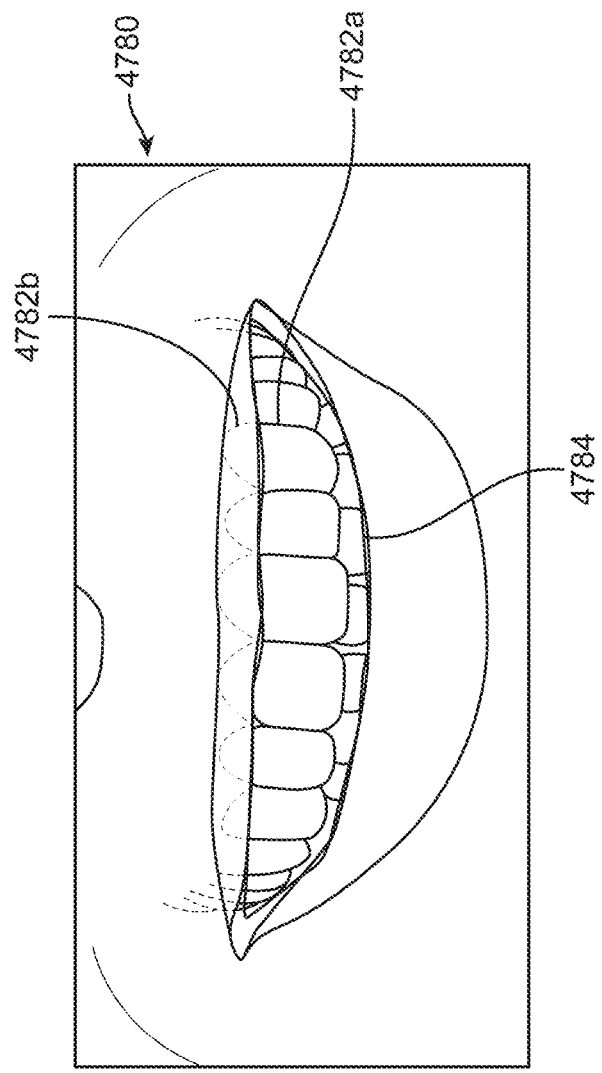
FIG. 13E depicts alignment of dental and lip contours with a 2D image of a patient, in accordance with one or more embodiments herein.

FIG. 13E shows the facial image with the contours 4782 of the 3D tooth model and lip contours 4784 overlaid thereon. To match the 3D tooth model tooth contours to the facial image, an expectation-maximization (EM) algorithm is used. First, the 3D tooth model contours are projected in an image plane. In some embodiments, the image plane is determined based on the distance between the imager or camera used to take the facial image and the focal length of the lens used to take the facial image. Then for the expectation step of the EM algorithm, for each pixel on the tooth contours from the facial image is matched to a similar pixel found on the 3D tooth model. On the maximization step of the EM algorithm the jaws or tooth arches of the 3D model are adjusted in one or more of translation and rotation in one or more of three orthogonal directions to minimize the total discrepancies between the pixels from the facial contours with pixels from the 3D model contours. In some embodiments, camera parameters may also be adjusted minimize total discrepancy. The total discrepancy may be determined based on a sum of least squares method or another method. In some embodiments, a pin-hole camera projection may provide an accurate projection of the 3D tooth model contours.

FIG. 13E shows the aligned lip contours 4784 and 3D model contours 4782 within the facial image 4780. The alignment accounts for the portion of teeth contours 4782a that are visible though the mouth opening defined by the lip contours 4784 and the portions of teeth contours 4782b that are not visible though the mouth opening. When rendering a composite 2D and 3D image (for example, as shown in FIGS. 12 and 13), the visible portions of the 3D tooth model may be rendered while the nonvisible portions of the 3D tooth model may not be rendered. For example, the teeth or other portions of the 3D tooth model, also referred to as a bite model, obscured by the patients lips, may not be rendered. The process of forming the composite 2D and 3D image may be performed at one or more of blocks 540 through 560 of FIGS. 5A and 5B.

Figure 23:
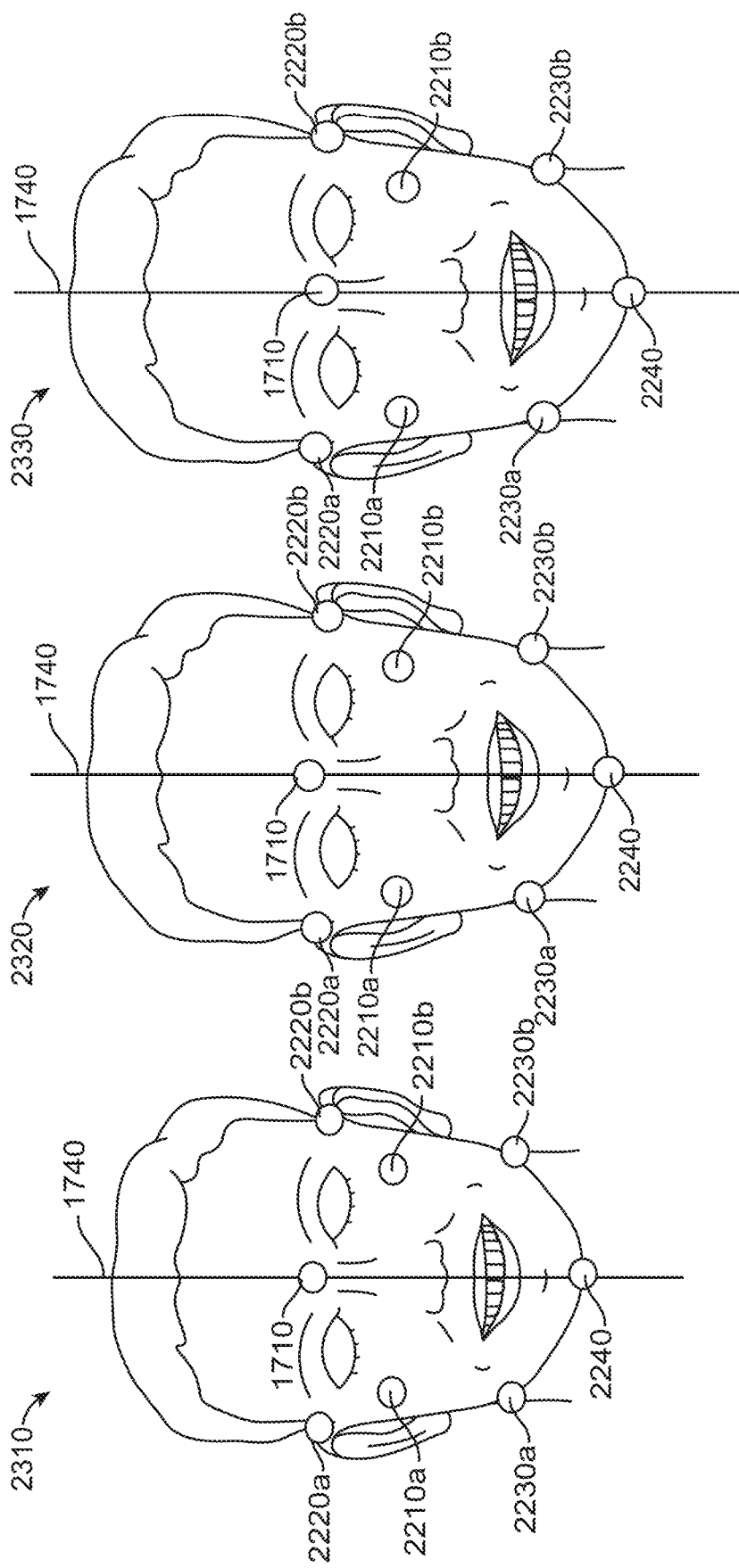
FIG. 23 depicts a method determining face and head shape of a patient, in accordance with one or more embodiments herein.
Figure 23A:
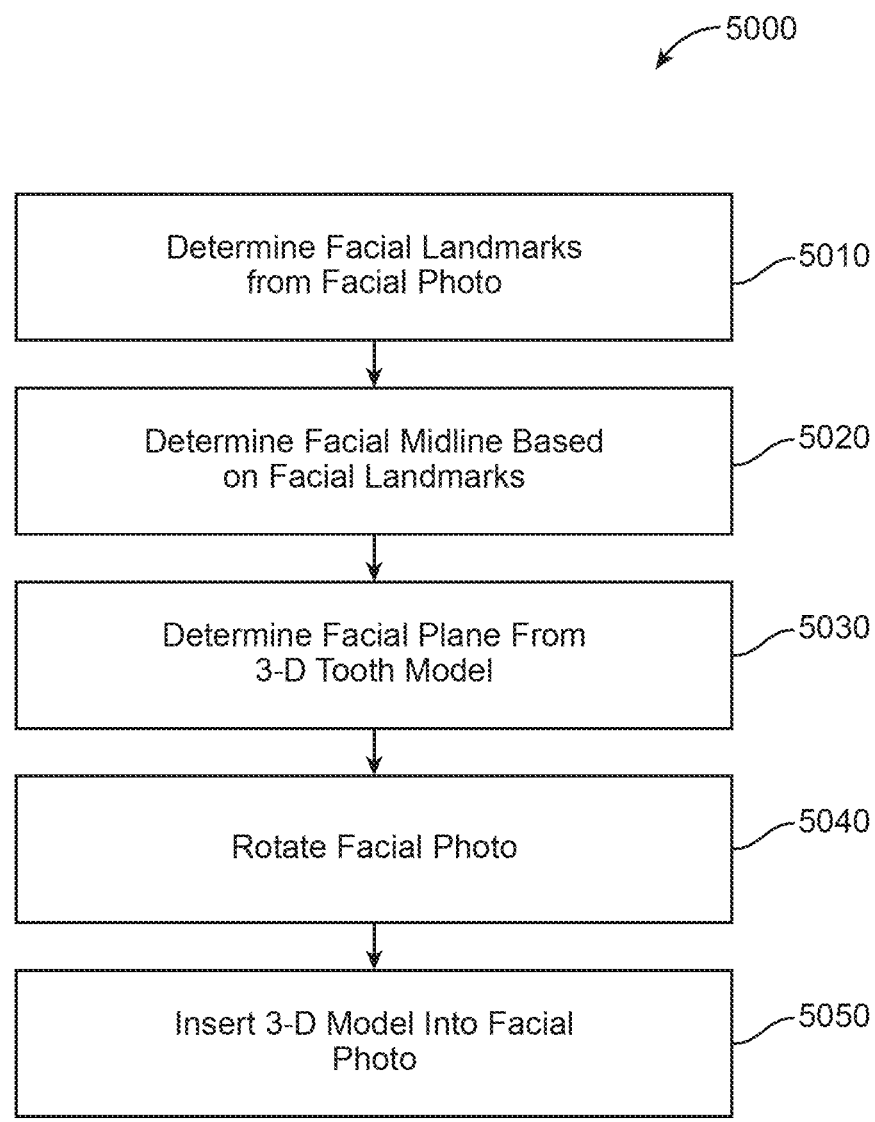
FIG. 23A depicts a method of aligning a 3D model of a patient's teeth with a facial image of the patient, in accordance with one or more embodiments herein.
Figure 23B:
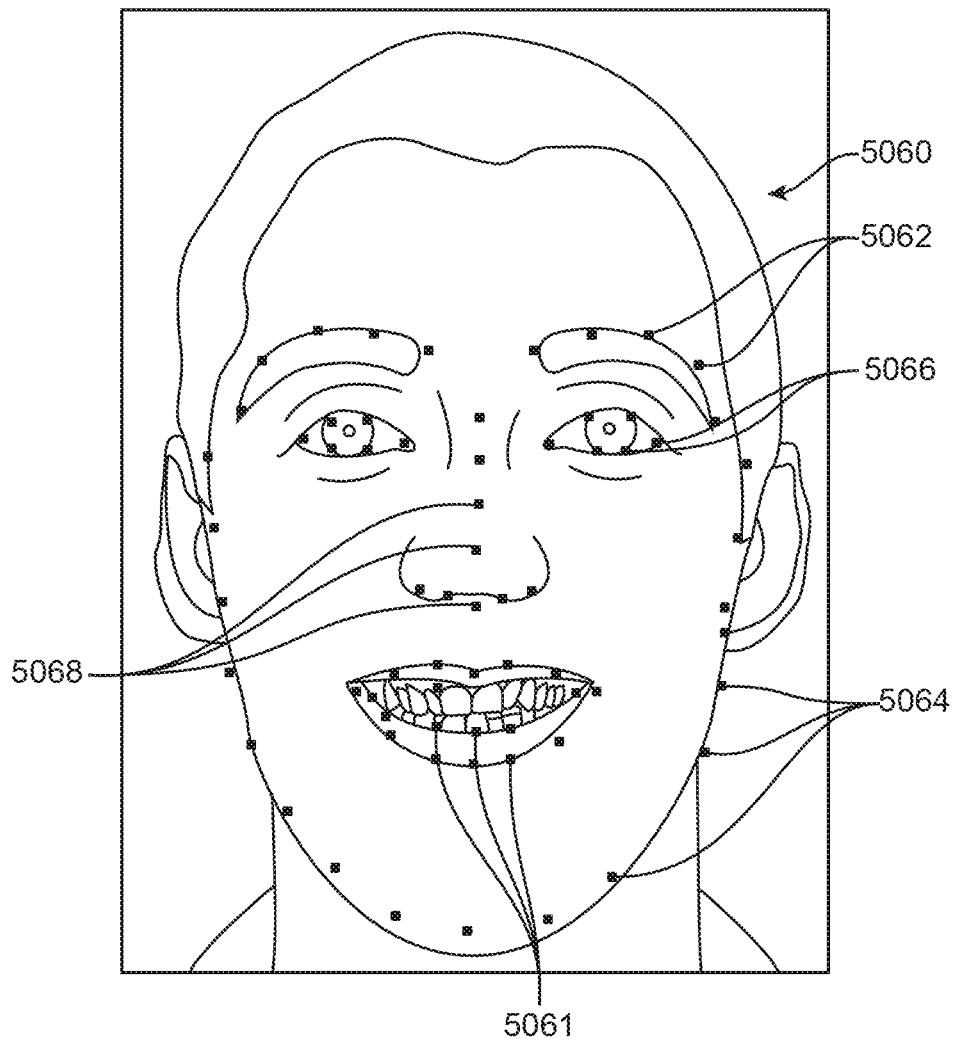
FIG. 23B depicts facial landmarks from a facial image of a patient, in accordance with one or more embodiments herein.
Figure 23C:
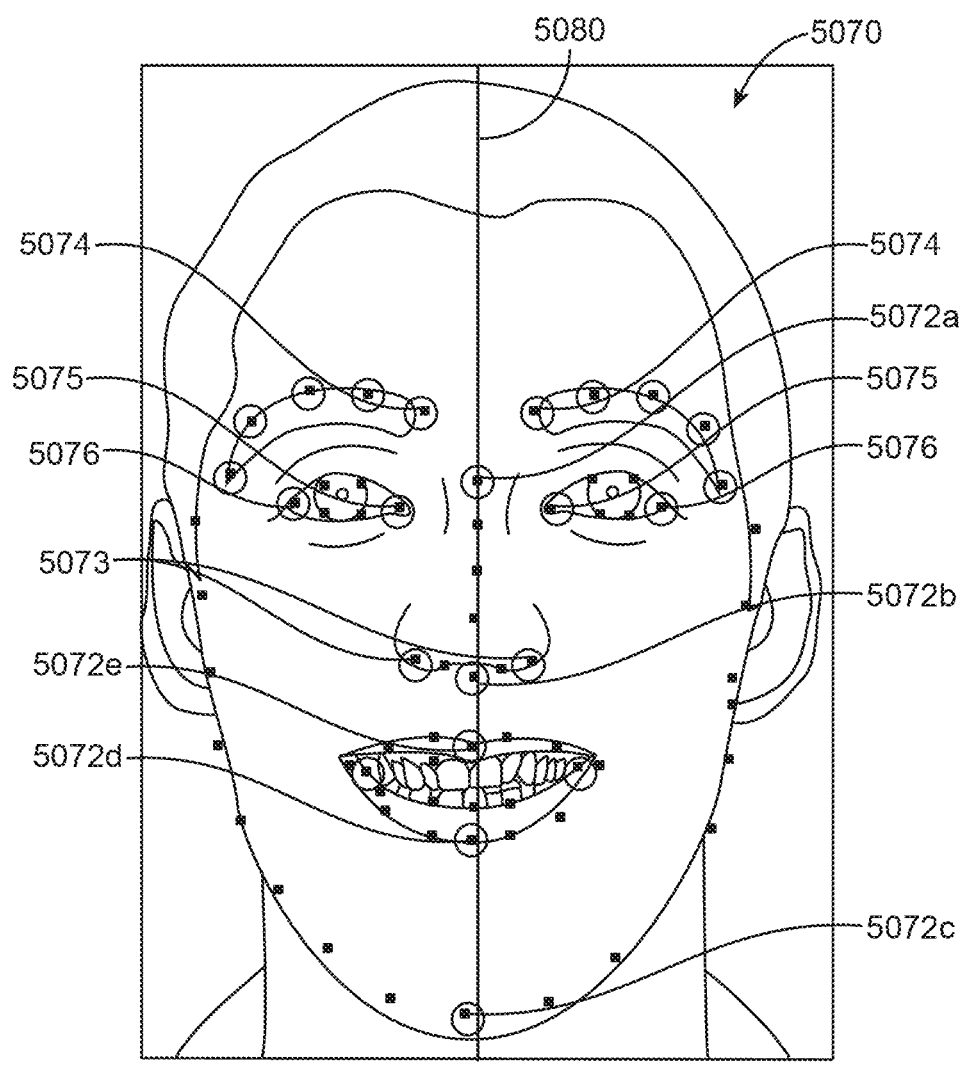
FIG. 23C shows a process of determining a facial midline from a facial image of a patient, in accordance with one or more embodiments herein.

FIGS. 23A-23D show a method 5000 of determining facial landmarks to aid in integrating a 3D tooth model into a facial image of a patient. At block 5010 facial landmarks from a facial image are determined. In some embodiments, the facial landmarks are determined based on a neural network that may have been trained on human faces. FIG. 23B shows a facial image 5060 with identified landmarks. The landmarks include eyebrow landmarks 5062 that identify the upper edge of a person's eyebrow, eye landmarks 5066 that identify the corners and lids of a person's eye, nasal landmarks 5068 that identify features of a person's nose, mouth landmarks 5061 that identify features of a person's lips and mouth, and facial outline landmarks 5064 that identity the outline of a person's face, such as the chin and jaw lines.

At block 5020 the facial midline of the facial image 5060 is determined based on the locations of the facial landmarks. In some embodiments, a subset of facial landmarks are used to determine the facial midline 5080 of the face in the facial image 5060. For example, in some embodiments, four central landmarks 5072 are used to determine the facial midline. These central landmarks 5072 are typically aligned along the facial midline and include a landmark 5072a along the nasal ridge between the eyes, a landmark 5072b at the tip of the nose, landmark 5072c and the center of the chin, and landmarks 5072d, 5072e at the center of the outer lower and upper lips, respectively.

In some embodiments, the average of symmetrical facial landmarks may be used to determine the facial midline. Symmetrical facial landmarks are pairs of landmarks that identify the same feature on each side of the face. For example, the pair of central eyebrow landmarks 5074 include a left central eyebrow landmark and a right central eyebrow landmark. Similarly, the other eyebrow landmarks may be used, such as the inner 5075 and outer 5076 canthus, the ala 5073.

These landmarks are generally equidistant from the facial midline. Accordingly, an average of the location of a pair of symmetrical facial landmarks is determined based on the location of each symmetrical landmark of the pair. This average location may be used to determine a midline point. The midline points from each pair of symmetrical points is then used to determine the facial midline 5080.

In some embodiments, both symmetrical facial landmarks and facial landmarks 5072 that are generally along the facial midline may be used to determine the facial midline 5080.

When determining the facial midline using either the facial landmarks 5072, the symmetrical landmarks, or a combination of both, the facial midline may be determined at a straight line that maximizes the R-squared of the distance between the facial midline 5080 and the respective landmarks, such as the landmarks 5072 and the average location of each pair of symmetrical landmarks. In some embodiments, the one or more landmarks may be weighted, such that their location has a greater or lesser effect on the position of the midline. For example, facial landmarks 5072, which may be referred to as midline landmarks may be weighted greater than symmetrical landmarks.

At block 5030 (see FIG. 23A) a facial plane is determined. A facial plane may be formed based on the facial midline 5080 and the position and focal length of the imager used to capture the facial image. The facial plane may be a 2D plane extending though the facial midline 5080 and may be parallel to the sagittal plane of the patient. A facial plane may be used to align a rendering of a 3D model of the patient's teeth, for example in initial, final, or intermediate positions, with the facial image of the patient.

Figure 23D:
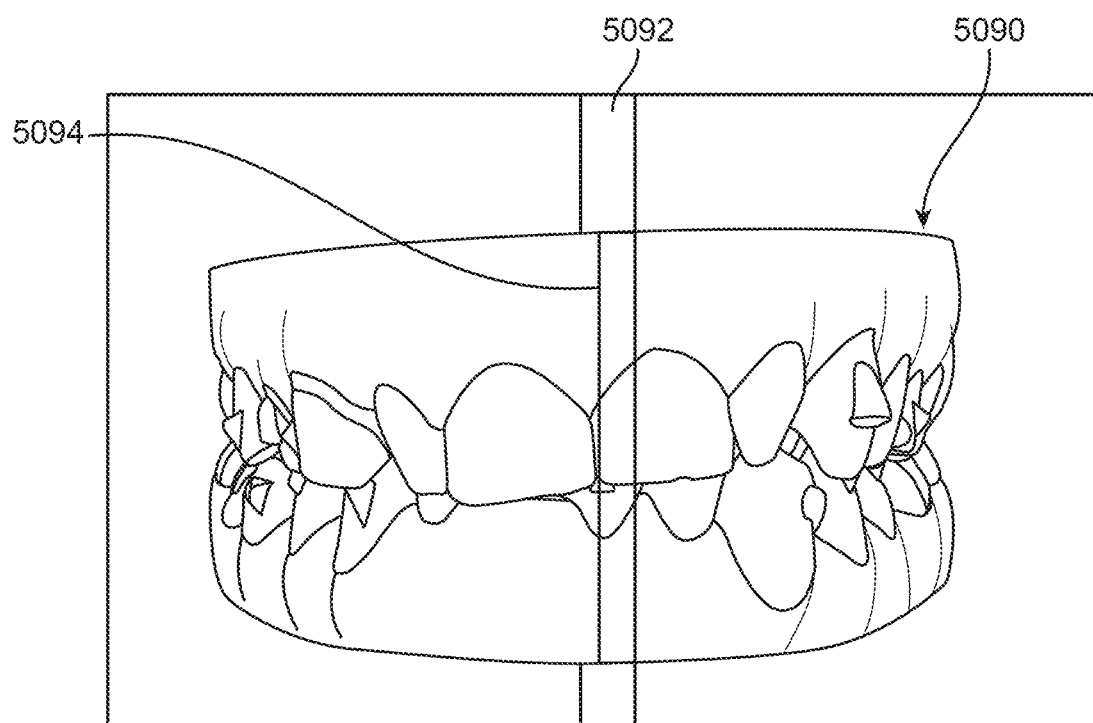
FIG. 23D shows a process of aligning a 3D model of a patient's teeth with a facial midline, in accordance with one or more embodiments herein.

FIG. 23D shows a 3D model of a patient's teeth 5090 and a facial plane 5092. The 3D model includes a dental midline 5094. The dental midline may be a line though the midpoint of the patient's arch, for example, the dental midline 5094 may extended between the upper central incisors. In some embodiments, the dental midline 5094 extends in a direction perpendicular to the occlusal plane of the patient. The dental midline 5094 may also be determined as described herein with reference to FIG. 18. To align the 3D model 5090 with a facial image of a patient, the facial plane 5092 and the dental midline 5094 are aligned by rotating and translating one or more of the 3D model 5090 and the facial plane 5092 until the dental midline 5094 is in the facial plane 5092. The rotations and/or translations of the facial plane 5092 are also carried out on the facial image. At block 5040 (see FIG. 23A), rotations of the facial image or photo are carried out. In some embodiments, the 3D model or the facial image may be rotated and translated.

In some embodiments, no rotations or translations of the facial image are carried out. Instead, the 3D model is rotated or translated until the dental midline 5094 is in the facial plane 5092.

After alignment of the facial image and the 3D model, such as described above by aligning the dental midline with the facial plane, the 3D model is inserted into the facial image or image of the patient.

Figure 13F:
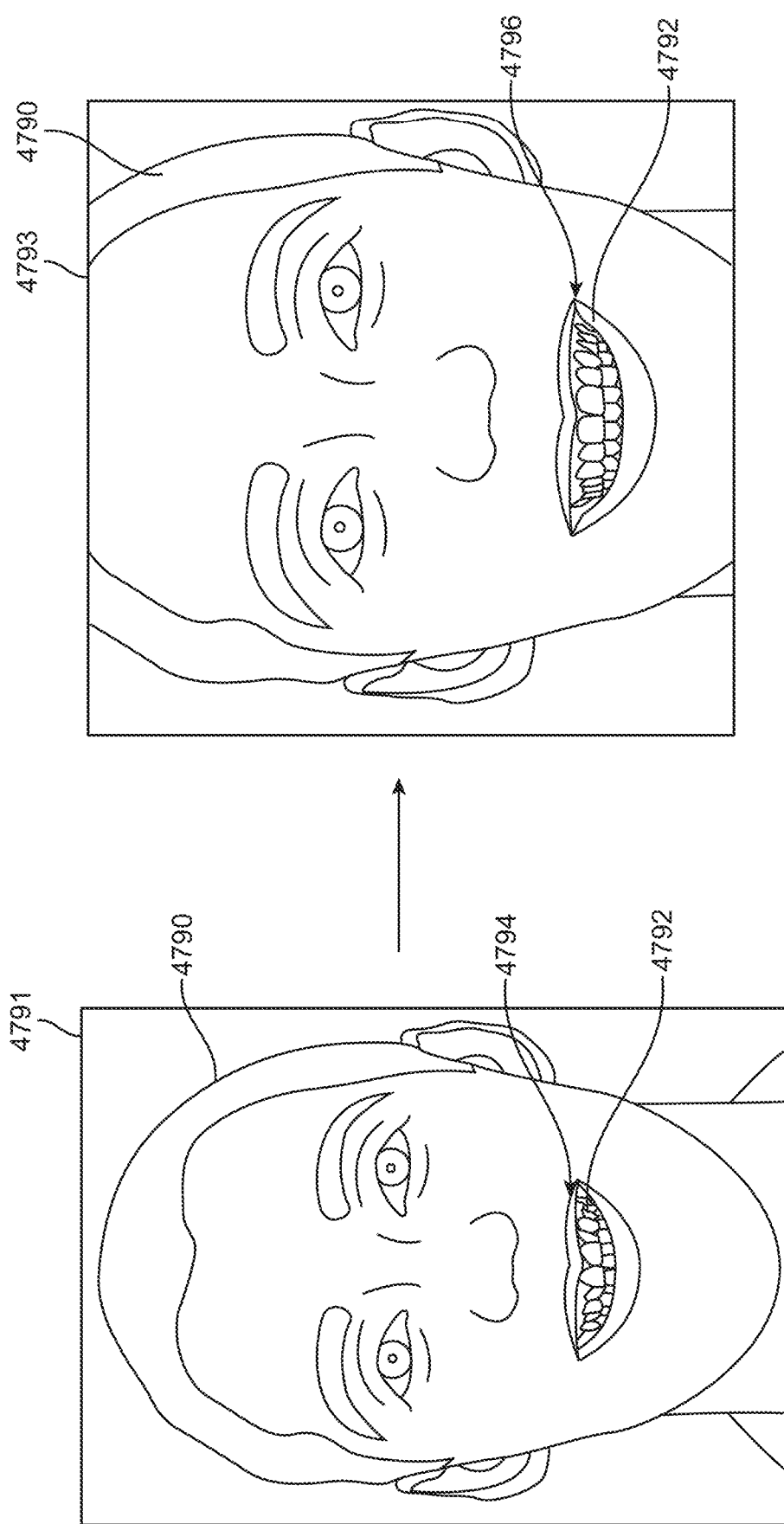
FIG. 13F depicts a morphing process of a facial image of patient between a pre-treatment state and a predicted post treatment state, in accordance with one or more embodiments herein.

FIG. 13F shows a process of morphing a rendering from a pre-treatment tooth arrangement shown in panel 4791 to a post-treatment or planned final tooth arrangement shown in panel 4793. The morphing algorithm may use a facial image 4790, the lip contours 4792, and masks of the teeth rendered in initial tooth positions 4794 and final tooth positions 4796 as inputs. The initial 2D and 3D composite image shown in panel 4791 may be rendered using the initial 2D facial image and the 3D model of the patient's teeth rendered in the initial position and the final composite image shown in panel 4793 may be rendered using the initial 2D facial image and the 3D model of the patient's teeth rendered in the final position.

To morph between the initial and final tooth positions, a segmentation mask may be built for both the rendering of the teeth in the initial position and the rendering of the teeth in the final positions. Such segmentation masks may include corresponding triangulation such that each triangle in the rendering of the first position corresponds to a triangle in the final position. The corresponding triangles may, and likely do, have different shapes in the initial and final renderings. The resulting morph between the teeth in the initial position and the teeth in the final position is a frame-by-frame translation of the triangles shaped according to the initial position to the triangles shaped according to the final position with corresponding color and shading translations.

Figure 14:
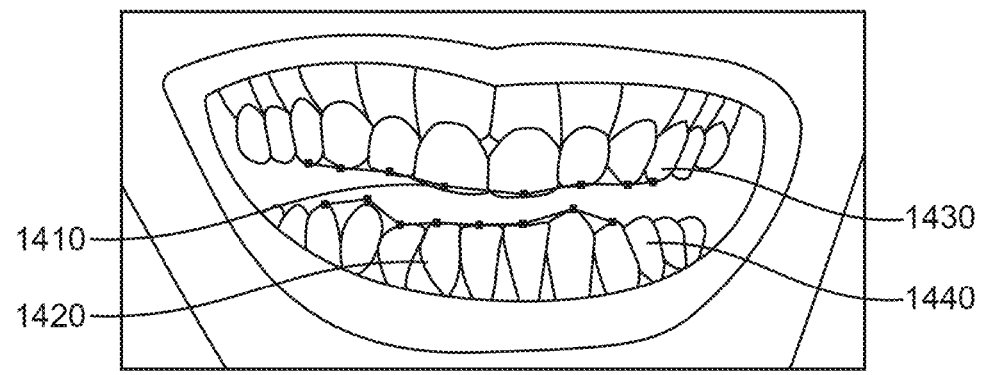
FIG. 14 depicts the selection of reference points on the 2D image of a patient, in accordance with one or more embodiments herein.

In some embodiments, the incisal edges of teeth may be used to align a 3D model of a patient's teeth with a 2D facial image of a patient. For example, FIG. 14 depicts an embodiment of the selection or determination of reference points along the incisal edge or cusps of the teeth on the 2D image of a patent. The selection of the reference points 1410, 1420, 1430, 1440 may be made according to the process described above with respect to FIGS. 5A and 5B and block 530. In some embodiments, the reference points 1410, 1420 may be the midpoint of the incisal edge of the teeth. In some embodiments, the reference points 1430, 1440 may be a cusp tip of one or more teeth, such as the cusp tips of the canine teeth.

Figure 15:
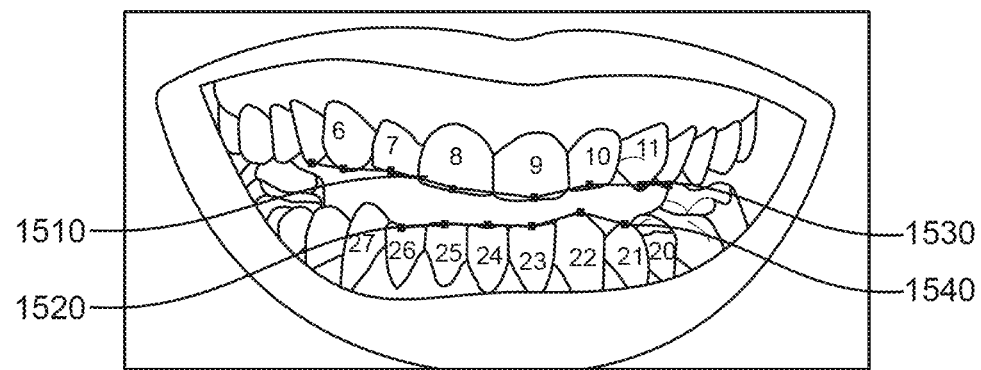
FIG. 15 depicts the selection of reference points on the 3D bite model of the patient's teeth, in accordance with one or more embodiments herein.

The references points of the 2D image may correspond to similar reference points at the same location on the 3D bite model. FIG. 15 depicts the selection of reference points 1510, 1520, 1530, 1540 on the 3D bite model of the patient's teeth. The selection of the reference points 1510, 1520, 1530, 1540 may be selected according to the process described above with respect to FIGS. 5A and 5B and block 530. In some embodiments, the reference points 1510, 1520 may be the midpoint of the incisal edge of the teeth. In some embodiments, the reference point 1530, 1540 may be a cusp tip of one or more teeth, such as the cusp tips of the canine teeth.

The integration of the 3D bite model 1040 into the 2D image may proceed as described above with reference to FIGS. 5A and 5B and block 540. In some embodiments, combining the 3D bite model 1040 with the 2D image 600 of the patient includes determining a mouth opening 1010 in the 2D image. In some embodiments, the mouth opening 1010 is the shape of the inside edge of the patient's lips 1020, 1030 in the 2D image. In some embodiments, the portion of the 2D image within the mouth opening 1010 is deleted or otherwise removed from the 2D image 600 of the patient. In some embodiments, the 3D bite model 1040, or a 2D projection of the 3D bite model 1040 is placed or rendered behind the 2D image 600 such that the 3D bite model 1040, or at least a portion of the 3D bite model 1040, is visible through the mouth opening of the 2D image of the patient. The 3D bite model 1040 is manipulated and positioned such that the teeth of the 3D bite model 1040 are in the same position and the same size as the teeth of the patient in the 2D image 600.

Two corresponding reference points may be considered a pair of corresponding reference points. For example, a reference point 1510 at the left incisal edge of the 3D bite model can correspond with the reference points 1410 at the left incisal edge of the 2D image of the patient. As additional examples, reference points 1430, 1530 are a corresponding pair of reference points at respective canine cusp tips.

The alignment of the 3D bite model with the 2D image may be performed as described above with reference to FIGS. 5A and 5B and block 540. The 3D bite model 1040 is manipulated and positioned such that the teeth of the 3D bite model 1040 are in the same position and the same size as the teeth of the patient in the 2D image 600. In some embodiments, the 3D bite model 1040 is positioned in the 2D image 600 by aligning each of the reference points on the 3D bite model 1040 to each of the corresponding reference points on the 2D image 600 of the patient. In some embodiments, the reference points of the 3D bite model 1040 are aligned with the corresponding reference points on the 2D image 600 of the patient by minimizing the sum of the in distance between each corresponding pair of reference points. In some embodiments, the reference points of the 3D bite model 1040 are aligned with the corresponding reference points on the 2D image 600 of the patient by minimizing the sum of the squares of the distance between each corresponding pair of reference points. In some embodiments, the 3D bite model may be aligned when the distance between all the reference points is less than a threshold, such as less than 0.05 mm, 0.1 mm, 0.2 mm, or 0.5 mm or wherein the sum of the squares of the distances between the reference points is less than a threshold or minimized.

Virtually Representing a Treatment Outcome Using Automated Detection of Facial and Dental Reference Objects In some implementations, one or more modules of the data processing system 400 may be configured to virtually represent an orthodontic treatment outcome by detecting and comparing facial and dental reference objects against one another. A "reference object," as used in this context, may refer to one or more physical and/or anatomical features of a patient that can be used to infer the placement of portions of digital 3D models within a 2D image. A "reference object" may be comprise elements of a patient's face or a patient's teeth/dentition. Examples of a facial reference object include: a facial midline along the sagittal plane of a patient's face; a location of the inferior boarder of the upper lip at a patient's facial midline; a location of the superior boarder of the lower lip at the facial midline; etc. Examples of a dental reference object include: a dental midline; an incisal edge position of one or more teeth; a gingival zenith of a central incisor; etc.

In various implementations, the processor(s) 402 gather from the storage subsystem(s) 406 a 3D model that models an initial position of a patient's teeth. The 3D model may include virtual representations of each of the patient's teeth and may depict translations and/or rotations of the patient's teeth along six degrees of freedom. The 3D model may include virtual representations of the patient's teeth at an initial pre-orthodontic treatment stage as well as along intermediate and/or final orthodontic treatment stages.

The camera 425 may be configured to capture an image of the patient's face. In some implementations, the camera 425 is located remotely to the other modules of the data processing system 400. As an example, the camera 425 may comprise a dedicated camera incorporated into an intraoral scanner, a cellphone camera, a network-coupled camera, a radiograph, scans related to PVS impressions, etc.

In some implementations, the processor(s) 402 may execute computer-implemented instructions stored on the storage subsystem 406 to select facial reference objects on images of the patient's face. As noted herein, the facial reference object may include one or more of: a facial midline along the sagittal plane of a patient's face; a location of the inferior boarder of the upper lip at a patient's facial midline; a location of the superior boarder of the lower lip at the facial midline; etc. Further, the processor(s) 402 may execute computer-implemented instructions stored on the storage subsystem 406 to select dental reference objects on the patient's teeth. The dental reference objects may be gathered from the 3D model of the patient's dentition. The processor(s) 402 may further execute computer-implemented instructions stored on the storage subsystem 406 to assign locations to the facial reference object(s) and/or the dental reference object(s). In various implementations, the processor(s) 402 may execute computer-implemented instructions stored on the storage subsystem 406 to compare locations of facial reference objects with locations of dental reference objects.

Advantageously, the processor(s) 402 may execute computer-implemented instructions stored on the storage subsystem 406 to modify interim positions of teeth on the 3D model using comparisons between locations of facial reference objects and locations of dental reference objects. In some implementations, modifications may be recommended and/or implemented. Depending on the implementation, the processor(s) 402 may only make modifications if a specified threshold value is reached, exceeded, etc.

As an example, the processor(s) 402 may execute computer-implemented instructions stored on the storage subsystem 406 to modify interim positions of teeth on the 3D model using comparisons between a facial midline and a dental midline; to the extent the dental midline does not match up with the facial midline, the dental midline of the 3D model may be modified. As another example, the processor(s) 402 may execute computer-implemented instructions stored on the storage subsystem 406 to modify interim positions of teeth on the 3D model using comparisons between an inferior boarder of the upper lip at the facial midline and incisal edge position; to the extent the incisal edge position does not match up with the inferior boarder of the upper lip at the facial midline, the incisal edge position of the 3D model may be modified.

As yet another example, the processor(s) 402 may execute computer-implemented instructions stored on the storage subsystem 406 to modify interim positions of teeth on the 3D model using comparisons between an superior boarder of the lower lip at the facial midline and incisal edge position; to the extent the incisal edge position does not match up with the superior boarder of the upper lip at the facial midline, the incisal edge position of the 3D model may be modified. As yet another example, the processor(s) 402 may execute computer-implemented instructions stored on the storage subsystem 406 to modify interim positions of teeth on the 3D model using comparisons between an inferior boarder of the lower lip at the facial midline and gingival zenith of a central incisor; to the extent the gingival zenith of a central incisor does not match up with the inferior boarder of the upper lip at the facial midline, the gingival zenith of a central incisor of the 3D model may be modified.

In some implementations, the processor(s) 402 may execute computer-implemented instructions stored on the storage subsystem 406 to identify a facial type of a patient. A "facial type," as used herein, may include a class of face shapes and/or characteristics from which to infer location of dentition after application of an orthodontic treatment plan. The facial type is determined based on a distance between the patient's glabella and chin and the distance between the patient's right and left cheekbone prominences. The processor(s) 402 may execute computer-implemented instructions stored on the storage subsystem 406 to modify widths of specific teeth, such as central incisors, lateral incisors, and canines in an interim final position represented on the 3D model. In various implementations, the processor(s) may execute computer-implemented instructions stored on the storage subsystem 406 to accommodate the size(s), shape(s), location(s), and relationships of restorative objects, such as crowns, veneers, etc.

Figure 16A:
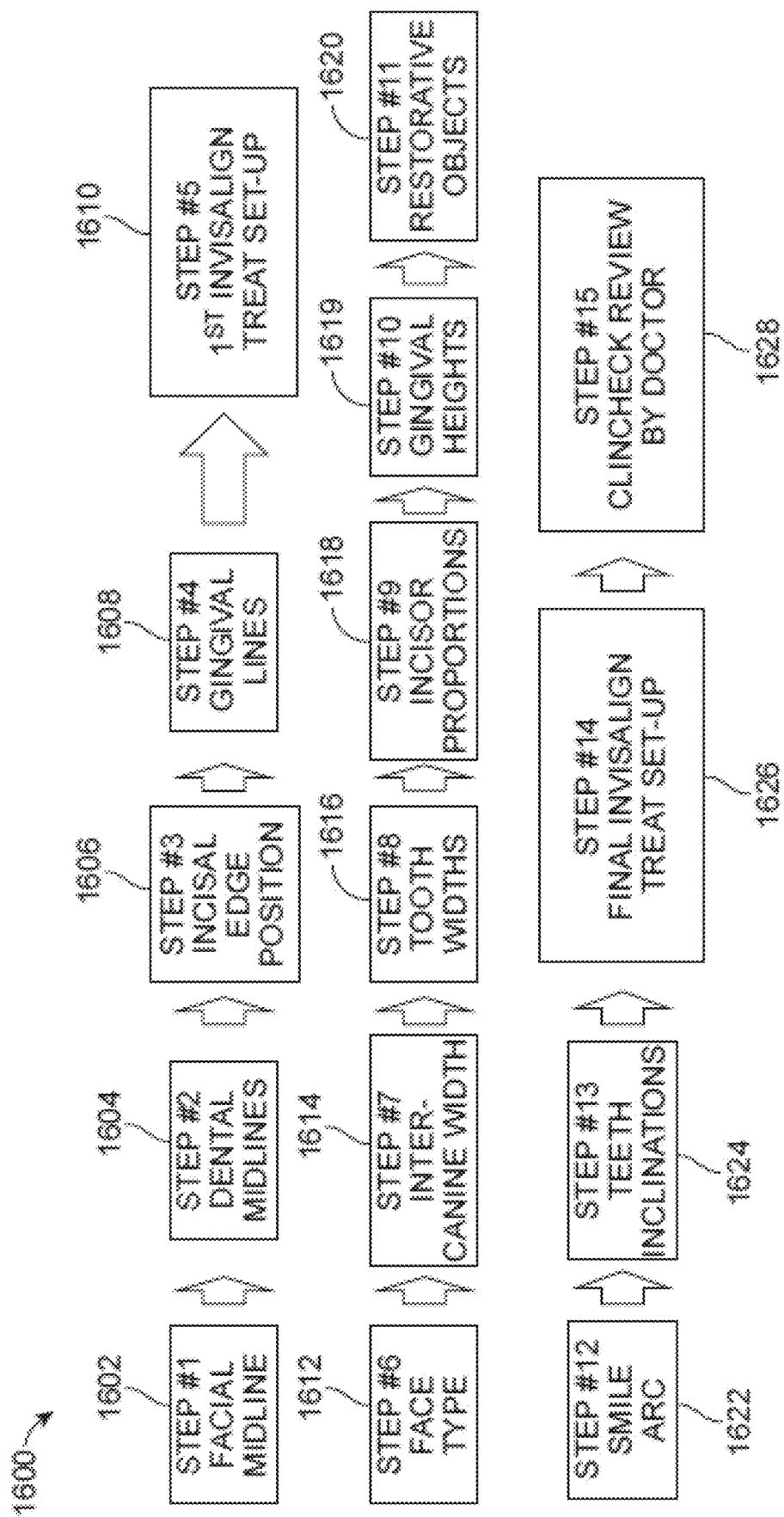
FIG. 16A depicts a method for planning the treatment of a patient's teeth, in accordance with one or more embodiments herein.

FIG. 16A depicts an embodiment of a method 1600 for determining a final position of a patient's teeth based, in part, on facial features, tooth proportions and positions, and gum positions. The method 1600 may be part of the process of developing a treatment plan and set of aligners for a patient as shown and described above, in particular with reference to FIGS. 1-4. In some embodiments, method 1600 takes place after the after an initial treatment planning process as described with reference to FIGS. 1-4.

Figure 17:
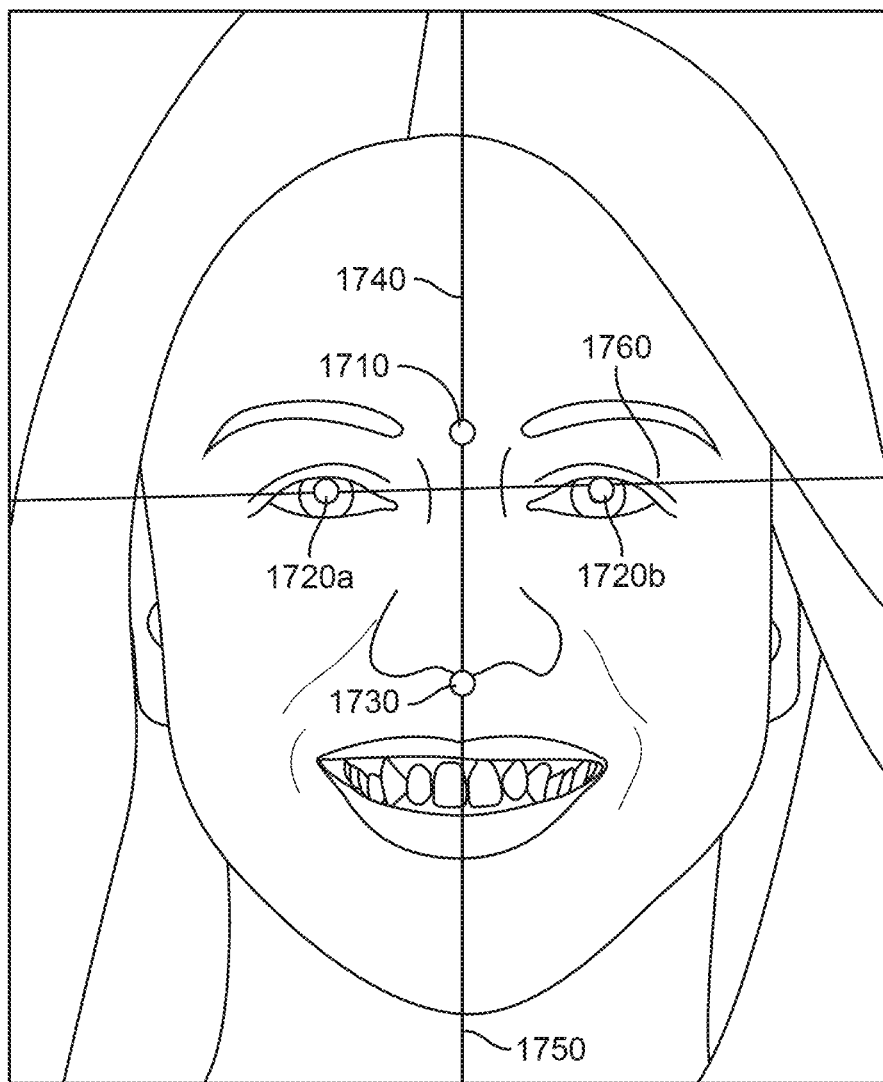
FIG. 17 depicts a method of selecting and determining reference points and lines on an image of a patient, in accordance with one or more embodiments herein.

At block 1602 the process of determining the facial midline and interpupillary line is conducted. FIG. 17 illustrates one embodiment of selecting, identifying or otherwise determining the facial midline and interpupillary line of a patient from the 2D image of the patient. Another method is shown and described with respect to FIGS. 23A-D. In some embodiments, the patient is imaged with a social smile facial expression. In some embodiments, a point of the subnasion 1730 and the glabella 1710 are selected or otherwise determined. A facial midline 1740 is drawn from or through the point of the glabella 1710 to or through the point of the subnasion 1730. In some embodiments, the point of subnasion 1730 is defined, and it remains static. In some embodiments, the image of the patient or the face of the patient in the image may be in a nonvertical orientation. In such embodiments, the image of the patient may be rotated until the facial midline 1740 is in a vertical orientation. In some embodiments, the image or face of the patient in the image may be rotated about either the point of the subnasion 1730 or the glabella 1710. In some embodiments an interpupillary line 1760 may be drawn through or between the points of the eye pupils 1720a and 1720b.

Figure 18:
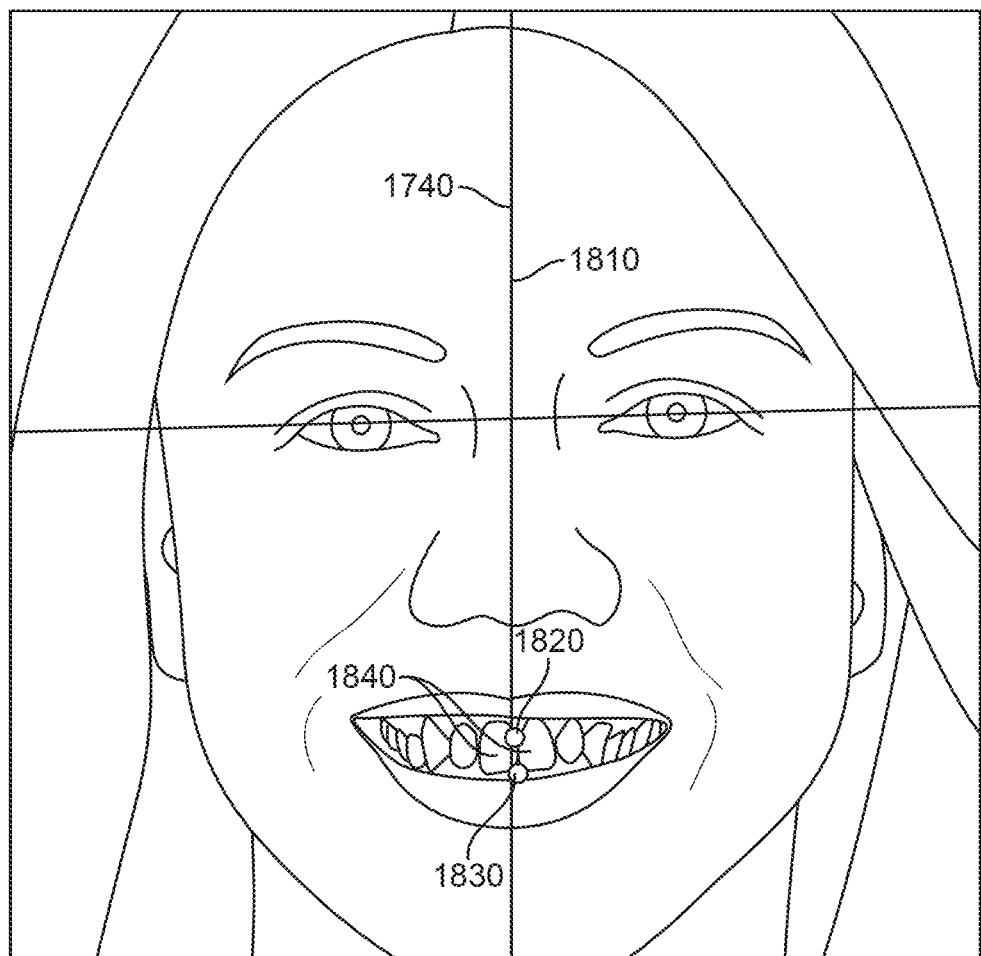
FIG. 18 depicts a method of selecting and determining reference points and lines on an image of a patient, in accordance with one or more embodiments herein.

At block 1604 of FIG. 16A, the dental midline from a 2D image of a patient with a social smile is selected or otherwise determined. As shown in FIG. 18, the dental midline 1810 may be selected or otherwise determined based on the location of the papilla 1820, the incisal embrasure 1830 of the anterior central incisors 1840, or the incisal embrasure between the lower incisors. The papilla 1820 is a small sounded protuberance on the gingiva and the incisal embrasures 1830 are the v-shaped valleys between adjacent teeth, such as the two anterior central incisors 1840. The dental midline 1810 may be defined as a line through the upper incisal embrasure 1830 of the anterior central incisors 1840, or the lower incisal embrasure between the lower incisors and parallel to the facial midline 1740. In some embodiments, a distance between the facial midline and the dental midline is determined. In some embodiments, if the distance between the facial midline and the dental midline is greater than a threshold value, such as 0.05 mm, 1 mm, 2 mm, 3 mm, 4 mm, or 5 mm, the final position of the teeth in the treatment plan may be determined such that that the dental midline is moved such that it is less than the threshold. In some embodiments, the threshold for movement is different than the threshold for the final position. For example, in some embodiments, the threshold distance below which the treatment planning does not adjust the dental midline is 2 mm, but once the treatment planning determines that the dental midline is moved, then the dental midline is shifted to below a second threshold value, such as 1 mm or 0.5 mm or until the facial midline and the dental midline are coincident.

Figure 19:
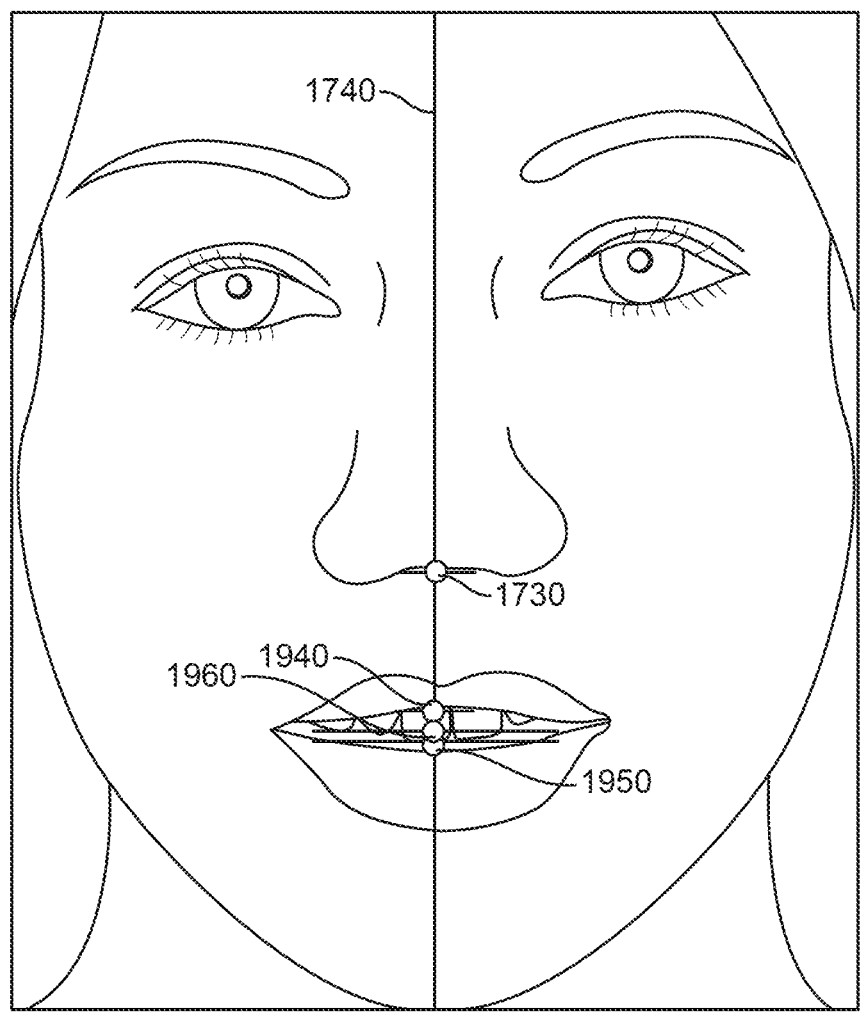
FIG. 19 depicts a method of selecting and determining reference points and lines on an image of a patient, in accordance with one or more embodiments herein.

At block 1606 the position of the incisal edge of the upper central incisors 1960 from a 2D image of a patient with a repose facial expression is selected or otherwise determined. As shown in FIG. 19, a horizontal line perpendicular to the facial midline 1740 at the subnasion 1743 may be generated or otherwise formed. A line perpendicular to the facial midline 1740 at the inferior border of the upper lip 1940 (the lower edge of the upper lip) may be generated or otherwise formed. A line perpendicular to the facial midline 1740 at the most inferior incisal edge point of the upper central incisors 1950 (the lowest edge point of the incisors in the upper dental arch) may be generated or otherwise formed. A line can be drawn perpendicular to the facial midline 1740 at a target position of the inferior incisal edge point of the upper central incisors 1960. The target position may be selected or otherwise determined based on facial aesthetics. An inferior position is the direction towards the feet, while a superior position is the direction towards the head.

Once these lines are generated, the distances between the lines may be measured to determine the spatial difference between the existing and the target positions. In some embodiments, the distance may be measured relative to the subnasion 1730 and the inferior incisal edge point of the central incisors 1950 to determine the initial position of the incisal edge of the teeth. In some embodiments, the distance may be measured between the subnasion 1730 and the target position of the inferior incisal edge point of the upper central incisors 1960, and this distance may be used for determining the target position of the incisal edge of the teeth. In some cases, the distances may be measured with reference to the inferior border of the upper lip 1940, rather than the subnasion 1730. In some embodiments, if the initial position of the incisal edge is outside of a target range, then the incisors may be moved as part of the treatment planning process to the final target position such that the incisal edge is within a target distance range. In some embodiments, the target distance range between the inferior border of the upper lip 1940 and the target position 1960 of the incisal edges 1950 may be between 3 and 4 millimeters.

Figure 20:
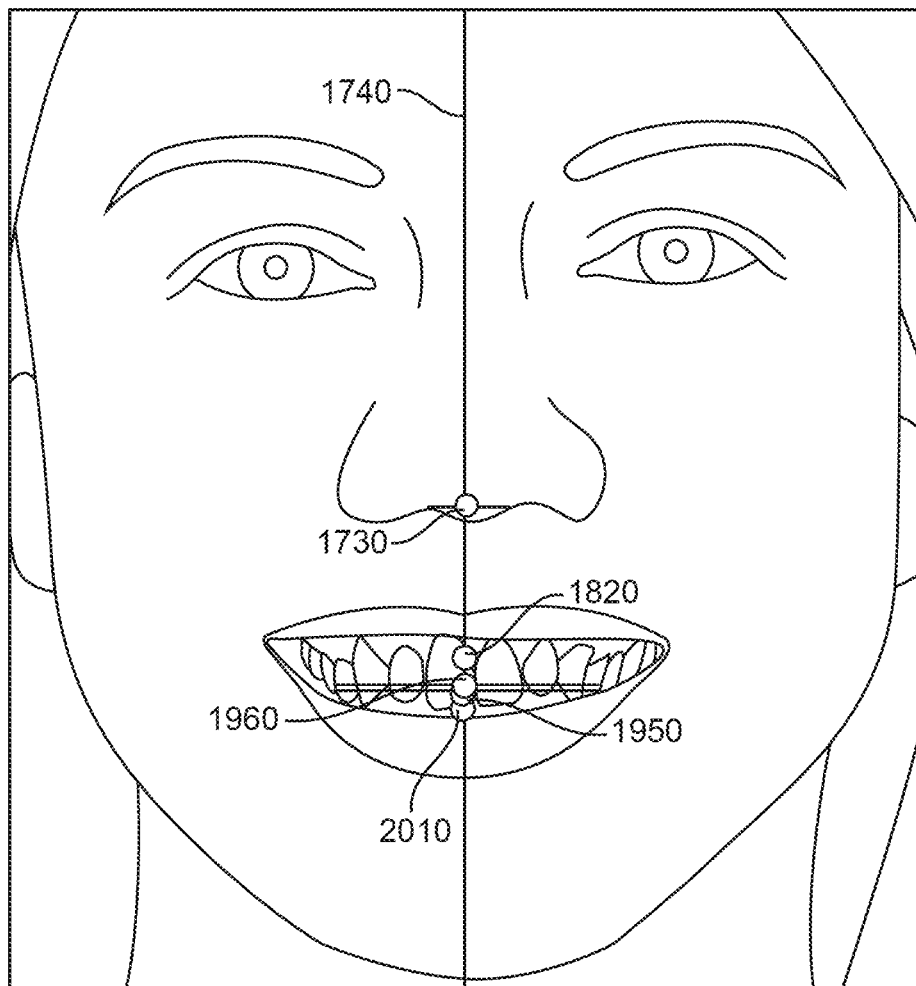
FIG. 20 depicts a method of selecting and determining reference points and lines on an image of a patient, in accordance with one or more embodiments herein.

In some embodiments, at block 1606 the position of the incisal edge of the upper central incisors 1960 from a 2D image of a patient with a social smile is determined. As shown in FIG. 20, a horizontal line may be generated or otherwise formed perpendicular to the facial midline 1740 through the subnasion 1730. A line may be drawn perpendicular to the facial midline 1740 at the most inferior incisal edge point of the upper central incisors 1950. A line may be drawn perpendicular to the facial midline 1740 at a target position 1960 of the inferior incisal edge point of the upper central incisors. The point of the superior border of the lower lip that intersects the facial midline 2010 may also be identified.

The distances between the lines may be measured. In some embodiments, the distances are measured to quantify the spatial difference between the existing and the target positions. In some embodiments, the distances may be measured between the subnasion 1730 and the inferior incisal edge point of the central incisors 1950, to determine an initial distance. In some embodiments, the distance may be measured between the subnasion 1730 and the target position 1960 of the inferior incisal edge point of the upper central incisors, and this distance may be used for determining the target position of the teeth as part of the treatment planning process. In order to design an aesthetically pleasing smile, the distance between the target position of the inferior incisal edge point of the upper central incisors 1960 and the superior border of the lower lip intersecting the facial midline 2010 may be less than or equal to 1 millimeter. In some embodiments, this distance may be less than or equal to 2 mm, for example, when the patient's lower lip is a dynamic or V-shaped lip in a social smile expression. In the treatment planning process, the teeth may be moved such that in their final positions, they are these threshold distances.

Figure 21:
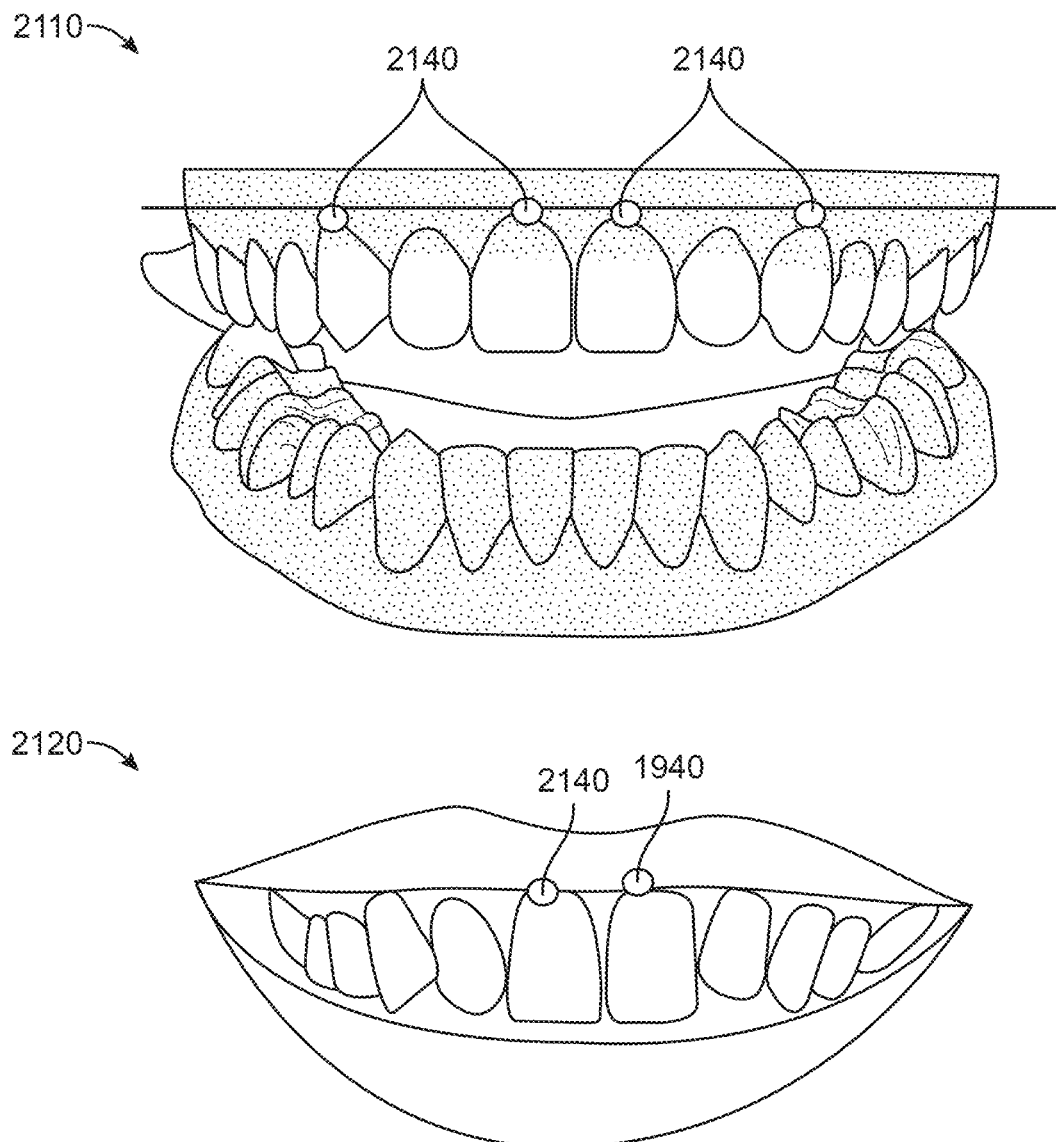
FIG. 21 depicts a method of selecting and determining reference points and lines on a 3D bite model and an image of a patient, in accordance with one or more embodiments herein.

At block 1608 the gingival line reference from a 2D image of a patient with a social smile 2120 is determined, for example, as shown in FIG. 21. The location of the gingival zeniths 2140 may be selected or otherwise determined. The inferior border of the upper 1940 can also be measured. The distance between the gingival zenith 2140 and the inferior border of the upper lip 1940 may be determined based on a composite image of the 3D bite model and the 2D image of the patient or from the 2D image of the patient without the 3D bite model. In some embodiments, the threshold distance between the gingival zenith and the inferior border of the upper lip, below which the gingival zenith may be altered during treatment planning may be 3 millimeters In some embodiments, the target range for the final distance after treatment is between −1 millimeters (the gingival zenith is above the inferior border of the upper lip and hidden) to 2 millimeters. The central incisor height (CIH) may be measured from the gingival zenith to the edge of the tooth. An aesthetic CIH can be less than or equal to 12 millimeters. In some embodiments, the treatment plan moves the teeth such that the CIH is less than 12 millimeters.

As described herein, an initial target final orthodontic position of the patient's teeth may be determined at block 1610 of FIG. 16A. In some embodiments, block 1610 may also include the generation of a treatment plan based on the initial orthodontic target position.

Figure 22:
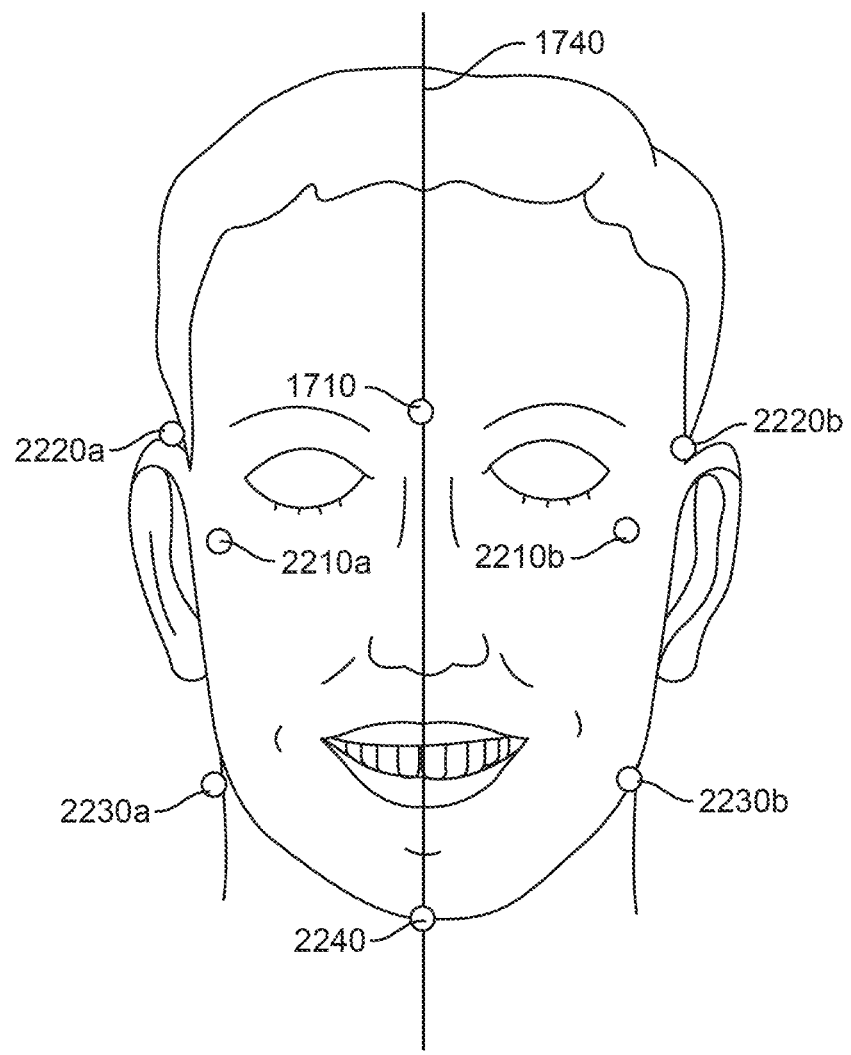
FIG. 22 depicts a method of selecting and determining reference points and lines on an image of a patient, in accordance with one or more embodiments herein.

At block 1612 of FIG. 16A a face type of the patient may be determined as shown in FIGS. 22 and 23. As shown in FIG. 22, reference points and the distances between pairs of reference points may be selected, measured, or otherwise determined. The location of the glabella 1710 may be determined at the intersection of the facial midline 1740. A point on the chin 2240 at the intersection of the facial midline 1740 may also be determined. The distance between point on the chin 2240 and the point on the glabella 1710 are used in conjunction with the distances between respective pairs of the other points to determine the shape of the patient's face.

A respective pair of points, one on each of the cheekbones 2210a, 2210b and the distance between them can be determined. A respective pair of points, one on each of the mandibular angles 2230a, 2230b and the distance between them can be determined. A respective pair of points, one on each of the temples 2220a, 2230b and the distance between them can be determined. Once these respective pairs of points and the distances between them are measured or otherwise determined, the distances between the points may aid in determining the spatial facial profile and to categorize the facial type as shown in FIG. 23.

FIG. 23 shows three face types, a short face type 2310, and average face type 2320, and a tall face type 2330. In a short-type face 2310, the distance between glabella 1710 and the chin 2240 is similar to or equal to the distance between the cheekbones 2210a and 2210b and similar or equal to the distance between the mandibular angles 2230a and 2230b, for example, the distances are within 10% of each other.

In an average-type face 2320, the distance between the glabella 1710 and the chin 2240 is much greater than the distance between the cheekbones 2210a and 2210b, for example between 15% and 20%; the distance between the cheekbones 2210a and 2210b is similar to or equal to the distance between the mandibular angles 2230a and 2230b; and the distance between the temples superior to the ears 2220a and 2220b is greater than the distance between mandibular angles 2230a and 2230b, for example, between 10% and 15%.

In a tall-type face 2330, the distance between the glabella 1710 and the chin 2240 is much greater than the distance between the cheekbones 2210a and 2210b, for example greater than 20%; the distance between the glabella 1710 and the chin 2240 is much greater than the distance between the mandibular angles 2230a and 2230b, for example greater than 20%; and the distance between the glabella 1710 and the chin 2240 is much greater than the distance between the temples superior to the ears 2220a and 2220b, for example greater than 20%, while the distances between the temples superior to the ears 2220a, 2220b, the distance between the mandibular angle 2230a, 2230b, and the distance between the cheekbone prominence 2210a, 2210b, are all similar, for example, within 10%.

Figure 24:
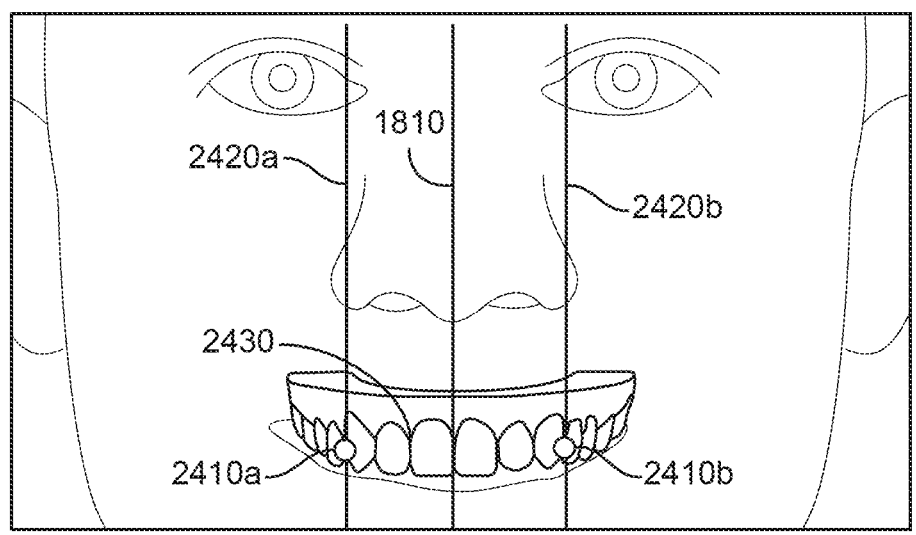
FIG. 24 depicts a method of selecting and determining reference points and lines on a 3D bite model of a patient, in accordance with one or more embodiments herein.
Figure 25:
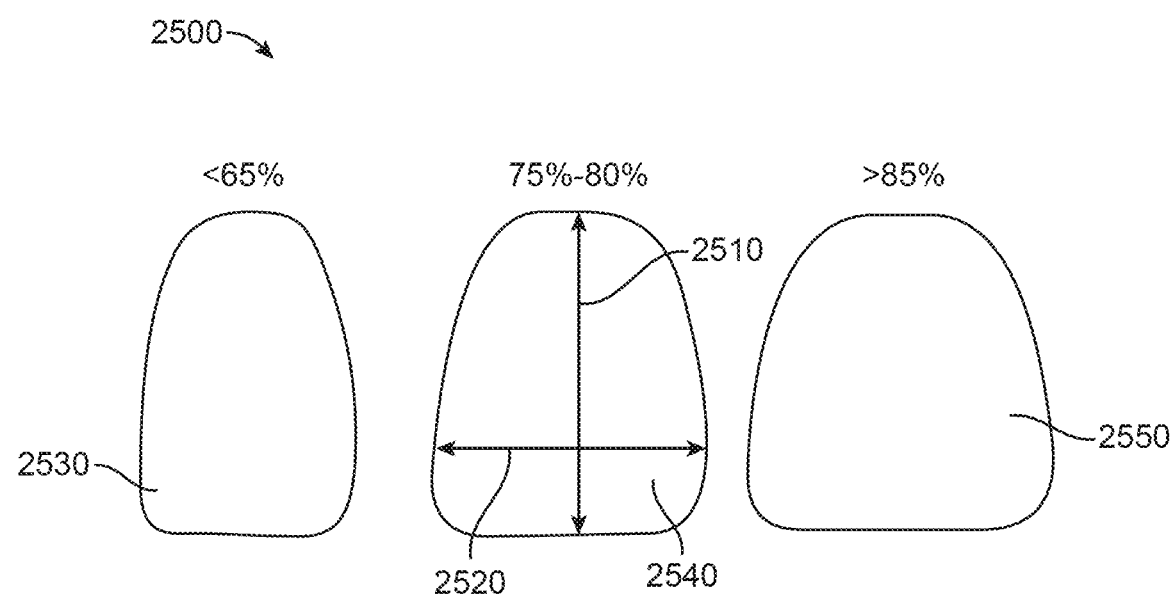
FIG. 25 depicts various possible shapes of teeth of a patient, in accordance with one or more embodiments herein.

At block 1614 the inter-canine width (ICW) is determined, for example, as shown in FIG. 24. The line that demarcates the inter-canine width 2420a and 2420b may be selected or otherwise determined by vertical lines through the most distal points on the buccal surfaces of the upper canines 2410a and 2410b. These ICW lines 2420a and 2420b are determined based on the teeth being in the orthodontic final position of the 3D bite model, as shown in FIG. 24. These ICW lines 2420a and 2420b are parallel to the dental midline 1810 and intersect the line drawn between the upper canines 2410a and 2410b.

At block 1616 the proportions of the upper anterior tooth widths may be determined. In some embodiments, the proportions of the upper anterior tooth widths may be determined based on the Recurring Esthetic Dental (RED) proportion or the upper anterior tooth width. Under RED proportions, the successive width proportion when viewed from the facial aspect should remain constant from the midline toward the posterior for the six anterior teeth between and including the canines. This property offers great flexibility to match tooth properties with facial proportions. Table 1 shows the RED proportions and anterior total widths based on the inter-canine-width (ICW) of the patient and the patient's face type. During the treatment planning process the teeth may be moved and/or restorative objections may be used such that at the end of treatment, the patient's teeth are within the RED proportions.

TABLE 1

Calculating RED Proportion & Anterior Total Widths from Inter-Canine Width (ICW) and Face Type

| | | Anterior Tooth Widths | | |
|---|---|---|---|---|
| Desired RED Proportion | | Central Incisor | Lateral Incisor | Canine |
| Face Type | RED % | Width (CIW) | Width (LIW) | Width (CW) |
| Tall | 66% RED | ICW/4.2 | CIW/0.66 | LIW/0.66 |
| Average | 70% RED | ICW/4.4 | CIW/0.7 | LIW/0.7 |
| Short | 75% RED | ICW/4.6 | CIW/0.75 | LIW/0.75 |

At block 1618 the central incisor proportion (CIP), which can be determined from the ratio of the central incisor width (CIW) or the width 2520 of the central incisor 2500 and the central incisor height (CIH) or the height of the central incisor 2500, is determined. In a short-type face 2530, the CIP is less than or equal to 85%. In an average-type face 2540, the CIP is 78%. In a tall-type face 2450, the CIP is greater than or equal to 70%.

Figure 26:
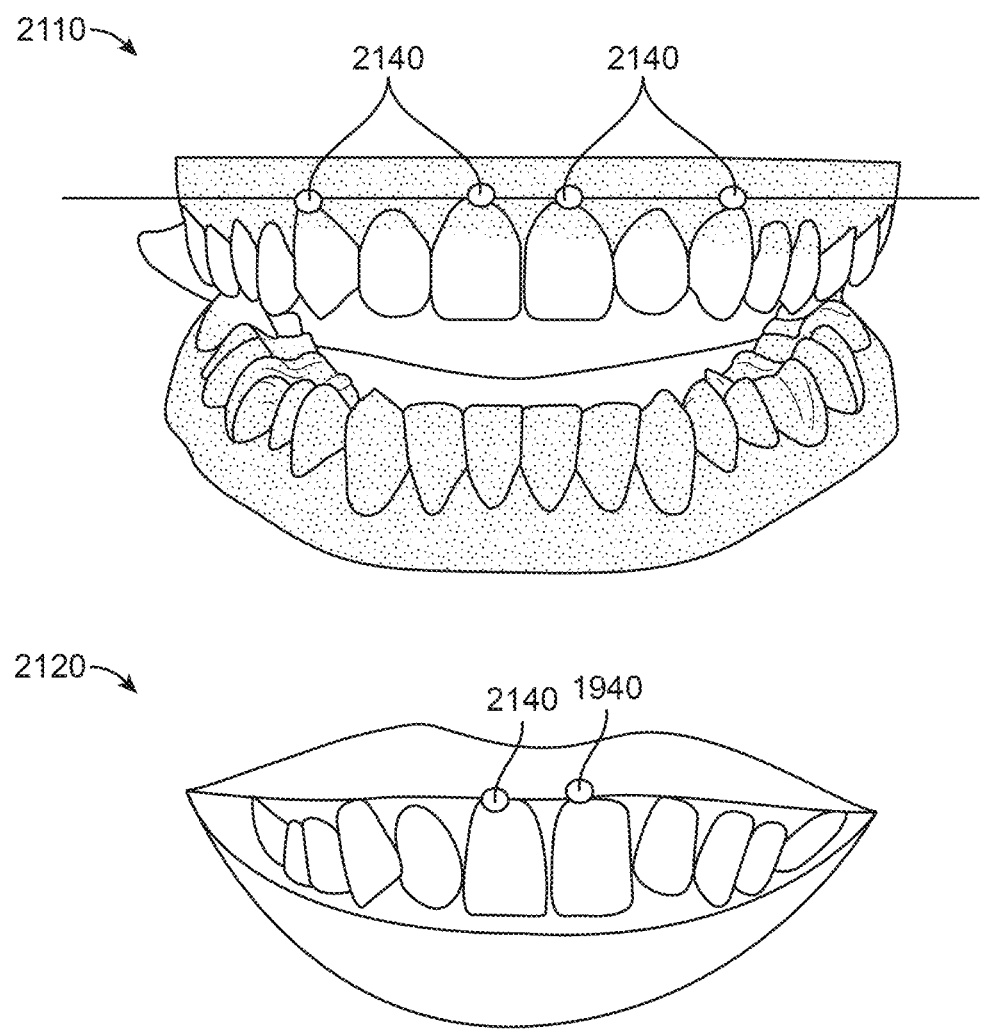
FIG. 26 depicts a method determining a gingival line of a patient, in accordance with one or more embodiments herein.

At block 1619 the real gingival line is determined, as shown in FIG. 26. The location of the final position of gingival zeniths 2140 can be determined. The inferior border of the upper 1940 can also be determined. The distance between the gingival zenith 2140 and the inferior border of the upper lip 1940 may also be determined. The calculated distances can be compared to acceptable gingival distances, as discussed above, and the final orthodontic position of the patient's teeth may be adjusted such that the distance is within a target range or below a target value.

Figure 27:
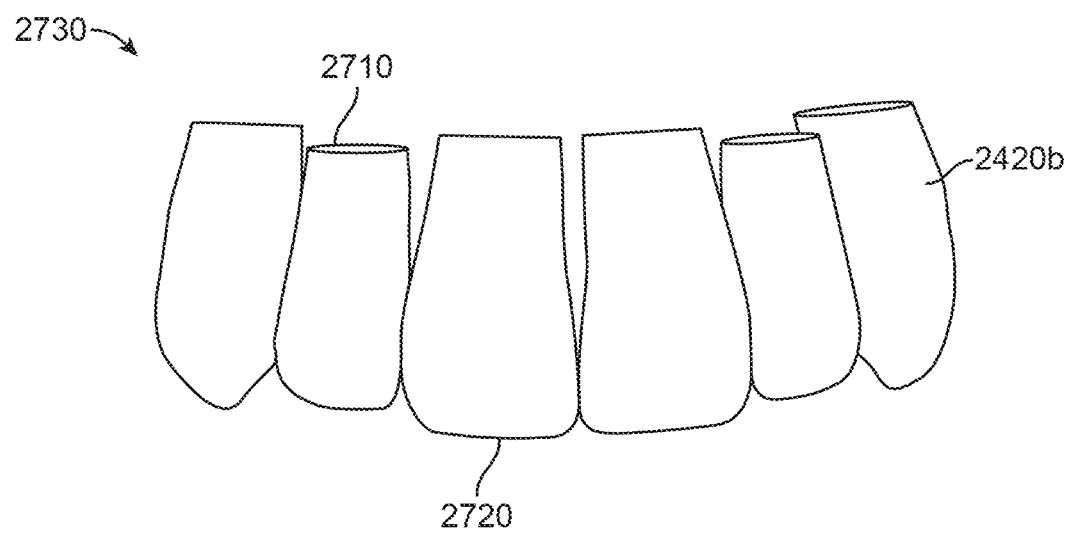
FIG. 27 depicts the placement of restorative objects in a 3D bite model of a patient, in accordance with one or more embodiments herein.

At block 1620 restorations from a tooth library are placed on the 3D bite model. FIG. 27 shows restorations from the tooth library 2710 that can be placed on the 3D bite model for creating the final 3D bite model. The initial reference points for the placement process can include, but are not limited to, the incisal edge 2720, the gingival line 2710, the line that demarcates the inter-canine width 2420a and 2420b at the most distal points on the buccal surfaces of the upper canines, RED percentages, and central incisor proportions. In some embodiments, the 3D tooth models from the tooth library are idealized or generic shapes of teeth. The shapes of these tooth models may be applied to the 3D bite model of the patient to aid in determining the shape of a restorative object to be used on the patient's teeth.

Figure 28:
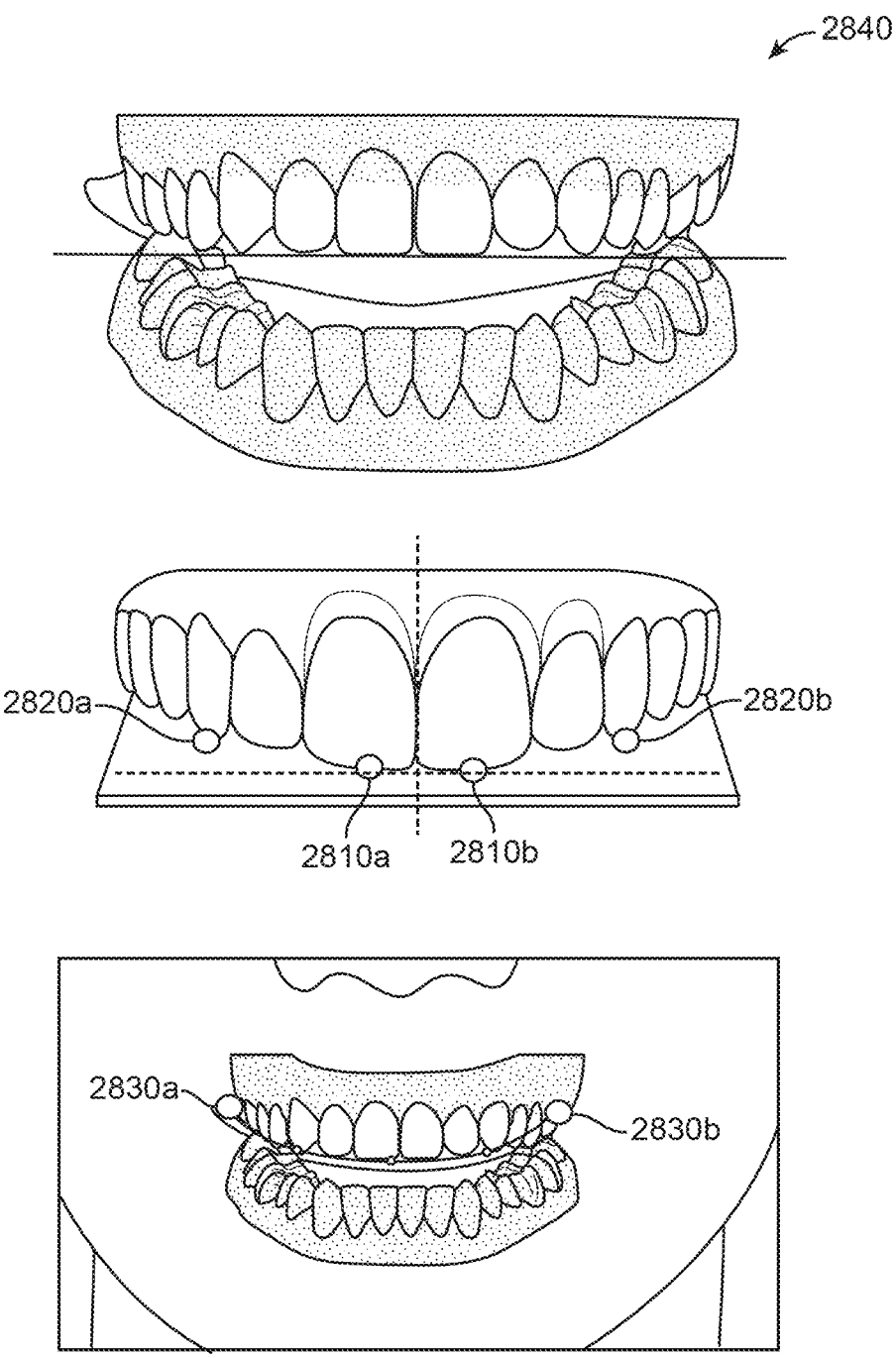
FIG. 28 depicts the determination of the smile arc of a patient, in accordance with one or more embodiments herein.

At block 1622 the smile arc of the patient's teeth in the final orthodontic position with the restorative shapes is determined. As shown in FIG. 28, the following reference points may be determined: the central incisor edge 2810a and 2810b, the canine cusp 2820a and 2820b, and the lip commissures 2830a, 2830b. The teeth from the tooth library may be modified such that the tooth surface shapes of the 3D bite model 2840 match or more closely match the target reference points for the central incisor edge 2810a and 2810b, the canine cusp 2820a and 2820b, and the lip commissures 2830a, 2830b. Then adjustments are made on the canine tooth such that the length of the central incisor is similar to or equal to the length of the canine. Reference points on the central incisor edge 2810a and 2810b and the canine cusp 2820*a* and 2820*b* can be adjusted via the canine. The arc of the smile can be created with a line intersecting the lip commissure 2830*a*, the canine cusp 2820*a*, the central incisor 2810*a*, the central incisor 2810*b*, the canine cusp 2820*b*, and the lip commissure 2830*b*.

Figure 29:
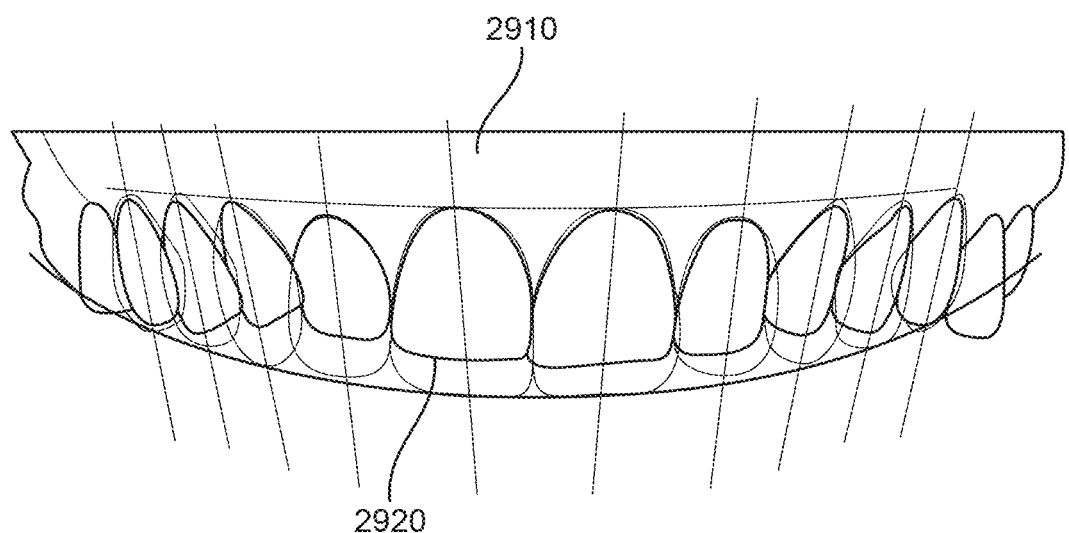
FIG. 29 depicts a method of measuring tooth inclination of a patient, in accordance with one or more embodiments herein.

At block 1624 tooth inclination may be determined and modified. As shown in FIG. 29, reference lines for tooth inclination may be formed as lines extending between or though the gingival zenith 2910 and a center point incisal edge points 2920 or tooth cusps. These reference lines may be used to determine the angle of the tooth to with respect to the dental midline. In some embodiments, the shape or position of the final target positions of the teeth may be adjusted such that the angles of each reference line with the dental midline increases for each tooth away from the dental midline. For example, the angle of the central incisor line is less than the angle of the reference line for the lateral incisor, which is less than the angle of the canine.

Figure 30:
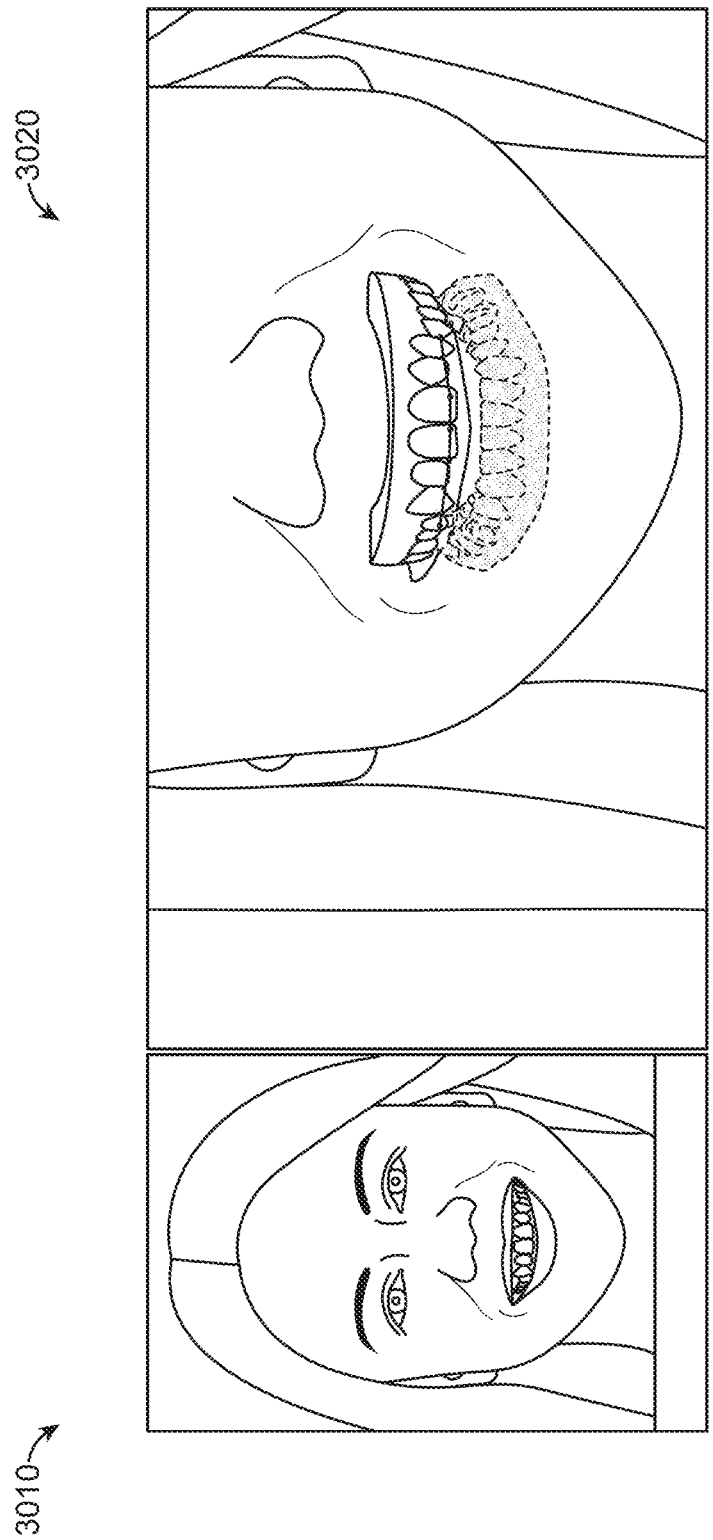
FIG. 30 depicts a method of determining the target final position of a patient's teeth, in accordance with one or more embodiments herein.
Figure 31:
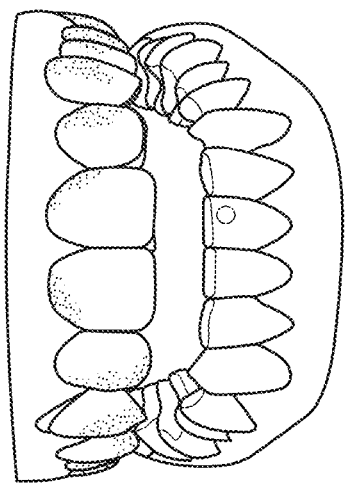
FIG. 31 depicts a 3D bite model integrated into a facial image a target final position, in accordance with one or more embodiments herein.
Figure 31:
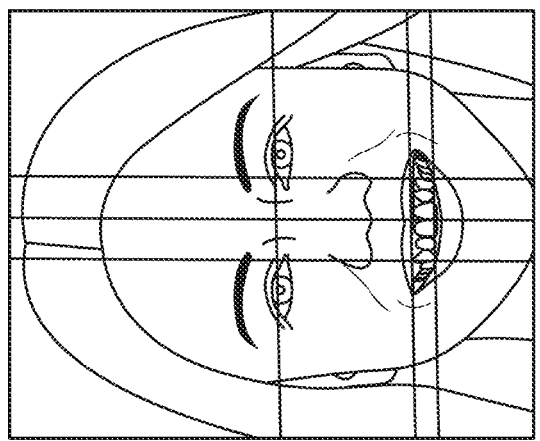

At block 1626 a final or revised final orthodontic position of the teeth is determined and a treatment plan may be regenerated. In some embodiments, the positions of the teeth may be generated and displayed as shown in FIG. 30, which illustrates the 3D bite model 3020 integrated with a facial image of the patient 3010. At block 1628, the final orthodontic and restorative positions of the teeth are evaluated and feedback may be provided for further revisions to the final position and the treatment plan. FIG. 31 illustrates the 3D bite model 3120 after implementation of the treatment plan. The treatment plan can include an evaluation of the restorative overlay, a tooth mass reduction assessment, and an assessment of restorative option versus orthodontic solutions. The final composite image 3110 can include the integrated view of the 2D image of the patient and the 3D bite model. The final composite image 3110 and the final 3D bite model 3120 can be showcased to the patient.

Figure 16B:
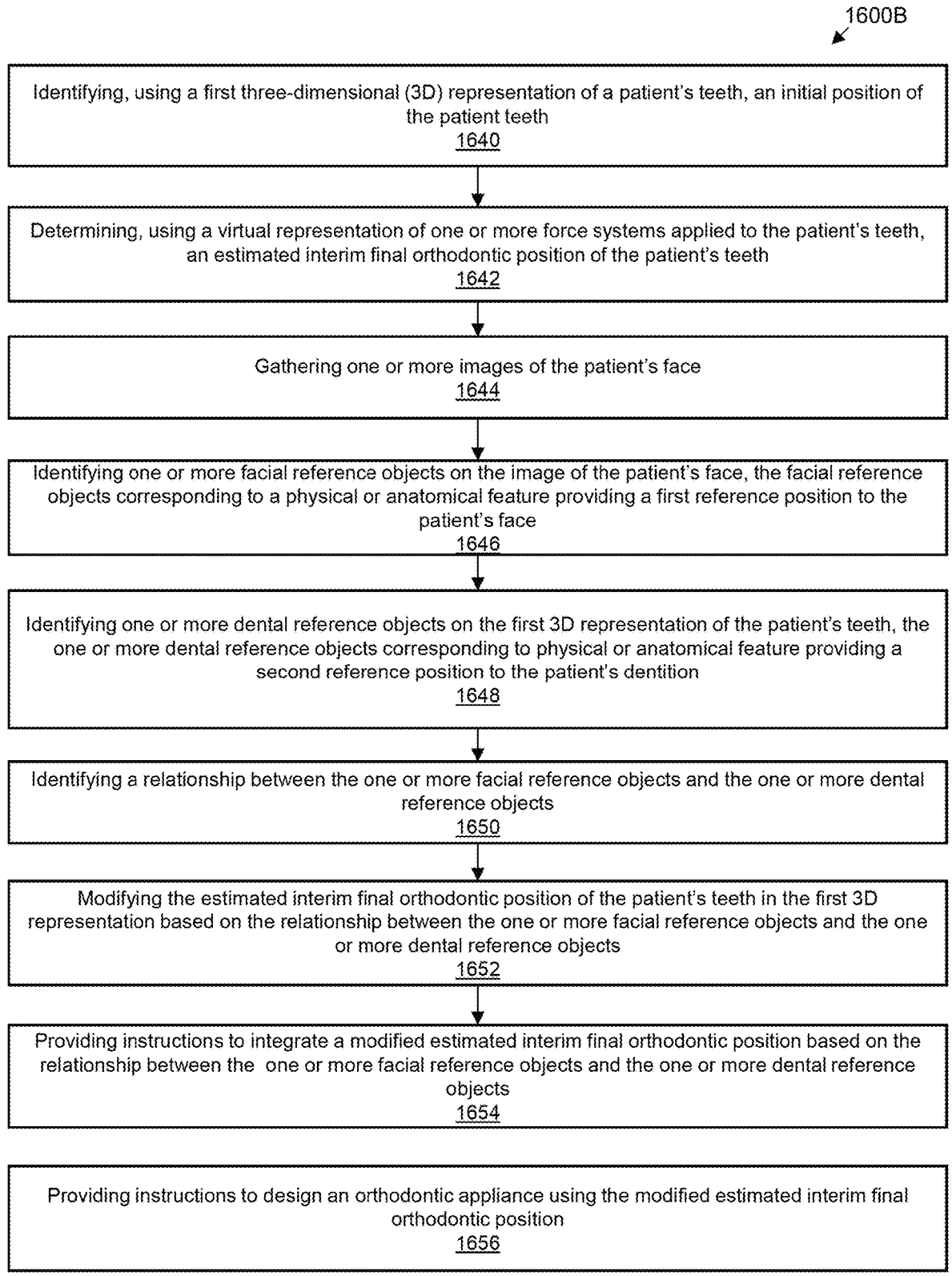
FIG. 16B depicts a method for virtually representing a treatment outcome using automated detection of facial and dental reference objects, according to some embodiments.

FIG. 16B depicts a method 1600B for virtually representing a treatment outcome using automated detection of facial and dental reference objects, according to some embodiments. Some or all of the operations in the method 1600B may overlap with method operations discussed in the context of FIG. 16A. At an operation 1640, an initial position of the patient teeth may be identified using a 3D representation of the patient's teeth. The initial position may include the patient's teeth at an initial or at an intermediate stage of an orthodontic treatment plan.

At an operation 1642, an estimated interim final orthodontic position of the patient's teeth may be determined using a virtual representation of one or more force systems applied to the patient's teeth. In various implementations, application of virtual representations of forces and/or torques used as part of the orthodontic treatment plan may be modeled against the 3D representation of the patient's teeth.

At an operation 1644, one or more images of the patient's face may be gathered. These images may be gathered from a camera or other image capture device as discussed further herein.

At an operation 1646, one or more facial reference objects on the image of the patient's face may be identified. The one or more facial reference objects may correspond to a physical or anatomical feature providing a first reference position to the patient's face. In some implementations, a geometrical analysis of the image of the patient's face may be performed, where desired RED proportions and/or anterior tooth widths are determined. The patient's "face type" may be determined.

At an operation 1648, one or more dental reference objects on the first 3D representation of the patient's teeth may be identified. The dental reference objects may correspond to physical or anatomical feature providing a second reference position to the patient's dentition.

At an operation 1650, a relationship between the one or more facial reference objects and the one or more dental reference objects may be identified. The relationship may involve measurement of distances between the facial reference object(s) and the dental reference object(s). In some implementations, the relationship may involve alignment of the facial reference object(s) and the dental reference object(s).

At an operation 1652, the estimated interim final orthodontic position of the patient's teeth in the first 3D representation may be modified based on the relationship between the one or more facial reference objects and the one or more dental reference objects. In some implementations, the modification may only occur if the relationship meets or is not greater than a specified threshold. As an example, the modification may only occur if a distance between the facial reference object(s) and the dental reference object(s) meets or does not exceed a specified distance threshold.

At an operation 1654, instructions to integrate a modified estimated interim final orthodontic position based on the relationship between the one or more facial reference objects and the one or more dental reference objects may be provided. In some implementations, the facial reference objects may be used as the basis of a target for the dental reference objects. Examples include setting a dental midline that matches a facial midline; setting an incisal edge position that matches a location of the inferior boarder of the upper lip at the facial midline; setting an incisal edge position that matches a location of the superior boarder of the upper lip at the facial midline; and setting a gingival zenith of a central incisor that aligns with the inferior boarder of the upper lip at the facial midline. At an operation 1658, instructions to design and/or manufacture an orthodontic appliance using the modified estimated interim final orthodontic position are provided.

Matching a Bite Model with a 2D Image

Figure 32:
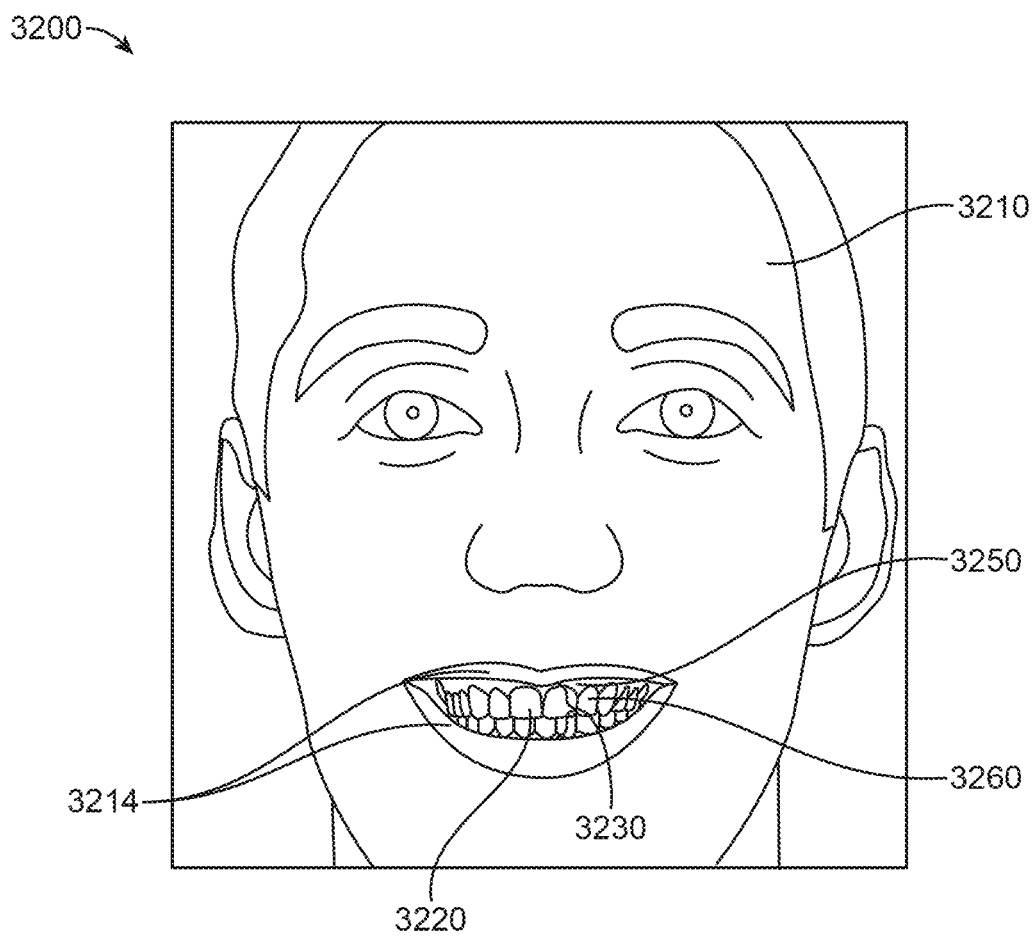
FIG. 32 illustrates a composite patient image, in accordance with one or more embodiments herein.

FIG. 32 depicts a composite image 3200 of a 2D image of the face of a person 3210 and a 2D image of a 3D bite model 3220. In the 2D image of the patient, the patient can have an open mouth. The opening of the mouth 3230 is demarcated by edge of the lips 3214. The teeth 3260 and the gingiva 3250 of the 3D bite model 3220 can be shown in the opening of the mouth 3230.

The 3D bite model 3220 can be a 3D digital visualization of the teeth, and it can be used to visualize the shape and position of the teeth in a current state or in a future state wherein the future state can be the shape and position of the teeth during or after undergoing a treatment plan to reposition the teeth of the patient. The treatment plan can include orthodontic measures for correcting malocclusions and other orthodontic issues with the patient's teeth, for example correcting an overbite, an underbite, tooth rotation, or tooth tipping. In some embodiments, the treatment plan can include restorative measures including but not limited to installing a crown, a veneer, or bridge.

The composite image 3200 can be used to provide facial context to the visualization of the 3D bite model. In some embodiments, the composite image 3200 provides facial contextual visualization of the 3D model of the shape and position of the patient's natural teeth. In some embodiments, the composite image can provide facial visualization of the 3D model of the shape and position of the teeth undergoing the treatment plan. Such contextual information aids in the evaluation of the dental treatment plan and in determining the final position of the patient's teeth, for example when used with the treatment planning processes and systems described herein. Contextual information also aids in the patient's understanding of the treatment plan and in making an informed treatment decision.

A composite image of a 2D image of the face of a person and a 2D image of a 3D bite model (3D bite model) can create an unnatural look. This unnatural look may be described by the uncanny valley effect, which is a hypothesis that describes the adverse human emotional response to human replicas. Human replicas that appear nearly, but not quite like human beings elicit feelings of eeriness and revulsion. In contrast, human replicas that are distinctly different than humans do not elicit this negative emotional response. Composite images that include 3D bite models can seem almost, but not entirely, human when viewed in the context of a natural human face. Therefore, some composite images elicit feelings of unease in the dental professional or in the patient. In some embodiments, an unnatural look can be caused by aesthetic differences between the natural teeth and the 3D bite model, including but not limited to, 3D teeth features, blur effect, teeth color, gingiva color, intensity of whiteness, intensity of red color, intensity of green color, and intensity of blue color. In order to aid in reducing the unpleasant reactions, the composite can be made to have a more seamless integration of the 3D bite model into the 2D image of the patient. As described below, systems and methods may be implemented to aid in matching the 3D bite model with the 2D image of a patient. Various features of the 3D bite model can be controlled to aid this matching. Some embodiments of matching a 3D bite model with a facial image may use neural networks or machine learning algorithms, as shown and described with respect to FIGS. 36A and 36B.

Figure 33:
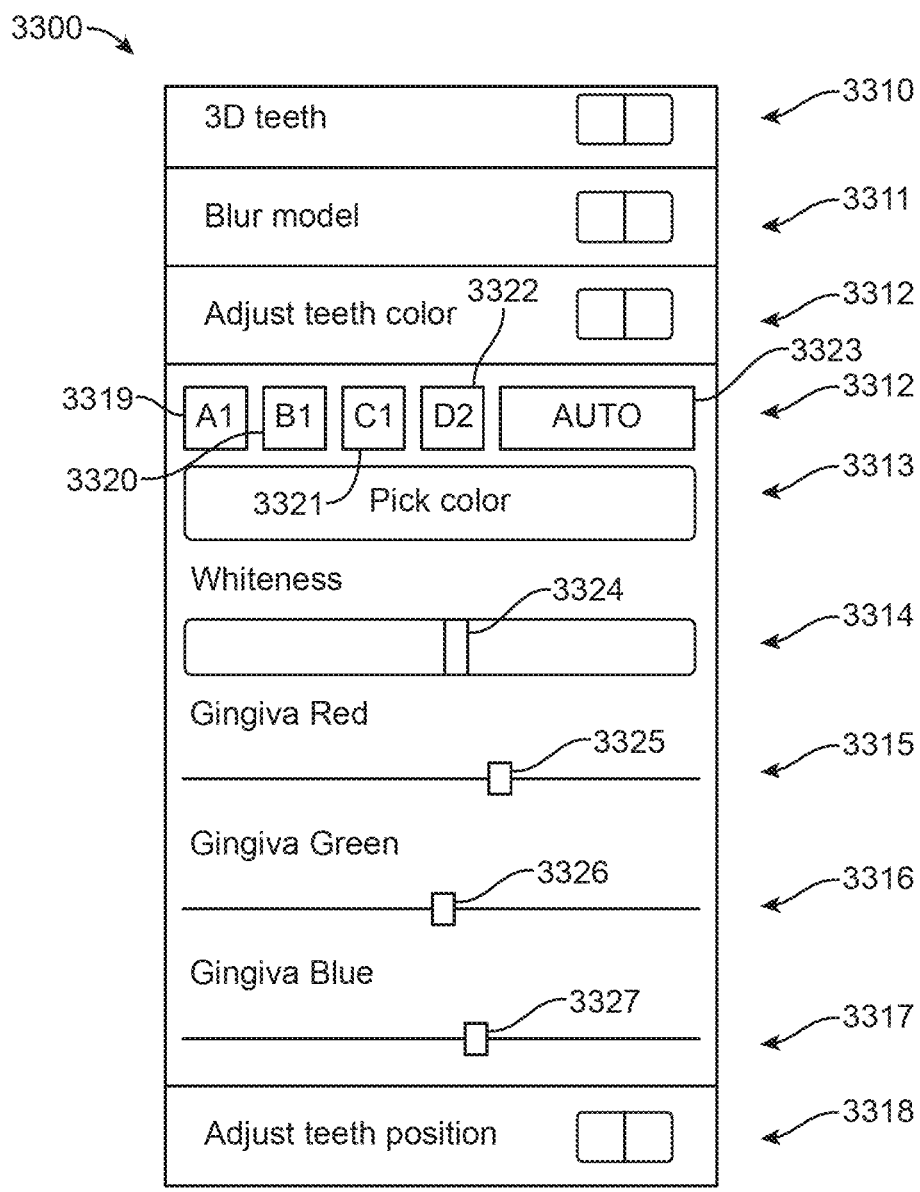
FIG. 33 illustrates a controller for adjusting the features of an image, in accordance with one or more embodiments herein.

FIG. 33 illustrates a controller 3300 that may be a digital user interface for adjusting features of the 3D bite model 3220. The controller 3300 may be part of the system 400 shown and described above with reference to FIG. 4. The controller 3300 may include toggle switches and scaling bars that aid in adjusting features of the 3D bite model 3220. The controller 3300 can be used to control one or more of a plurality of features of the 3D bite model image. One of a plurality of controllable features can be to adjust the 3D tooth effect, and the 3D tooth effect can be turned on or otherwise adjusted via, for example, a switch, such as the 3D teeth feature toggle switch 3310. One of a plurality of controllable features can be to create a blur effect, and the blur effect can be turned on or otherwise adjusted via a switch, such as the blur model toggle switch 3311. One of a plurality of controllable features can be used to adjust teeth color, and the teeth color can be adjusted by or otherwise adjusted via a switch, such as the adjust teeth color toggle switch 3312. One of a plurality of controllable features can be used to adjust teeth color options (indicated by the pick color bar 3313) using the press-button located in bar 3312 a dental professional may select a location on the 2D image for use in coloring the 3D bite model. The tool color may also be adjusted using preselected color options, which may be standard dental colors. For example, the color options may include an A1 color 3319, a B1 color 3320, a C1 color 3321, a D2 color 3322, and an automatic color 3323 chosen, for example, based on the colors of the teeth of the 2D image of the patient. One of a plurality of controllable features can be to adjust the intensity of whiteness, and the intensity of whiteness can be adjusted or otherwise selected by moving the slider 3324 along the scale 3324 of the whiteness adjuster 3314.

One of a plurality of controllable features can also include adjustments and selection of the red, green, and blue color balance of the teeth of the 3D bite model. The controller 3300 includes a red adjuster 3325, a green adjuster 3326, and a blue adjuster 3327 in respective color selectors 3315, 3316, 3317. The adjusters and selectors may change the color intensity or balance of one both of the teeth and gingiva. As shown in FIG. 33, the color adjusters and selectors adjust the color balance of the gingiva.

A quality metric, such as an integration quality metric, may quantitatively describe the difference or degree of agreement between an integrated composite image and a 2D image of a patient. In some embodiments, the quality metric is defined by a scale that corresponds to the degree of agreement or difference between the integrated composite image or the 3D bite model of the integrated composite image and the 2D image of the patient or a portion of the 2D image of a patient, such as the image of the teeth and gingiva of the patient. The scale of the quality metric may be a closed or open ended range. For example, in an open ended range the metric may start at 0, indicating a perfect match between the composite image and the image of the patient, and increase without limit based on the degree of agreement, with increasingly high numbers indicating increasingly poor match or agreement between the images. In a closed ended range 0 may indicate a perfect match while 1, 10, or 100, may indicate a complete mismatch between the images or a mismatch above a predetermined threshold between the images.

Figure 34:
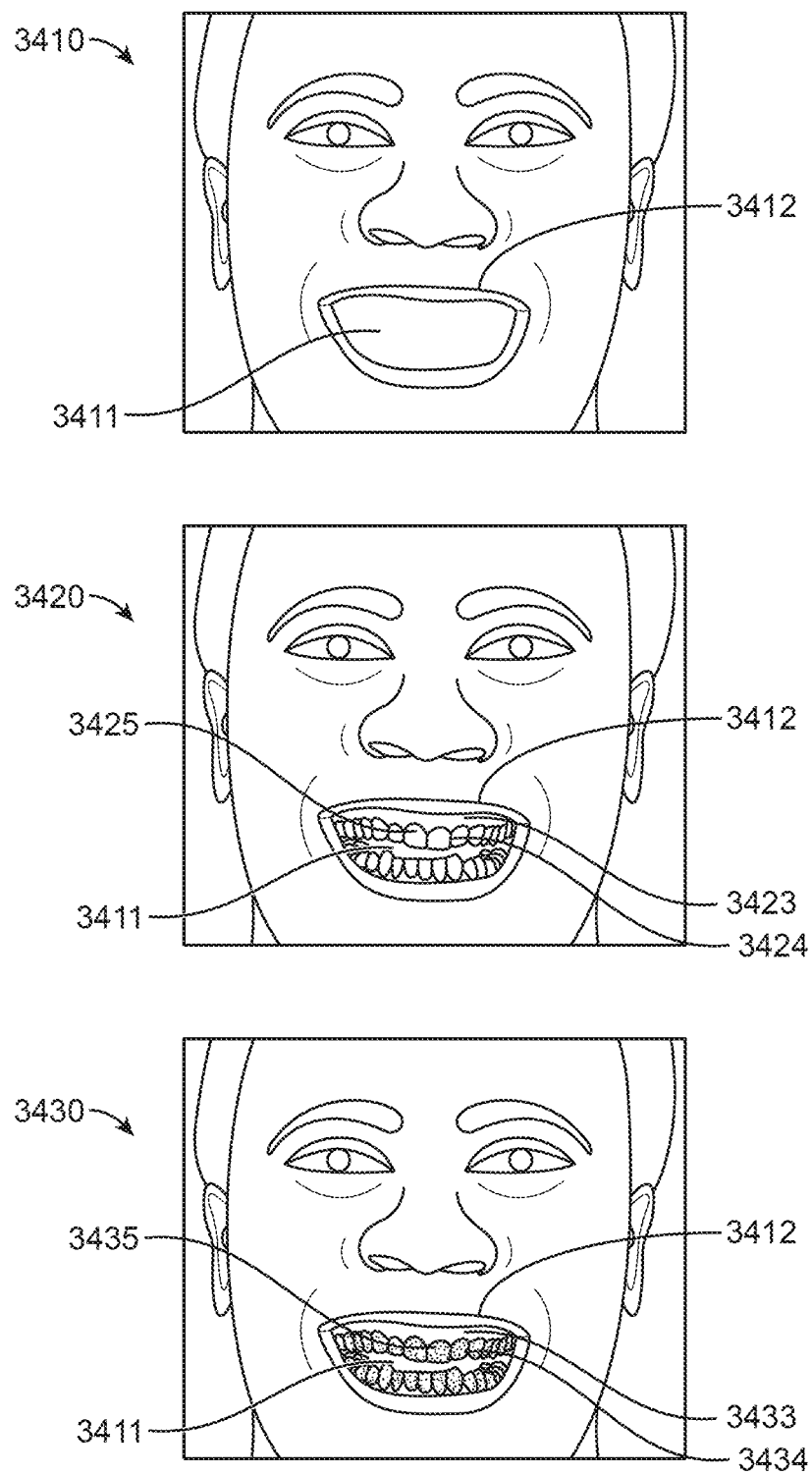
FIG. 34 illustrates a 3D bite model in the composite view, in accordance with one or more embodiments herein.

FIG. 34 illustrates a 3D bite model in the composite view with various degrees of match between the respective composite view 3410, 3420, 3430 and a reference 2D image of the patient. The matching may be performed with the controller, for example as described above with reference to FIG. 33 or according to the method 3500 described below with reference to FIG. 35, or another method, such as that shown and described with reference to FIGS. 36A and 36B. The composite image 3410 shows an example of a composite image with a high degree of mismatch and lack of agreement with a reference image. In such an image, the mouth opening 3411, delineated by the inner edges of the lips 3412 bear little to no resemblance with the mouth, teeth, and gingiva of an image of the patient. The quality metric of such a composite image may be high, such as greater than a threshold value.

The composite image 3420 shows an example of a composite image with a moderate degree of mismatch and lack of agreement with a reference image. In such an image, the mouth opening 3411, delineated by the inner edges of the lips 3412 includes a colored 3D bite model 3425 of the patient within the mouth opening 3411 with basic color and shading added such that the teeth 3424 and gingiva 3423 are apparent, but significant and noticeable differences may still exist between the 2D image of the patient. The quality metric of such a composite image may be high, such as greater than a threshold value, but lower than that of the composite image 3410.

The composite image 3430 shows an example of a composite image with a low degree of mismatch and high degree of agreement with a reference image. In such an image, the mouth opening 3411, delineated by the inner edges of the lips 3412 includes a colored 3D bite model 3435 of the patient within the mouth opening 3411 with accurate color and shading added such that the teeth 3434 and gingiva 3433 include few, if any, noticeable differences between the 3D bite model 3435 and the image of the patient. The quality metric of such a composite image may be low, such as zero, or less than a threshold value of acceptable agreement.

Figure 35:
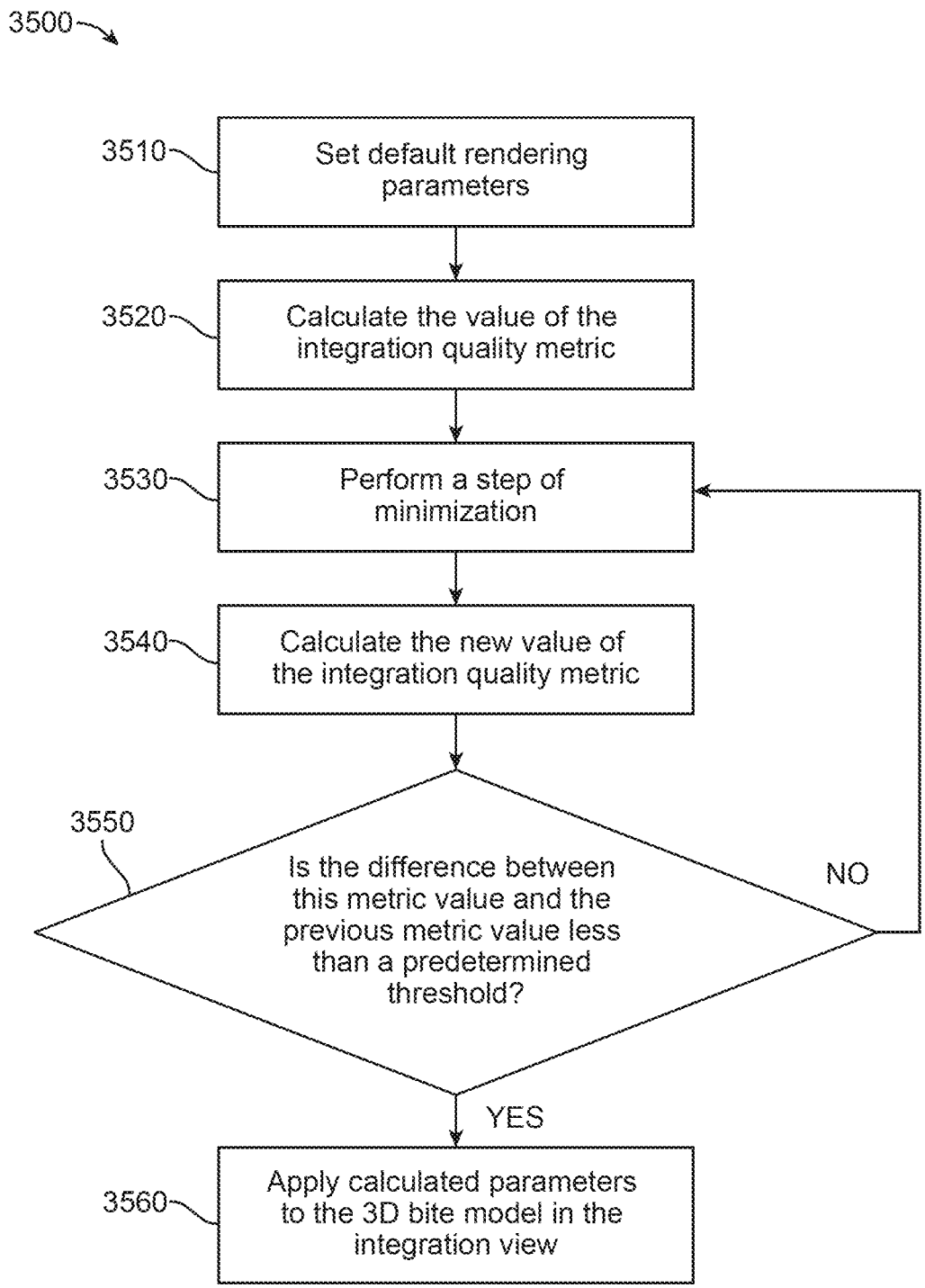
FIG. 35 illustrates a method of matching the 3D bite model with a reference image, in accordance with one or more embodiments herein.
Figure 36:
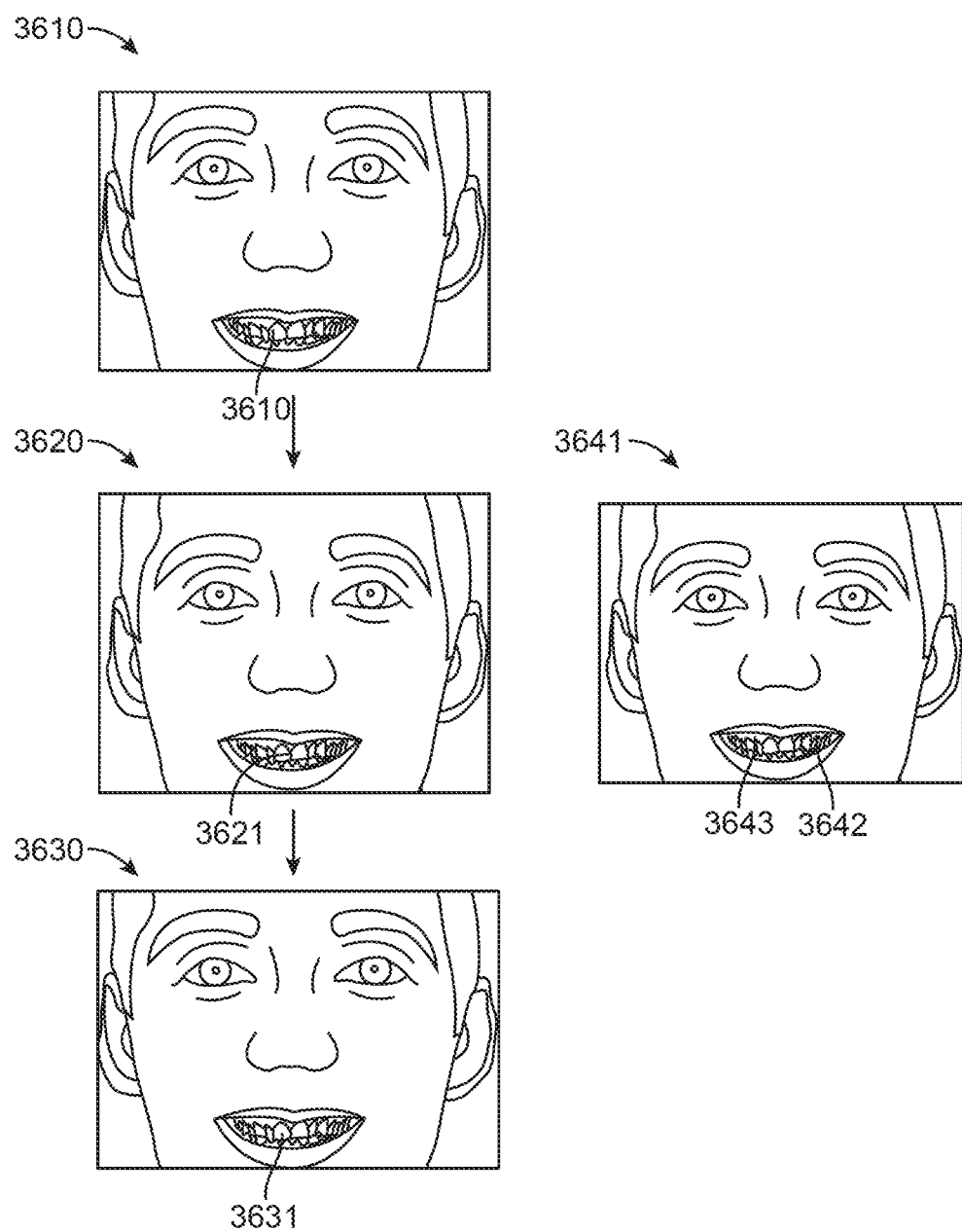
FIG. 36 illustrates a method of matching the 3D bite model with a reference image, in accordance with one or more embodiments herein.

FIGS. 35 and 36 illustrate a method of matching the 3D bite model with the 2D image of a patient. The process for obtaining the 3D bite model in integration view 3500 can be based on a comparative analysis whereby there is a minimization of the differences between a first image and a second image. The minimization process may reduce the quality metric to at least a threshold value of acceptance. FIG. 36 shows a reference 2D image 3641 of the patient, including their natural teeth 3642 and natural gingiva 3643, along with three images of a composite image, including a composite image 3610 at an initial stage, a composite image 120 at an intermediate stage of processing, and a composite image 3630 at a final stage of processing.

The process for obtaining the 3D bite model 3500 may include multiple steps and may be iterative. At block 3510 the default settings for the rendering parameters are set. Such default parameters may serve as the initial conditions of the matching process. The rendering parameters can be derived from the parameters of natural teeth 3642 and natural gums 3643 in the 2D image 3641. Subsequently, as depicted in block 3520, the value of the integration quality metric can be determined by comparing the composite image to the 2D image of the patient. The comparison between the composite image 3610 and the 2D image 3641 of the patient may include a pixel by pixel comparison of the differences between the pixels in the composite image and the corresponding pixels in the same location in the 2D image of the patient.

In some embodiments, the quality metric, determined based on the differences in the pixels, may be the Mean Absolute Error (MAE) of the pixels compared between the two images. In some embodiments, the quality metric, determined based on the differences in the pixels, may be the Mean Squared Error (MSE) of the pixels compared between the two images. The difference in the pixels may include the difference between one or more of the red, green, blue, and luminance values of each pixel. In some embodiments, the quality metric may be based on a peak signal-to-noise ratio, such as the PSNR-HVS-M or PSNR-HA methods.

In some embodiments, other methods for calculating the quality metric may be used. For example, databases of scored images may be used in the quality metric, for example, a metric comparison using the TID2008, TID2013, LIVE, Toyama, IVC, CSIQ, and others may be used. In some embodiments, perceptual visual quality metrics such as FSIMs, SSF, PSNR-HAc, SR-SIM, BMMF, and others may be used. The metric comparison used in calculating the quality metric may include the use of Spearman's correlation, the Kendall correlation, or others.

In block 3530 a step of minimization may be performed where the parameters, such as the rendering parameters, of the 3D bite model are adjusted to aid in reducing the quality metric to below a threshold value. The parameters may include teeth color, gingival color, material properties and light properties. Color parameters may include color temperature, red, green, and blue color intensities, saturation, luminance of the teeth and gingiva. Material parameters may include surface texture modifications such as surface textures and surface reflectivity. Light parameters may include shading (such as the variation of shading on the teeth between the front teeth, which are exposed more directly to light, and the back teeth, which are less exposed to outside light due to the light blockage by the lips and cheeks), light source location, and type, such as a point source or non-point source of light. The process alters these parameters in such a way as to minimize the quality index. In some embodiments, as part of the minimization process, a Monte Carlo method may be implemented wherein various parameters are modified and an estimation of their effect on the quality index is determined. The parameters of the 3D bite model may then be modified based on the results of the Monte Carlo analysis.

At block 3540 the new value of the integration quality metric may be calculated based on the image of the 3D bite model generated using the revised parameters. The interim composite image 3620 shows the interim integrated 3D bite model 3641 with the interim parameters applied. At block 3550 the quality metric is compared to a threshold value. If the quality metric is acceptable based on the threshold value, then the process proceeds to block 3560. The quality metric may be acceptable if the value of the quality metric is below the threshold value. If the quality metric is not acceptable based on the threshold value, then another step of minimization and calculation of the quality metric may be performed as in blocks 3530 and 3540. As a result of this process, the 3D bite model may more closely match that of the image of the patient. In some embodiments, the 3D bite model may have parameters that are similar to or the same as the parameters of the 2D image 3641. A final composite image 3630 may be generated based on applying the parameters determined earlier in the process to the 3D bite model 3631 such that the 3D bite model 3631 is matched to the colors of the natural teeth 3642 of the 2D image 3641 of the patient. Such a process may result in a seamless and natural integration of the 3D bite model into the image of the patient.

Figure 36A:
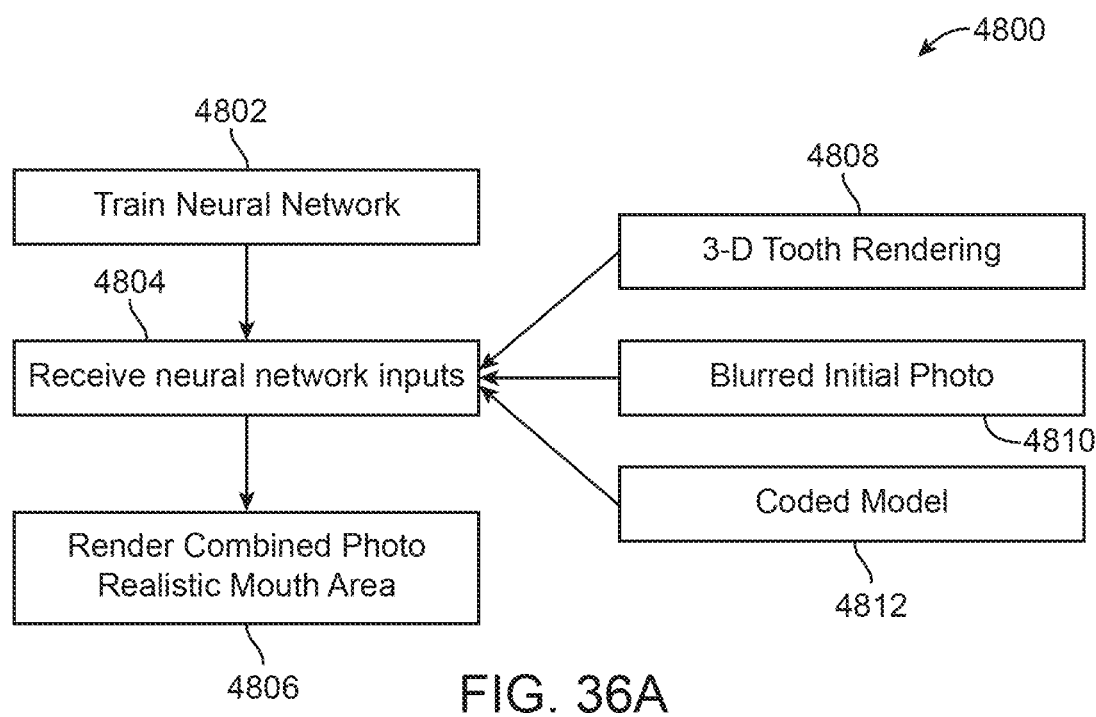
FIG. 36A depicts a process of rendering a realistic composite image of patient's face and a model of a patient's teeth, in accordance with one or more embodiments herein.

In some embodiments, neural networks, such as generative adversarial networks or conditional generative adversarial networks may be used to integrate a 3D model of teeth in a final position with a facial image of a patient and match the colors, tones, shading, and other aspects of the 3D model with a facial photo. FIG. 36A depicts an embodiment of a method 4800 of integrating a 3D model of a patient's teeth in a clinical final position with a facial image of a patient. At block 4802, the nural network is trained using facial images. In some embodiments, the facial images may include images of peoples faces having a social smiles. In some embodiments, the facial images may include facial images of patient's teeth before orthodontic treatment. During training, patient's teeth and their contours may be identified. For example, each tooth may be identified by type (e.g., upper left central incisor, lower right canine). Other aspects and features of the image may also be identified during training, such as the location and color of the gingiva, the color of the teeth, the relative brightness of the surfaces within the mouth, and others.

Figure 36B:
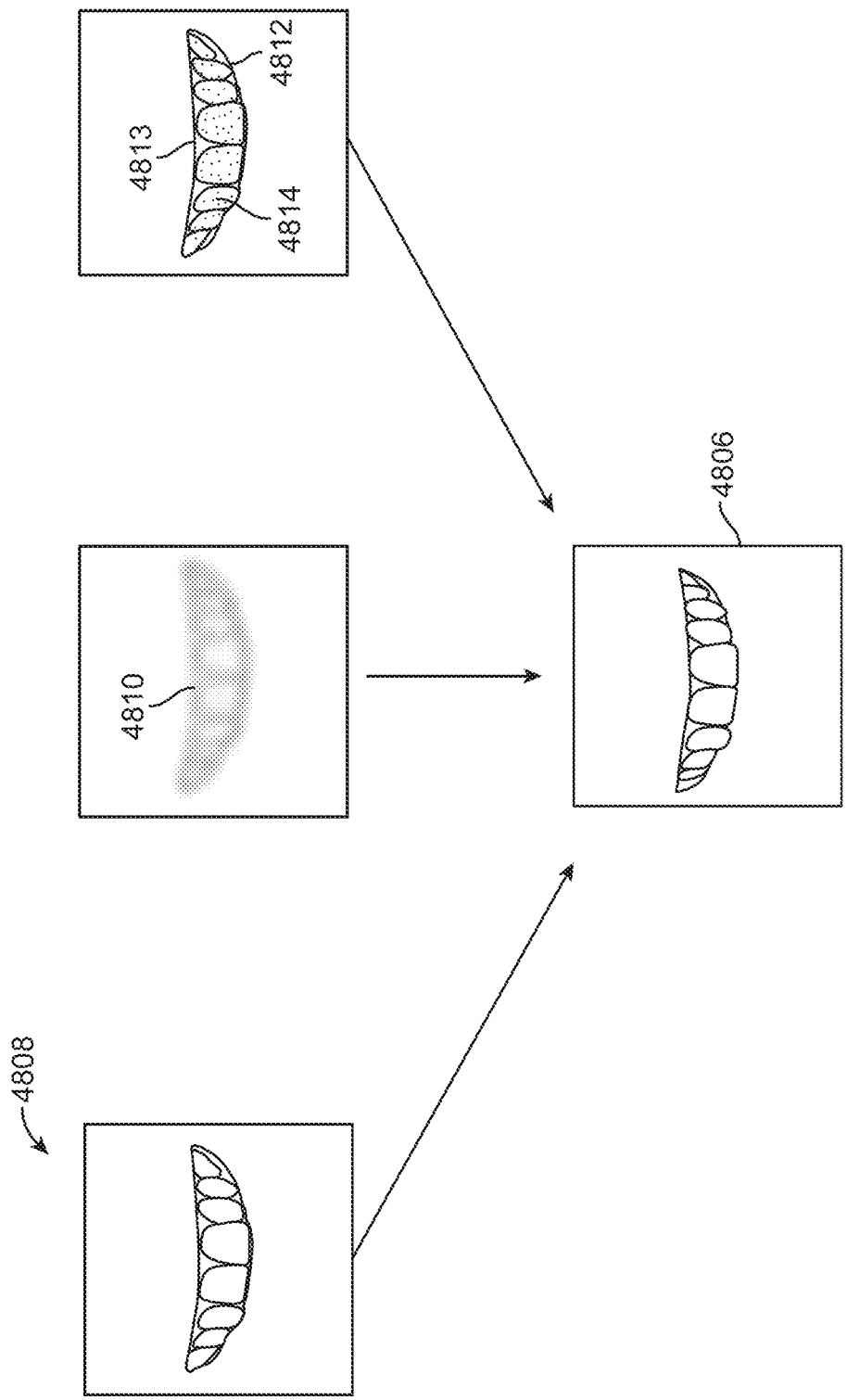
FIG. 36B depicts a process of rendering a realistic composite image of patient's face and a model of a patient's teeth, in accordance with one or more embodiments herein.

Referring to FIGS. 36A and 36B, after training, the neural network receives inputs at block 4804 for use in generating a realistic rendering of the patient's teeth in a clinical final position. In some embodiments, the inputs may include one or more of an image of a rendering of a 3D model of the patient's teeth in a clinical final position or a 3D rendered model of the patients teeth in the clinical final position 4808, the clinical final position determined, for example, according to an orthodontic treatment plan, a blurred initial image of of the patient's teeth 4810, and a color coded image 4812 of the 3D model of the patient's teeth in the clinical final position.

The image of a rendering of a 3D model of the patient's teeth in a clinical final position or the 3D rendered model of the patients teeth in the clinical final position 4808 may be determined based on the clinical orthodontic treatment plan for moving the patient's teeth from the initial position towards the final position, as described above. The image or rendering 4808 may be generated based on the imaging perspectives determined as described with respect to FIG. 13E. For example, one or more of the imaging distance, the focal length of the imaging system, and the size of the patient's teeth in the initial facial image may be used to generate the image or rendering.

The blurred image of the patient's teeth 4810 may be generated using one or more blur algorithms, such as a Gaussian blur algorithm. The Gaussian blur preferably has a high radius, for example, a radius of at least 5, 10, 20, 40, or 50 pixels. In some embodiments, the blur is sufficiently great that the tooth structure is not longer readily apparent to a human observer.

The coded model of the patient's teeth 4812 may be a red-green-blue (RGB) color coded image of a model of the patients teeth, with each color channel corresponding to a different quality or feature of the model. For example, the green color channel, which may be an 8-bit color channel indicates the brightness of the blurred image 4810 on a scale of 0 to 255 as, for example, overlaid on the 3D model.

The red color channel may be used to differential each tooth and the gingiva from each other. In such an embodiment, the gingiva may have a red channel value of 1, the left upper central incisor may have a red value of 2, the right lower canine may have a red channel of 3, the portions of the model that are not teeth or gingiva might have a red channel value of 0, and so on, so that the red channel value of each pixel identifies the dental anatomy associated with the pixel.

The blue color channel may be used to identify the angle of the teeth and/or gingiva with respect to the facial plane. For example, at each pixel location the angle normal of the surface of the dental structure, is determined and a value between 0-255 (for 8-bit color channels) is assigned to the pixel. Such information allows the neural network to, for example, model light reflectivity from the dental surfaces.

At block 4806 the neural network uses the inputs and its training to render a image realistic image of the patient's teeth in a final position. This photo realistic image is then integrated into the mouth opening of the facial image and an alpha channel blurring is applied.

The method 4800 provides a significantly more realistic integration of the 3D model with the facial image than previous methods. This pushes the realism beyond the uncanny valley.

Tooth Mass Reduction for Restorative Objects

Patients can display symptoms of malformed teeth or injured teeth. Malformed or injured teeth may be chipped, broken, worn down through grinding or other means, or simply malformed.

A restorative object can be used to treat one or more injured or malformed teeth. A restorative object, such as an artificial tooth or artificial part of the tooth, restores or corrects the shape of an injured or malformed tooth. In some embodiments, a restorative object may be a crown, which is a tooth-shaped cap that is placed over a tooth to restore its shape and size and improve its appearance. In some embodiments, the restorative object may be a veneer, which is a thin shell of material that covers the front surface of a tooth. The restorative object can have a predetermined shape and size. In order to aid the fitting of the restorative object over the tooth, the tooth may undergo tooth mass reduction where a portion of the tooth is removed to provide a mounting surface to receive the restorative object.

Different processes for applying restorative objects may use differing amounts of tooth reduction. For example, applying a veneer to a tooth may result in less tooth mass reduction than applying a crown. Differing amounts of tooth mass reduction may also be seen between different applications of similar restorative objects. For example, applying a veneer to a tooth in a first position may involve removing more tooth mass than applying a veneer to the same tooth, but in a different position. Evaluating tooth mass reduction for restorative objects in different positions may aid in reducing or minimizing the amount of tooth mass loss due to the application of restorative objects.

Figure 37:
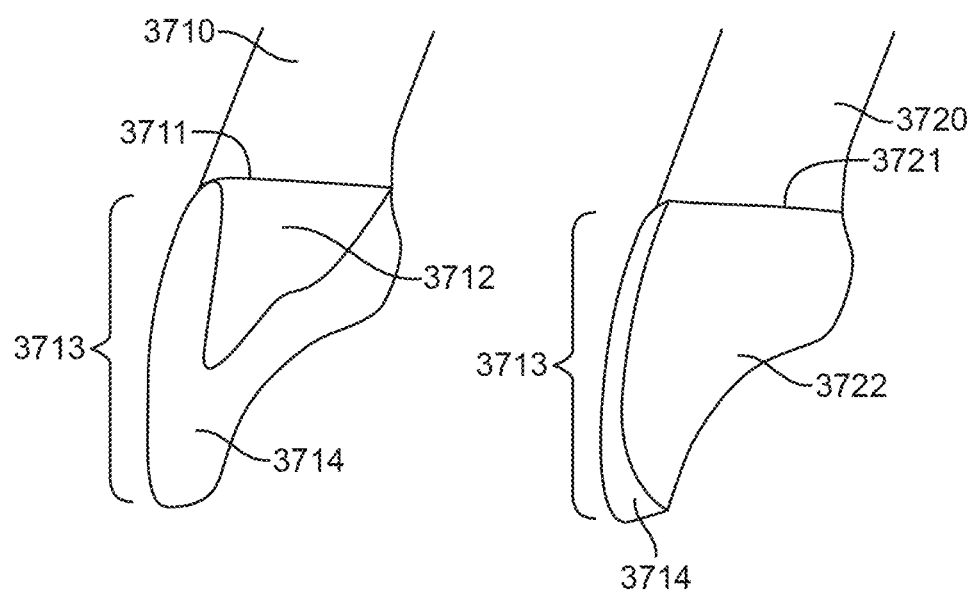
FIG. 37 illustrates the tooth mass reduction for restorative objects, in accordance with one or more embodiments herein.

FIG. 37 depicts an illustration of teeth with restorative objects applied thereon. In some embodiments, such as those shown in FIG. 37, the root 3710 and 3720 of the tooth extending to the neck 3711 and 3721 may remain intact. As shown in FIG. 37, a prosthetic crown 3714 may be applied to a reduced tooth 3712 or a veneer 3714 may be applied to a reduced tooth 3722.

Figure 38:
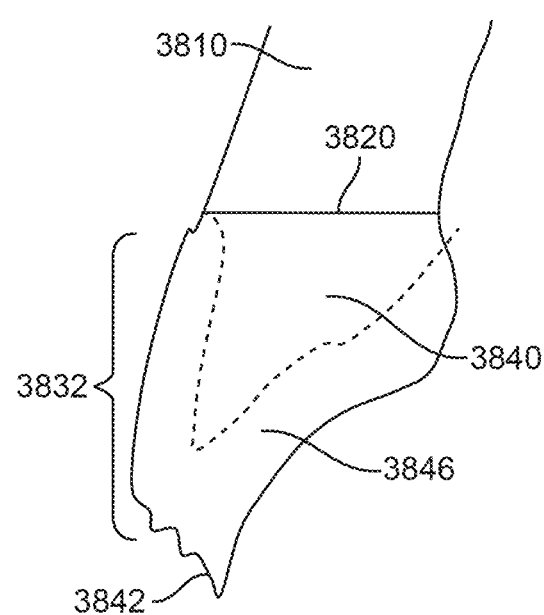
FIG. 38 depicts a method of determining of tooth mass low reduction, in accordance with one or more embodiments herein.

FIG. 38 depicts how the amount to tooth mass loss is determined. To aid in fitting the restorative object to a tooth, the tooth may undergo tooth mass (or volume) reduction where a portion of the tooth is removed and the remaining tooth is a tooth with a reduced mass or volume. As shown in FIG. 38 the crown 3832 of the tooth is chipped or otherwise broken. The broken line represents the reduced portion of the crown 3840 after tooth mass reduction. In this embodiment, the remaining reduced portion 3840 serves as the mount for the restorative object, such as a prosthetic crown. The mass or volume 3846 removed from the tooth in preparing the tooth for the restorative object is determined, for example, by subtracting the volume of the reduced crown 3840 from the volume of the natural crown 3842.

In some embodiments, the removed tooth mass is healthy tooth mass but is removed in order to create space for the addition of the restorative object. It may be beneficial to the patient if the amount of removed tooth can be reduced or minimized. The amount of tooth mass that is removed can be determined with a 3D bite model during the treatment planning process. The position and shape of the restorative object can be visualized with the integration of the restorative object on the 3D bite model.

Figure 39:
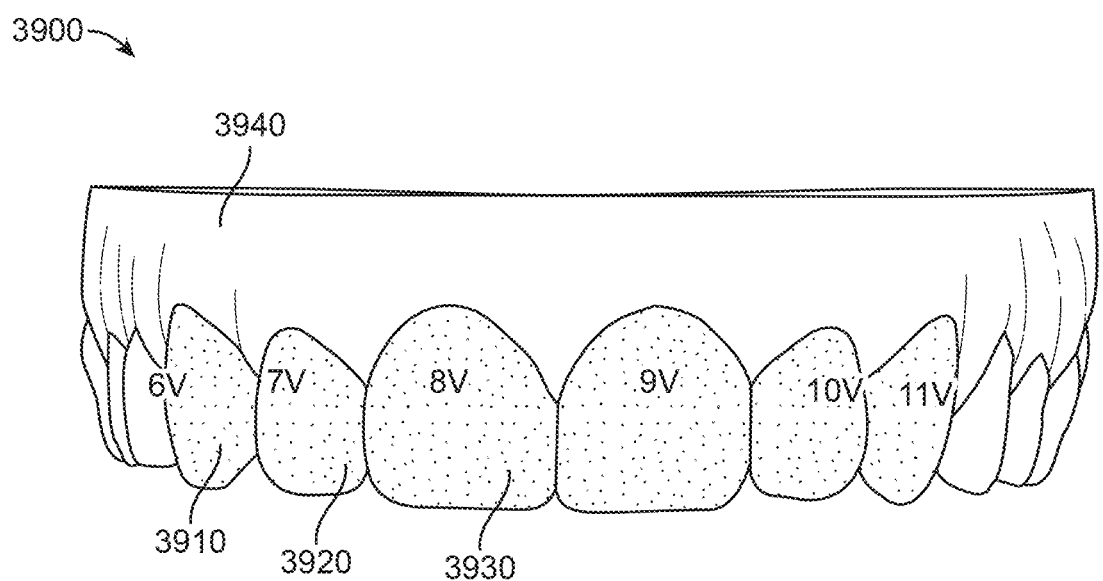
FIG. 39 depicts a 3D bite model with restorative objects, in accordance with one or more embodiments herein.

FIG. 39 illustrates a 3D bite model 3900 that depicts teeth, gingiva 3940, a restorative object on the right canine 3910, a restorative object on the right lateral incisor 3920, and a restorative object on the right central incisor 3930. The visualization of the restorative object in the 3D bite model may be useful in determining the shape or position of the restorative object on the patient's natural teeth. The ability to determine the shape of the restorative object before dental work, such as orthodontic corrections, may allow for tooth mass reduction analysis, where the amount of tooth loss is determined for various restorative object shapes on teeth in one or more final orthodontic positions. The restorative object shape that uses the least tooth mass loss may be beneficial to the patient.

Figure 40:
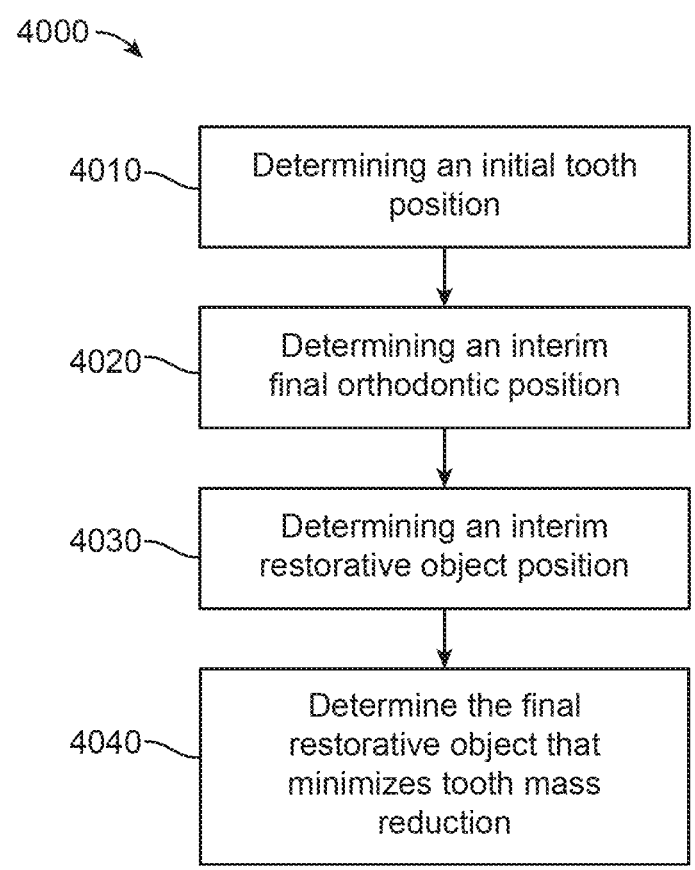
FIG. 40 depicts a method of forming a composite image, in accordance with one or more embodiments herein.
Figure 41:
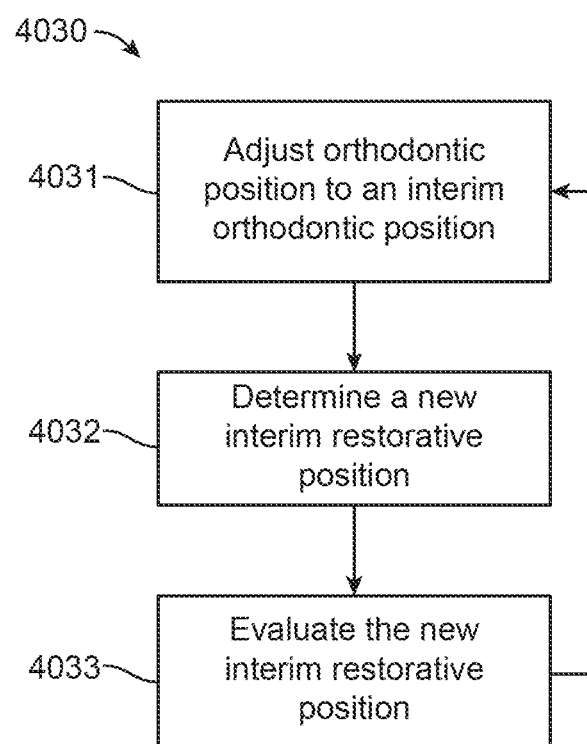
FIG. 41 depicts a method for forming a composite image, in accordance with one or more embodiments herein.

Dental professionals and technicians may modify one or both of the restorative object's placement and the orthodontic final teeth positions to minimize or reduce tooth mass reduction. The 3D bite model can be used to determine a movement a tooth of a patient from a first position and orientation to a second position and orientation as described herein. Computer-based treatment planning can be used to facilitate the design of each tooth trajectory in the treatment plan, as describe above with reference to FIGS. 1-4. During the treatment planning process the position and shape of the restorative object may be modified to match the treatment goals. As shown in FIG. 40, the process for obtaining the 3D bite model may begin with determining an initial tooth position 4010, such as an initial position for one or more teeth of the patient. In some embodiments, the initial positions of the teeth are determined as describe above with reference to FIGS. 1-4. At block 4020, the interim final orthodontic positions of the teeth are determined, for example as described above with reference to FIGS. 1-4.

At block 4030 the interim restorative object position is determined. The process for determining an interim restorative object position 4030 may begin by adjusting the orthodontic position to an interim orthodontic position at block 4041 and then determining at new interim restorative position at block 4032. The tooth mass loss of the new interim orthodontic position is compared to the tooth mass loss of one or more of the previous interim orthodontic and restorative positions at block 4033 wherein the new interim restorative position is evaluated. At block 4033 the final orthodontic position and the restorative object position is determined. In some embodiments, the final orthodontic position and the restorative object position is determined by selecting the final teeth positions that minimize tooth mass or volume loss among the evaluated positions. In some embodiments, the positions may be determined based on minimizing certain restorative procedures, such as minimizing the number of crowns. In some embodiments, less invasive procedures, such as the use of veneers, are given priority over more invasive restorative procedures, such as crowns and root canals or whole tooth extraction and prosthetics. This process allows for the evaluation of a new restorative position at each stage of the orthodontic treatment plan. The various interim restorative positions provide multiple options during the orthodontic treatment plan of when to apply the restorative object to the patient. The amount of tooth mass reduction can be different at each interim orthodontic position, thus providing more options.

Restorative Object Position on 3D Models

Figure 42:
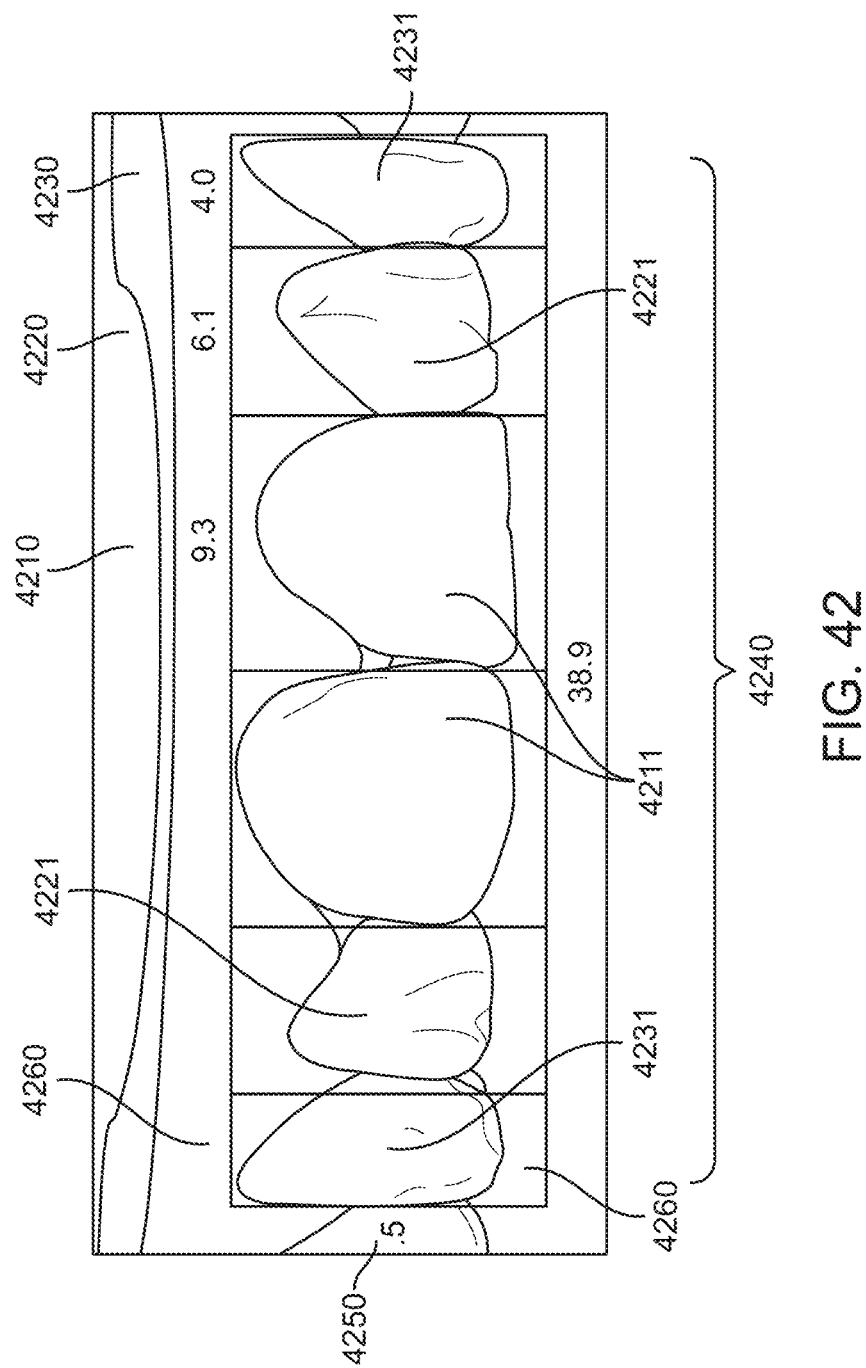
FIG. 42 depicts a portion of a method for determining tooth dimensions, in accordance with one or more embodiments herein.

The restorative object is a part of the final 3D bite model and can be modified to reach the treatment goals. One treatment goal may be the aesthetic and functional placement of the teeth. For example, in some embodiments, the final or target position of the teeth in a treatment plan may include positioning and shaping the teeth such that their shapes and positions conform to Recurring Esthetic Dental (RED) proportion. The dimensions of the boxes of the proportion widget are determined by the Recurring Esthetic Dental (RED) proportion. Under RED proportions, the successive width proportion when viewed from the facial aspect should remain constant from the midline toward the posterior for the six anterior teeth between and including the canines. This property offers great flexibility to match tooth properties with facial proportions. RED proportion may aid in determining the final shape and size of one or more restorative objects and the final or target position of the patients teeth. The 3D bite model can be assessed by determining the various dimensions of the patient's teeth, for example the widget 4260 illustrates the demarcation of the shape the teeth. FIG. 42 illustrates the various dimensions and positions of the teeth that may be determined. The dimensions of the medial incisor 4211, the lateral incisor 4221, and the canine 4231 may be measured. These dimensions may include the width of the medial incisor 4210, the width of the lateral incisor 4220, and the width of the canine 4230. Also, the intercanine width (ICW) may be determined based on the distance between the right and the left canine 4231. The height of each tooth 4250 can also be determined from the 3D bite model. The initial dimensions of the teeth are determined based on the initial 3D bite model built from the scan of the patient's teeth and using the midline plane and occlusal plane.

Figure 43:
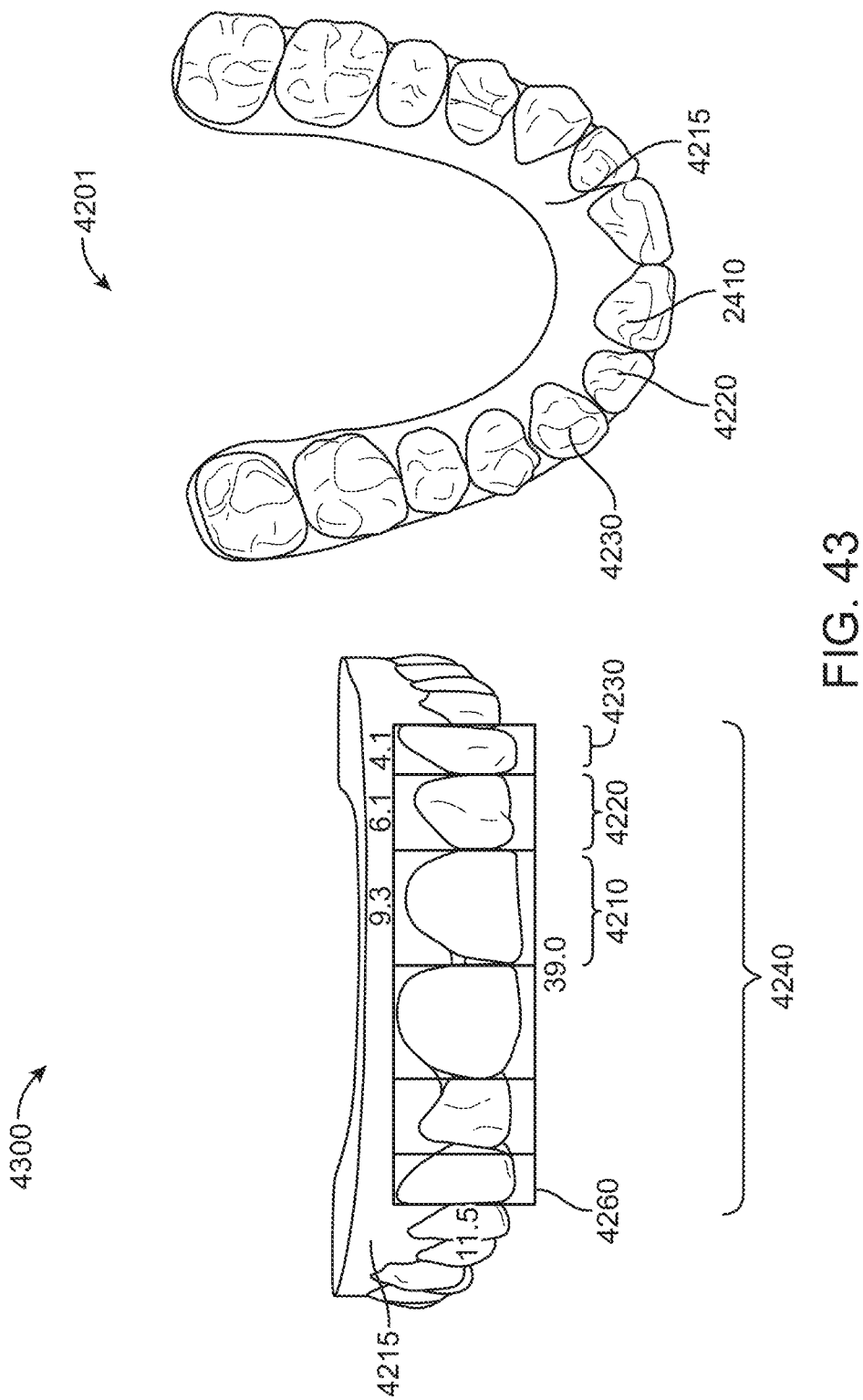
FIG. 43 depicts a portion of a method for determining tooth dimensions, in accordance with one or more embodiments herein.

FIG. 43 illustrates a 3D bite model of the upper jaw from both the anterior position on the left and from the occlusal place, on the right.

Figure 44:
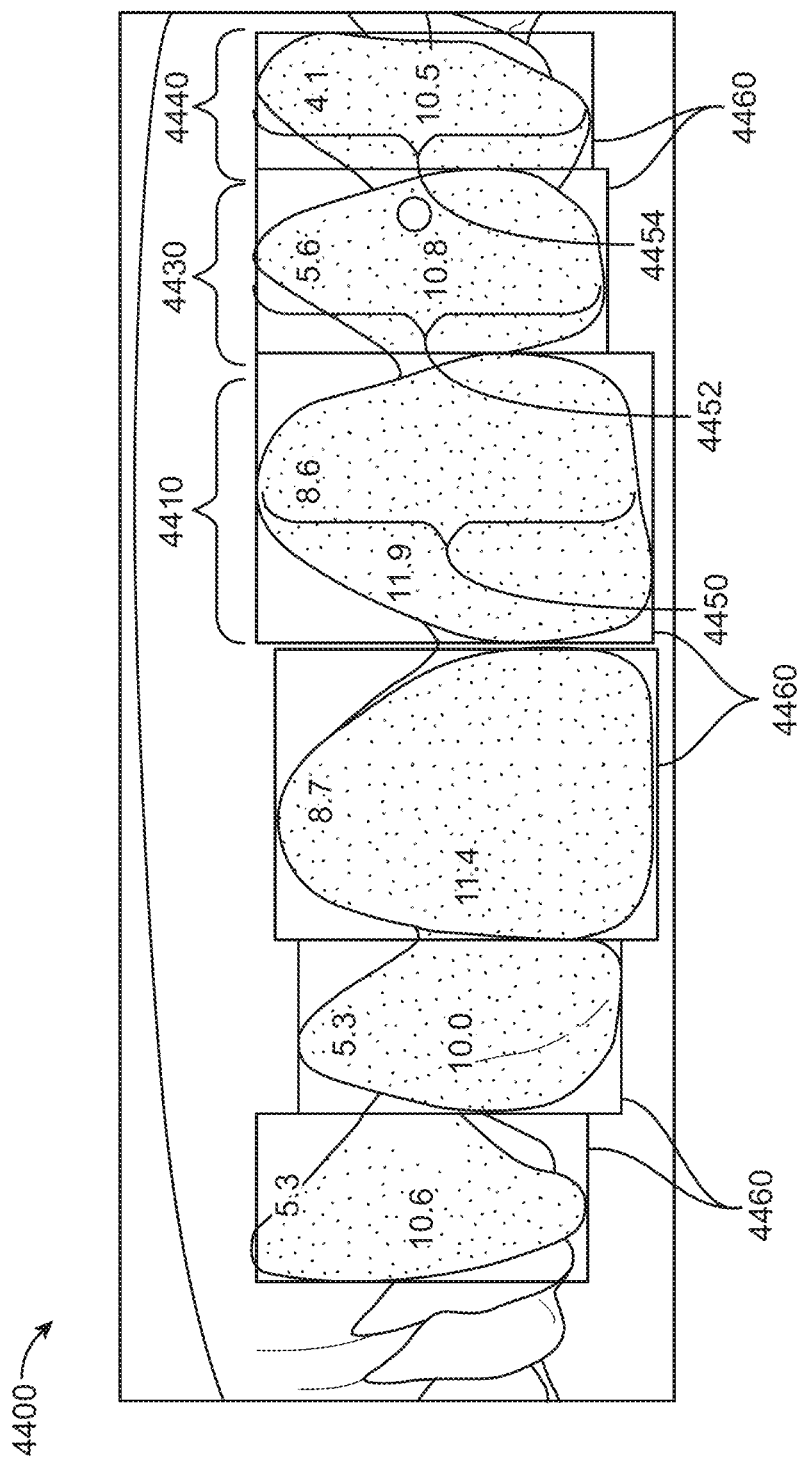
FIG. 44 depicts a portion of a method for determining tooth dimensions, in accordance with one or more embodiments herein.

FIG. 44 illustrates the modified shape and position of the restorative objects on a 3D bite model 4400. The final shape and position of the restorative object for each tooth of a plurality of teeth may be shaped according to the RED proportion as shown by the bounding boxes 4460. The width of the central incisor 4410, lateral incisor 4430, and the canine 4440 are indicated by the bounding boxes. Similarly, the height of the central incisor 4450, lateral incisor 4452, and the canine 4454 are indicated by the bounding boxes.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. A method for virtually representing an orthodontic treatment outcome of a patient's teeth, the computer-implemented method comprising:
   receiving a facial image of a patient;
   identifying a facial landmark on the facial image, wherein the facial landmark comprises at least a lip landmark;
   locating a mouth opening within the facial image based at least in part on the lip landmark;
   extracting a first set of teeth contours within the mouth opening;
   extracting a second set of teeth contours from a 3D model representing the patient's teeth rendered in an intermediate position between an initial position and a final position, wherein the intermediate position and the final position are part of a treatment plan;
   aligning the extracted second set of teeth contours with the first set of teeth contours within the mouth opening; and
   inserting the 3D model into the facial image to form a composite image.

2. The method of claim 1, further comprising:
   inserting a rendering of the 3D model into the mouth opening based at least in part on the alignment of the second set of teeth contours from the 3D model with the first set of teeth contours of the patient's teeth within the mouth opening in the facial image.

3. The method of claim 1, wherein locating the mouth opening within the facial image comprises cropping the facial image around the lip landmark to exclude other facial landmarks.

4. The method of claim 3, wherein the other facial landmarks include one or more of eye, nose, or facial outline landmarks.

5. The method of claim 1, wherein extracting the first set of teeth contours within the mouth opening comprises detecting the first set of tooth contours using a convolutional neural network.

6. The method of claim 5, wherein the convolutional neural network comprises a holistic edge detection deep learning model.

7. The method of claim 1, wherein the first set of teeth contours comprises a plurality of pixels, each pixel of the first set of teeth contours having a value to be compared with a pre-determined threshold value.

8. The method of claim 1, wherein the facial image of the patient is a 2D image.

9. The method of claim 1, further comprising:
rendering the composite image on a display, wherein the composite image comprises a 2D rendering of the 3D model.

10. The method of claim 1, further comprising:
generating a set of thinned teeth contours from the first set of teeth contours.

11. A non-transitory computer-readable storage medium including instructions that, when executed by at least one processor of a computing system, cause the computing system to perform operations comprising:
receiving a facial image of a patient;
identifying a facial landmark on the facial image, wherein the facial landmark comprises at least a lip landmark;
locating a mouth opening within the facial image based at least in part on the lip landmark;
extracting a first set of teeth contours within the mouth opening;
extracting a second set of teeth contours from a 3D model representing the patient's teeth rendered in an intermediate position between an initial position and a final position, wherein the intermediate position and the final position are part of a treatment plan; and
aligning the extracted second set of teeth contours with the first set of teeth contours within the mouth opening; and
inserting the 3D model into the facial image to form a composite image.

12. The non-transitory computer-readable storage medium of claim 11, wherein the operations further comprise:
inserting a rendering of the 3D model into the mouth opening based at least in part on the alignment of the second set of teeth contours from the 3D model with the first set of teeth contours of the patient's teeth within the mouth opening in the facial image.

13. The non-transitory computer-readable storage medium of claim 11, wherein locating the mouth opening within the facial image comprises cropping the facial image around the lip landmark to exclude other facial landmarks.

14. The non-transitory computer-readable storage medium of claim 13, wherein the other facial landmarks include one or more of eye, nose, or facial outline landmarks.

15. The non-transitory computer-readable storage medium of claim 11, wherein extracting the first set of teeth contours within the mouth opening comprises detecting the first set of tooth contours using a convolutional neural network.

16. The non-transitory computer-readable storage medium of claim 15, wherein the convolutional neural network comprises a holistic edge detection deep learning model.

17. The non-transitory computer-readable storage medium of claim 11, wherein the first set of teeth contours comprises a plurality of pixels, each pixel of the first set of teeth contours having a value to be compared with a pre-determined threshold value.

18. The non-transitory computer-readable storage medium of claim 11, wherein the facial image of the patient is a 2D image.

19. The non-transitory computer-readable storage medium of claim 11, wherein the operations further comprise rendering the composite image on a display, wherein the composite image comprises a 2D rendering of the 3D model.

20. The non-transitory computer-readable storage medium of claim 11, wherein the operations further comprise:
generating a set of thinned teeth contours from the first set of teeth contours.

* * * * *